(12) United States Patent
Ewin et al.

(10) Patent No.: US 9,206,126 B2
(45) Date of Patent: Dec. 8, 2015

(54) PHENICOL ANTIBACTERIAL AGENTS

(71) Applicant: Zoetis Services LLC, Florham Park, NJ (US)

(72) Inventors: Richard Andrew Ewin, Kalamazoo, MI (US); Timothy Allan Johnson, Richland, MI (US); Susan Mary Kult Sheehan, Galesburg, MI (US); Rajendran Vairagoundar, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/018,993

(22) Filed: Sep. 5, 2013

(65) Prior Publication Data
US 2014/0088046 A1    Mar. 27, 2014

Related U.S. Application Data

(60) Provisional application No. 61/705,815, filed on Sep. 26, 2012.

(51) Int. Cl.
| | |
|---|---|
| *C07F 9/06* | (2006.01) |
| *C07F 9/28* | (2006.01) |
| *C07D 405/00* | (2006.01) |
| *A61K 31/44* | (2006.01) |
| *C07D 213/40* | (2006.01) |
| *C07D 405/04* | (2006.01) |
| *C07D 261/08* | (2006.01) |
| *C07D 409/04* | (2006.01) |
| *C07D 213/64* | (2006.01) |
| *C07F 9/6558* | (2006.01) |
| *C07D 401/04* | (2006.01) |
| *C07D 213/50* | (2006.01) |
| *C07D 333/24* | (2006.01) |
| *C07D 333/22* | (2006.01) |
| *C07D 401/06* | (2006.01) |
| *C07D 277/56* | (2006.01) |
| *C07D 285/12* | (2006.01) |
| *C07F 9/58* | (2006.01) |
| *C07D 231/12* | (2006.01) |
| *C07D 405/06* | (2006.01) |
| *C07D 417/04* | (2006.01) |
| *C07D 277/30* | (2006.01) |
| *C07D 213/56* | (2006.01) |
| *C07D 213/57* | (2006.01) |
| *C07F 7/22* | (2006.01) |

(52) U.S. Cl.
CPC ............ *C07D 213/40* (2013.01); *C07D 213/50* (2013.01); *C07D 213/56* (2013.01); *C07D 213/57* (2013.01); *C07D 213/64* (2013.01); *C07D 231/12* (2013.01); *C07D 261/08* (2013.01); *C07D 277/30* (2013.01); *C07D 277/56* (2013.01); *C07D 285/12* (2013.01); *C07D 333/22* (2013.01); *C07D 333/24* (2013.01); *C07D 401/04* (2013.01); *C07D 401/06* (2013.01); *C07D 405/04* (2013.01); *C07D 405/06* (2013.01); *C07D 409/04* (2013.01); *C07D 417/04* (2013.01); *C07F 7/2212* (2013.01); *C07F 9/58* (2013.01); *C07F 9/65586* (2013.01)

(58) Field of Classification Search
None
See application file for complete search history.

(56) References Cited

U.S. PATENT DOCUMENTS 7,041,670 B2    5/2006   Boojamra et al.

FOREIGN PATENT DOCUMENTS

| WO | WO 03/077828 A2 * | 9/2003 |
| WO | 2012/125832 | 9/2012 |
| WO | WO 2012/125832 A2 * | 9/2012 |
| WO | 2013/134061 | 9/2013 |

OTHER PUBLICATIONS

Bolton et al., "Detection of multidrug-resistant Salmonella enterica serotype typhimurium DT104 based on a gene which confers cross-resistance to florfenicol and chloramphenicol", J. Clin. Microbiol., 37(5):1348-1351, 1999.

Keyes et al., "Detection of florfenicol resistance genes in *Escherichia coli* isolated from sick chickens", Antimicrob. Agents Chemother., 44(2):421-424, 2000.

Cloeckaert et al., "Nonenzymatic chloramphenicol resistance mediated by IncC plasmid R55 is encoded by a floR gene variant", Antimicrob. Agents Chemother., 45(8):2381-2382, 2001.

(Continued)

*Primary Examiner* — Rita Desai
*Assistant Examiner* — Ben S Michelson
(74) *Attorney, Agent, or Firm* — Paul M. Misiak; Barbara L. Renda

(57) ABSTRACT

The present invention provides novel phenicol derivatives, their use for the treatment of infections in mammals, pharmaceutical composition containing these novel compounds, and methods for the preparation of the compounds of formula I

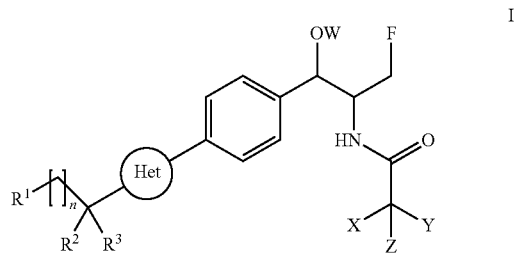

4 Claims, No Drawings

(56) References Cited

OTHER PUBLICATIONS

Kim and Aoki, "Sequence analysis of the florfenicol resistance gene encoded in the transferable R-plasmid of a fish pathogen, Pasteurella piscicida", Microbiol. Immunol., 40(9):665-669, 1996.

Cloeckaert et al., "Plasmid-Mediated Florfenicol Resistance Encoded by the floR Gene in *Escherichia coli* Isolated from Cattle", Antimicrob. Agents Chemother., 44(10):2858-2860, 2000.

PCT International Search Report, PCT/US2013/057910, mailed Oct. 31, 2013 (5 pages).

* cited by examiner

PHENICOL ANTIBACTERIAL AGENTS

FIELD OF THE INVENTION

The present invention provides novel phenicol derivatives, their use for the treatment of infections in mammals, pharmaceutical composition containing these novel compounds, and methods for the preparation of these compounds.

BACKGROUND OF THE INVENTION

There is a growing need for new antibiotic agents for the treatment of bacterial infections in animals, and in particular there is a need for new agents which overcome increasing bacterial resistance to existing antibiotics.

Florfenicol is a broad spectrum phenicol antibiotic used exclusively in veterinary medicine. Phenicol antibiotics as a class are potent inhibitors of bacterial protein biosynthesis. Florfenicol has a broad spectrum of activity against many gram-negative and gram-positive bacteria, and is useful in the prevention and treatment of bacterial infections due to susceptible pathogens in birds, reptiles, fish, shellfish and mammals. An important use of florfenicol is in the treatment of respiratory infections in cattle, such as those caused by, for example, *Mannheimia haemolytica*, *Pasteurella multocida* and *Haemophilus somnus*. Effective treatment of bovine respiratory disease (BRD) plays a significant role in reducing what is otherwise one of the leading causes of economic loss to both the dairy and beef industries worldwide.

International Publication Number WO 2012/125832 discloses antimicrobial agents. U.S. Pat. No. 7,041,670 discloses florfenicol-type antibiotics.

Reports in recent years indicate that bacterial resistance to florfenicol is developing and has been observed across multiple bacterial genera and species, such as *Salmonella* (Bolton, L. F., et al., J. Clin. Microbiol., 1999, 37, 1348), *E. coli* (Keyes, K., et al., Antimicrob. Agents Chemother., 2000, 44, 421), *Klebsiella pneumoniae* (Cloeckaert, A., et al., Antimicrob. Agents Chemother., 2001, 45, 2381), and in the aquacultural pathogen, *Photobacterium damselae* subsp. *piscicida* (formerly *Pasteurella piscicida*) (Kim, E., et al., Microbiol. Immunol., 1996, 40, 665). In light of the increasing threat of florfenicol resistance and the apparent mobility of the resistance genes across bacterial species and animal hosts (Cloeckaert, A., et al., Antimicrob. Agents Chemother., 2000, 44, 2858), there is an important need for new antibiotics that maintain or surpass the activity of florfenicol, while also overcoming the challenges of florfenicol resistance. The compounds of the present invention represent such an improvement.

SUMMARY OF THE INVENTION

The present invention provides compounds of formula I

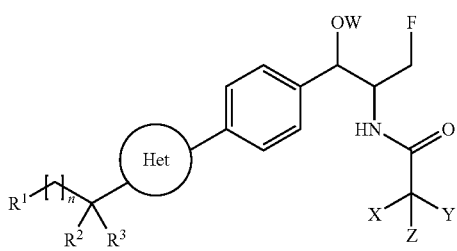

or pharmaceutical acceptable salts thereof wherein:
the Het moiety is a 4 to 14-membered cyclic ring system having from 1 to 5 hetero atoms selected from N, O, and S, wherein the heteroatom or the cyclic ring is optionally substituted with one to three $R^5$;

wherein $R^1$ is
a. —H
b. halo,
c. —OW,
d. —$OC_{1-8}$alkyl,
e. —CN,
f. —$NR^4R^5$,
g. —$C(=O)NR^4R^5$,
h. —$SR^4$,
i. —$SO_2R^4$,
j. —$SO_2NR^4R^5$,
k. —$S(C=O)R^4$
l. —S(=O), or
m. a Het moiety which is a 4 to 14-membered cyclic ring system having from 1 to 5 hetero atoms selected from N, O, and S, wherein the heteroatom or the cyclic ring is optionally substituted with one to three $R^5$;

wherein $R^2$ and $R^3$ are independently
a. —H,
b. -Halo,
c. —$C_1$-$C_6$ alkyl,
d. —CN,
e. —$C_3$-$C_6$ cycloalkyl; or wherein $R^2$ and $R^3$, taken together with the carbon atom to which they are attached, form:
a. a 3 to 6 membered heterocyclic ring moiety optionally having from 1-2 hetero atoms selected from the group consisting of N, $NR^4$, S, SO, $SO_2$ and O, wherein the heteroatom or the heterocyclic ring is optionally substituted with one to three $R^5$,
b. -carbonyl (C=O), or
c. —C=NOW;

at each occurrence, $R^4$ is —H, $C_{1-6}$alkyl, or —$C_{3-6}$cycloalkyl, wherein said alkyl is optionally substituted with one, two or three $R^5$;

at each occurrence, $R^5$ is —H, —OH, halo, —CN, —$NO_2$, $C_{1-6}$alkyl, —$C_{3-6}$cycloalkyl, oxo (=O), —$NH_2$, —$NHC_{1-4}$alkyl, —$N(C_{1-4}alkyl)_2$, —$OC_{1-4}$alkyl, oxo, —SH, —$SC_{1-4}$alkyl, —$S(C=O)C_{1-4}$alkyl, —$SONC_{1-4}$alkyl, —$C(=O)C_{1-4}$alkyl, —$C(=O)NH_2$, —$C(=O)NHC_{1-4}$alkyl, —$C(=O)N(C_{1-4}alkyl)_2$, —$NC(=O)NH_2$, —$NC(=O)NHC_{1-4}$alkyl, $NC(=O)N(C_{1-4}alkyl)_2$, —$SO_2C_1$-$C_6$ alkyl, or —$SO_2C_3$-$C_6$ cycloalkyl; wherein the alkyl and cycloalkyl are optionally substituted with Halo;

wherein n is zero to four;
wherein W is —H, —$PO(OH)_2$, —$CH_2OPO(OH)_2$, —$C(=O)C_{1-4}$alkyl, or —$CH_2OC(=O)C_{1-4}$alkyl, wherein $C_{1-4}$alkyl is optionally substituted with —$OCO_2H$, —$OCO_2C_{1-4}$alkyl, or —$OC(=O)NHC_{1-4}$alkyl;

wherein X, Y and Z are independently —H, -halo, —$C_{1-4}$alkyl, —$C_{1-4}$cycloalkyl, —OH, —$CF_3$, —$NH_2$, —CN, —$N_3$ or —$SCF_3$;

with the following provisos:
a) when $R^1$ is $NR^4R^5$, n is one to four;
b) when $R^1$ is —H, -Halo, or —OW, $R^2$ and $R^3$ are taken together with the carbon atom to which they are attached to form a 3 to 6 membered heterocyclic ring moiety optionally having from 1-2 hetero atoms selected from the group consisting of N, $NR^4$, S, SO, $SO_2$ and O, wherein the heteroatom or the cyclic ring is optionally substituted with one to three $R^5$; and
c) when $R^1$ is —OH or $OC_{1-8}$alkyl and n is zero, $R^2$ and $R^3$ are taken together to form a moiety other than a -carbonyl (C=O).

Specific embodiments of Het include moieties, such as pyridinyl, oxo-pyridinyl, isoxazolyl, thiazolyl, thiadiazolyl, thiophenyl, oxazolyl, pyrazolyl, and thiadiazolyl.

More specific embodiments of Het include pyridinyl, oxo-pyridinyl, isoxazolyl, thiazolyl, and thiophenyl.

Specific embodiments of the compounds of formula I include compounds such as the following: compounds wherein n is 0 or 1; compounds wherein W is H, —PO(OH)$_2$, or —CH$_2$OPO(OH)$_2$; and compounds wherein W is H.

Specific embodiments of the present invention include compounds of formula I wherein R$^2$ and R$^3$ are taken together with the carbon to which they are attached to form a 4 to 6 membered heterocyclic ring moiety optionally having 1-2 hetero atoms selected from the group consisting of N, NR$_4$, S, SO, SO$_2$, and O, wherein the heteroatom or the heterocyclic is optionally substituted with R$^5$.

More specific embodiments of the present invention include compounds of formula I wherein R$^2$ and R$^3$ are taken together with the carbon to which they are attached to form an oxetanyl or an azetidinyl.

Specific embodiments of the compounds of the present invention include compounds of formula I wherein R$^1$ is —OW, -Halo, —CN, or SO$_2$R$^4$; wherein W is hydrogen or —PO(OH)$_2$; and R$^4$ is —C$_1$-C$_6$alkyl.

Specific embodiments of the compounds of the present invention include compounds of formula I wherein X, Y and Z are independently H or fluoride; or wherein X, Y and Z are independently H or chloride.

In another aspect, the present invention also provides:

pharmaceutical compositions which comprise a pharmaceutically acceptable carrier and compounds of formula I;

methods for controlling or treating infections in mammals by administering to mammals in need thereof therapeutically effective amounts of compounds of formula I or pharmaceutically acceptable salts thereof;

methods for controlling or treating infections in livestock and companion animals by administering to livestock or companion animals in need thereof therapeutically effective amounts of compounds of formula I or pharmaceutically acceptable salts thereof; and methods for the preparation of compounds of the present invention.

DETAILED DESCRIPTION

With respect to the above compound, and throughout the application and claims, the following terms have the meanings defined below.

The term "halo" refers to chloro, bromo, fluoro, and iodo.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-4}$ alkyl refers to alkyl of one to four carbon atoms, inclusive; $C_{1-6}$ alkyl refers to alkyl of one to six carbon atoms, inclusive; and $C_{1-8}$ alkyl refers to alkyl of one to eight carbon atoms, inclusive.

The term alkyl refers to straight, branched and a cyclic saturated monovalent hydrocarbon groups, but reference to an individual radical such as "propyl" embraces only the straight chain radical, a branched chain isomer such as "isopropyl" or a cyclic isomer such as cyclopropylmethyl or cyclopentyl being specifically referred to.

The term "cycloalkyl" refers to a mono ring such as cyclopropyl, cyclobutyl, cyclopentyl, or cyclohexyl.

The term "Het" refers to saturated or unsaturated monocyclic or bicyclic heterocyclics, containing at least one heteroatom selected from N, O, and S. Bicyclic heterocyclics rings may be fused, spiro, or bridged ring systems. Monocyclic heterocyclic rings contain from 4- to 10-ring atoms, preferably from 5- to 6-member atoms in the ring. Bicyclic heterocyclics contain from 7 to 14 member atoms, preferably 9 to 12 member atoms in the ring. Examples of heterocyclic groups include, but are not limited to, substituted or unsubstituted tetrahydrofuran, dioxane, pyrrolidine, piperidine, piperazine, tetrahydrotriazine, tetrahydropyrazole, tetrahydrothiophene, dihydro-1,3-dithiol-2-yl, hexahydrothiepin-4-yl, thienyl, furanyl, pyrrolyl, imidazolyl, pyrazolyl, isothiazolyl, isoxazolyl, triazoiyl, tetrazolyl, pyridinyl, pyridonyl, oxo-pyridinyl, pyrazinyl, pyrimidinyl, piperidinyl, pyrrolidinyl, piperazinyl, azetidinyl, aziridinyl, morpholinyl, thietanyl, oxetaryl, isoxazolyl, thiazolyl, thiadiazolyl and thiophenyl. Examples of suitable bicyclic heterocyclic groups include, but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

For heterocyclic groups containing sulfur, the oxidized sulfur such as SO or SO$_2$ groups are also included.

For heterocyclic groups containing nitrogen, nitrogen groups such as N→O or NH are also included.

At each occurrence, Het is optionally substituted at the heteroatom or the cyclic ring with one to three OH, halo, —CN, —NO$_2$, C$_{1-6}$alkyl, —C$_{3-6}$cycloalkyl, oxo (=O), —NH$_2$, —NHC$_{1-4}$alkyl, —N(C$_{1-4}$alkyl)$_2$, —OC$_{1-4}$alkyl, —SH, —SC$_{1-4}$alkyl, —S(C=O)C$_{1-4}$alkyl, —SONC$_{1-4}$alkyl, —C(=O)C$_{1-4}$alkyl, —C(=O)NH$_2$, —C(=O)NHC$_{1-4}$alkyl, —C(=O)N(C$_{1-4}$alkyl)$_2$, —NC(=O)NH$_2$, —NC(=O)NHC$_{1-4}$alkyl, NC(=O)N(C$_{1-4}$alkyl)$_2$, —SO$_2$C$_1$-C$_6$ alkyl, or —SO$_2$C$_3$-C$_6$ cycloalkyl; wherein the alkyl and cycloalkyl are optionally substituted with Halo.

The term "mammal" refers to human or animals including livestock and companion animals. The phrase "companion animal" or "companion animals" refers to animals kept as pets. Examples of companion animals include cats, dogs, and horses. The term "livestock" refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys. Specifically, livestock animals of the present invention refer to cattle and pigs.

The term "controlling", "treating" or "treatment" of a disease includes: (1) preventing the disease, i.e., causing the clinical symptoms or signs of the disease not to develop in a mammal that may be exposed to or predisposed to the disease but does not yet experience or display symptoms/signs of the disease; (2) inhibiting the disease, i.e., arresting or reducing the development of the disease or its clinical symptoms/signs; or (3) relieving the disease, i.e., causing regression of the disease or its clinical symptoms/signs.

The term "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "pharmaceutically acceptable" means suitable for use in mammals, companion animals or livestock animals.

The term "prodrug" refers to a bio-reversible derivative of a molecule, i.e., a compound of formula I of the present invention. Prodrugs can alter the solubility, lipophilicity and in-vivo distribution of drugs. By deliberately altering these key properties, it may be possible to improve absorption, enhance onset time, reduce first pass metabolism, allow development of aqueous IV formulations and achieve targeted delivery. In addition, prodrugs are useful in improving transdermal delivery, masking taste, minimizing pain on injection, improving stability, etc. In situations where the pharmacophore itself leads to poor delivery properties, prodrugs are one of the few strategies that can be used to salvage the highly active compound. Included within the scope of the present invention are all prodrugs of the compounds of formula I that can be prepared by the standard methods known to one skilled in the art. Prodrugs of the compounds of formula I may be prepared following the methods described in "Prodrugs of phosphates, phosphonates, and phosphinates", Krise J P, Stella V J, Advanced Drug Delivery Reviews, 19: (2) 287-310 MAY 22 1996; "Targeted Prodrug Design to Optimize Drug Delivery". Hyo-Kyung Han and Gordon Amidon. AAPS PharmSci 2000; 2 (1) article 6; "Prodrugs", L. Prokai and K. Prokai-Tatrai, Chapter 12 in *Injectable Drug Development: Techniques to Reduce Pain and Irritation*, Interpharm Press, Buffalo Grove, Ind., 1999; "Improved oral drug delivery: Solubility limitations overcome by the use of prodrugs", Fleisher D, Bong R, Stewart B H, Advanced Drug Delivery Reviews, 19: (2) 115-130 MAY 22 1996; or "Preparation and hydrolysis of water soluble, non-irritating prodrugs of pharmaceuticals with oxaalkanoic acids", Crooks, Peter Anthony; Cynkowski, Tadeusz; Cynkowska, Grazyna; Guo, Hong; Ashton, Paul. PCT Int. Appl. (2000), 65 pp.

Compounds that have the same molecular formula but differ in the nature or sequence of bonding of their atoms or the arrangement of their atoms in space are termed "isomers".

Included within the scope of the described compounds are all isomers (e.g., cis-, trans-, enantiomers, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds.

A specific value for W is H, —PO(OH)$_2$, or —CH$_2$OPO(OH)$_2$.

A specific value for W is H.

A specific value for Het moiety is a 5- or 6-membered cyclic ring system having from 1 to 3 hetero atoms selected from N, O, and S including hetero atom groups such as S—O, —SO$_2$, N→O, and —NH. The Het moiety is optionally substituted with R$^6$.

A specific value for Het moiety is pyridinyl, thiophenyl, thiazolyl, thiadiazolyl, imidazolyl, oxadiazolyl, pyrimidinyl, pyrazinyl, oxazole, isoxazole, isothiazole, or pyridazine.

A specific value for Het moiety is pyridinyl or isoxazolyl.

A specific value for X, Y and Z are independently H or chloride.

A specific value for X, Y and Z are independently H or fluoride.

A specific value for a compound of the present invention is wherein W is H or —PO(OH)$_2$; Het moiety is a 5- or 6-membered cyclic ring system having from 1 to 3 hetero atoms selected from N, O, and S, optionally substituted with R$^6$;

The reaction schemes in the Examples illustrate the general synthetic procedures of the compounds of the present invention. All starting materials are prepared by procedures described in these schemes or by procedures known to one of ordinary skill in the art.

Pharmaceutical Salts

The compound of formula I may be used in its native form or as a salt. In cases where forming a stable nontoxic acid or base salt is desired, administration of the compound as a pharmaceutically acceptable salt may be appropriate. Pharmaceutically acceptable salts of the compounds of formula I include the acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remington's Pharmaceutical Sciences", Mack Pub. Co., New Jersey (1991).

The formulations of the invention can be designed to be short-acting, fast-releasing, long-acting, extended-releasing, or controlled-releasing. Specifically, the formulation of the invention can be an extended release form. Thus, the pharmaceutical formulations can also be formulated for controlled release or for slow release.

Dosage

Pharmaceutical compositions suitable for use in the present invention include compositions wherein the active ingredients are contained in an amount sufficient to achieve the intended purpose, i.e., control or the treatment of infections. More specifically, a therapeutically effective amount means an amount of compound effective to prevent, alleviate or ameliorate symptoms/signs of infections or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.1 mg to about 20 mg/kg of body weight/day, preferably about 0.1 to about 5 mg/kg of body weight/day. It is to be understood that the dosages may vary depending upon the requirements of each subject and the severity of the infections.

The desired dose may conveniently be presented in a single dose or as divided doses administered at appropriate intervals, for example, as two, three, four or more sub-doses per day. Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Medical and Veterinary Uses

Compounds of the present invention provides novel phenicol antibacterial agents for the treatment of respiratory disease infections in cattle and swine caused by Gram-negative respiratory pathogens, such as M. haemolytica, P. multocida, H. somnus, M. bovis and A. pleuropneumoniae, and Gram-positive respiratory pathogens, such as Strep. suis.

Antibacterial Assays

Compounds of the present invention are tested against an assortment of Gram-negative and Gram-positive organisms using the industrial standard techniques described in M31-A3. Performance Standards for Antimicrobial Disk and Dilution Susceptibility Tests for Bacteria Isolated from Animals; Clinical and Laboratory Standards Institute, Approved Standard-Third Edition. The compounds of the present invention demonstrates very good antibacterial activity against bovine and swine respiratory disease pathogens such as, M. haemolytica., P. multo., H, somni, M. bovis, A. pleuropneumoniae and Strep. suis.

EXAMPLES

The synthesis of compounds of the present invention is further illustrated by the following examples. The starting materials and various intermediates utilized in the examples may be obtained from commercial sources, or are readily prepared from commercially available organic compounds, using well-known methods to one skilled in the art.

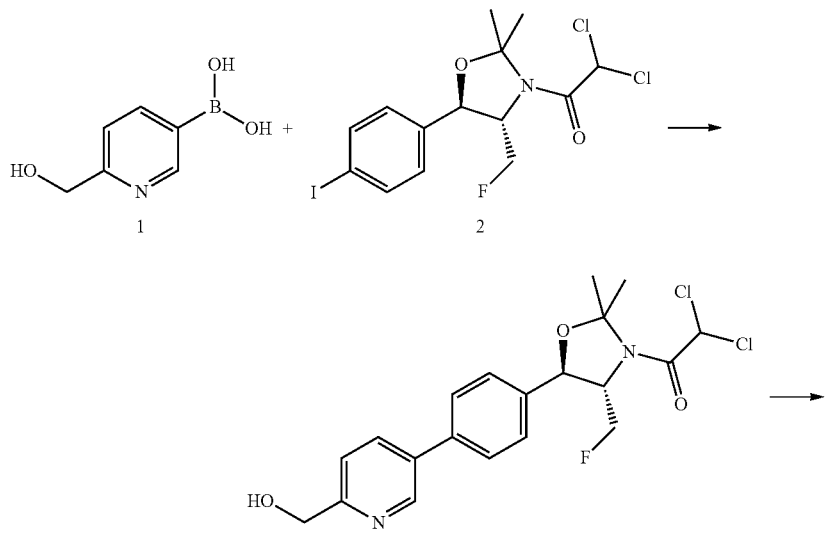

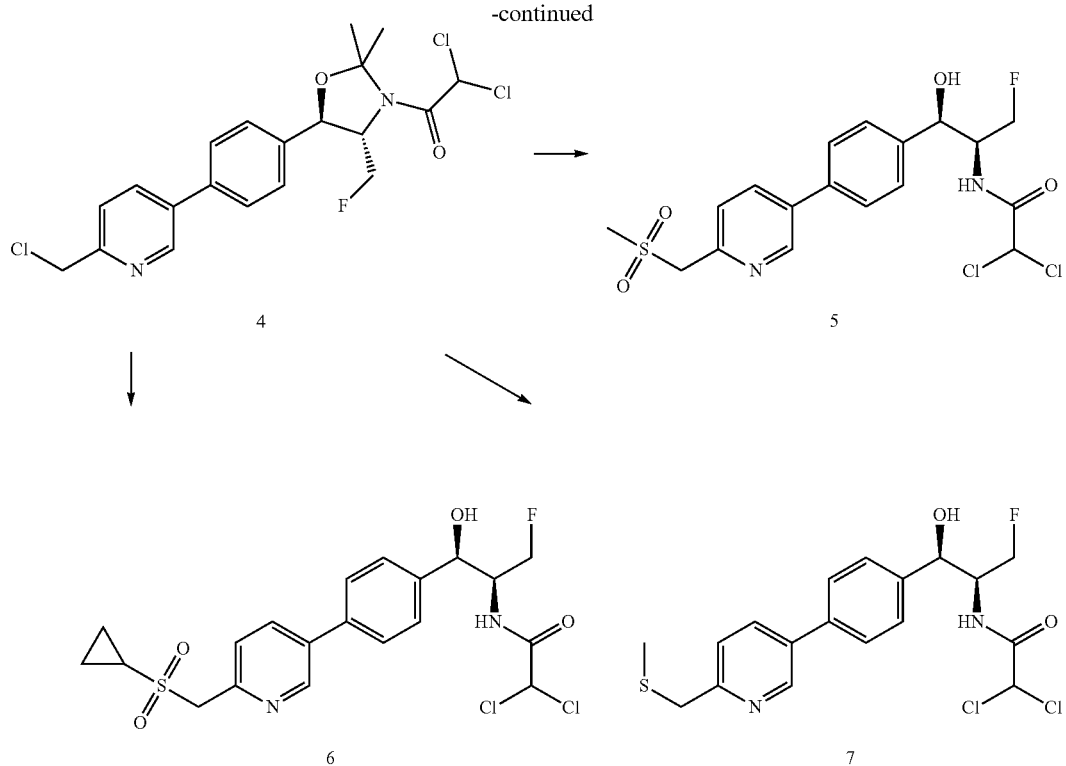

Examples 1 and 2

Preparation of 2,2-dichloro-N-((1R,2S)-3-fluoro-1-hydroxy-1-(4-(6-((methylsulfonyl)methyl)pyridin-3-yl)phenyl)propan-2-yl)acetamide

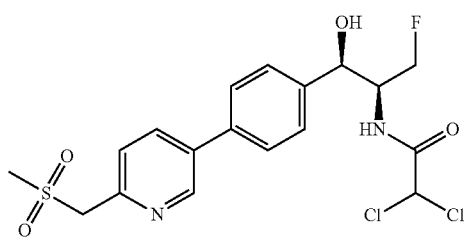 [SMILES: CS(=O)(=O)Cc1ccc(-c2ccc([C@@H](O)[C@@H](CF)NC(=O)C(Cl)Cl)cc2)cn1]

Step 1: Preparation of 2,2-dichloro-1-((4S,5R)-4-(fluoromethyl)-5-(4-(6-(hydroxymethyl)pyridin-3-yl)phenyl)-2,2-dimethyloxazolidin-3-yl)ethanone

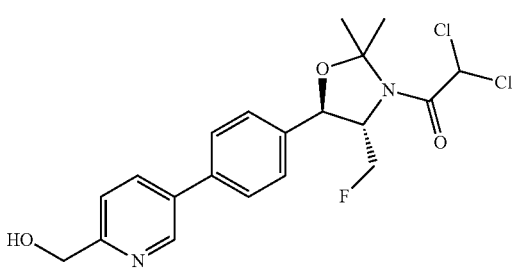 [SMILES: CC1(C)O[C@H](c2ccc(-c3ccc(CO)nc3)cc2)[C@@H](CF)N1C(=O)C(Cl)Cl]

A mixture of commercially available (6-(hydroxymethyl)pyridin-3-yl)boronic acid (1.020 g, 5.38 mmol), 2,2-dichloro-1-((4S,5R)-4-(fluoromethyl)-5-(4-iodophenyl)-2,2-dimethyloxazolidin-3-yl)ethanone (2.0 g mg, 4.48 mmol), Cs$_2$CO$_3$ (4.38 g, 13.4 mmol) in dioxane (40 mL) and water (25 mL) is bubbled with nitrogen gas for 2 minutes. To this mixture is added Pd(PPh$_3$)$_4$ (518 mg, 0.44 mmol) and the resulting reaction mixture heated to 80° C. in microwave reactor for 6 hours. The reaction is diluted with water (20 ml) and extracted with ethyl acetate (3×20 mL). The combined organic solution is dried over Na$_2$SO$_4$ and concentrated. The crude product is adsorbed on celite, and purified on silica gel column using 0 to 50% EtOAC/heptane to give the title compound (800 mg): LCMS m/z (Cl): 427 [M+H].

Step 2: Preparation of 2,2-dichloro-1-((4S,5R)-5-(4-(6-(chloromethyl)pyridin-3-yl)phenyl)-4-(fluoromethyl)-2,2-dimethyloxazolidin-3-yl)ethanone

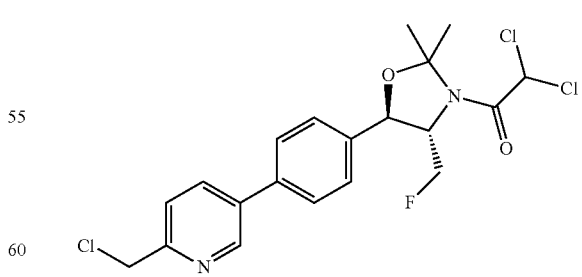

To a cooled (ice-water) solution of the product of step 1 (800 mg, 1.87 mmol) and DIPEA (0.675 mL, 3.75 mmol) in DCM (10 mL) is slowly added methanesulfonyl chloride (0.150 mL, 1.87 mmol). The reaction mixture is stirred at room temperature for 6 hours. The reaction is diluted with DCM (10 mL), washed with water (2×10 mL) dried over Na₂SO₄ and concentrated under reduced pressure to give the title compound (813 mg): LCMS m/z (Cl): 445 [M+H].

Step 3: Preparation of 2,2-dichloro-N-((1R,2S)-3-fluoro-1-hydroxy-1-(4-(6-((methylsulfonyl)methyl)pyridin-3-yl)phenyl)propan-2-yl)acetamide

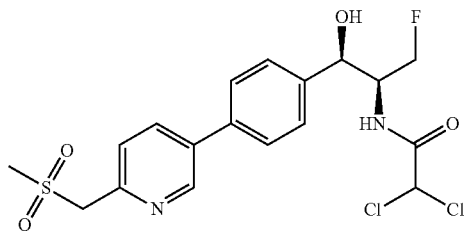 [SMILES: CS(=O)(=O)Cc1ccc(-c2ccc([C@@H](O)[C@@H](CF)NC(=O)C(Cl)Cl)cc2)cn1]

The product of step 2 (50 mg, 0.11 mmol) and sodium methanesulfinate (23 mg, 0.22 mmol) in dimethylformamide (1 mL) is heated at 60° C. for 1 hour. The solvent is removed under reduced pressure and DCM (1 mL) is added, followed by trifluoroacetic acid (0.25 mL). The reaction mixture is stirred at room temperature for 3 hours. The reaction mixture is diluted with toluene (5 mL) then the solvent removed under reduced pressure. The crude material is purified using HPLC (5 to 95 acetonitrile/water) to give title compound (17 mg): $^1$H NMR (400 MHz, DMSO-d₆) δ:3.03 (s, 3H), 4.15-4.34 (m, 1.5H), 4.38-4.46 (m, 0.5H), 4.55-4.62 (m, 0.5H), 4.65-4.76 (m, 2.5H), 4.89 (t, J=4.0 Hz, 1H), 6.00 (d, J=4.0 Hz, 1H), 6.53 (s, 1H), 7.49 (d, J=8.0 Hz, 2H), 7.58 (d, J=8.0 Hz, 1H), 7.72 (d, J=8.0 Hz, 2H), 8.11-8.17 (m, 1H), 8.62 (d, J=8.0 Hz, 1H), 8.90 (bs, 1H). m/z (Cl) 449 [M+H].

Example 2

Preparation of 2,2-dichloro-N-((1R,2S)-1-(4-(6-((cyclopropylsulfonyl)methyl)pyridin-3-yl)phenyl)-3-fluoro-1-hydroxypropan-2-yl)acetamide

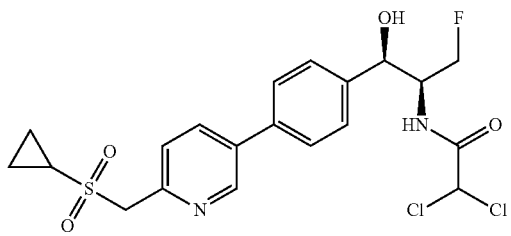 [SMILES: O=C(N[C@H](CF)[C@H](O)c1ccc(-c2ccc(CS(=O)(=O)C3CC3)nc2)cc1)C(Cl)Cl]

The product of step 2 (50 mg, 0.11 mmol) and sodium cyclopropylsulfinate (28 mg, 0.22 mmol) in dimethylformamide (1 mL) is heated at 60° C. for 1 hour. The solvent is removed under reduced pressure and DCM (1 mL) is added, followed by trifluoroacetic acid (0.25 mL). The reaction mixture is stirred at room temperature for 3 hours. The reaction mixture is diluted with toluene (5 mL) then the solvent removed under reduced pressure. The crude material is purified using HPLC (5 to 95 acetonitrile/water) to give title compound (22 mg): m/z (Cl) 475 [M+H].

Example 3

Preparation of: 2,2-dichloro-N-((1R,2S)-3-fluoro-1-hydroxy-1-(4-(6-((methylthio)methyl)pyridin-3-yl)phenyl)prop 2-yl)acetamide

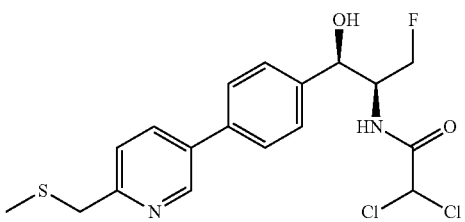 [SMILES: CSCc1ccc(-c2ccc([C@@H](O)[C@@H](CF)NC(=O)C(Cl)Cl)cc2)cn1]

The product of step 2 of Examples 1 & 2 (50 mg, 0.11 mmol) and sodium methylthiolate (16 mg, 0.22 mmol) in dimethylformamide (1 mL) is heated at 60° C. for 1 h and then the solvent is removed under high vacuum. Obtained crude product in DCM (1 mL) is added TFA (0.25 mL) and stirred the reaction mixture at room temperature for 3 hours. Reaction mixture is diluted with toluene (5 mL) concentrated in vacuo to a residue. Crude product dissolved in dimethylformamide (1 ml) and purified using HPLC (5 to 95 Acetonitrile/water) to get title compound (6 mg). m/z (Cl) 417 [M+H].

Example 4

Preparation of: 2,2-dichloro-N-((1R,2S)-1-(4-(6-(cyanomethyl)pyridin-3-yl)phenyl)-3-fluoro-1-hydroxypropan-2-yl)acetamide

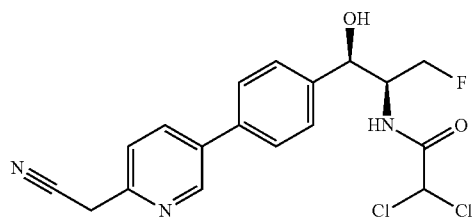 [SMILES: N#CCc1ccc(-c2ccc([C@@H](O)[C@@H](CF)NC(=O)C(Cl)Cl)cc2)cn1]

Step 1: Preparation of 2,2-Dichloro-N-((1R,2S)-3-fluoro-1-hydroxy-1-(4-iodophenyl)propan-2-yl)acetamide

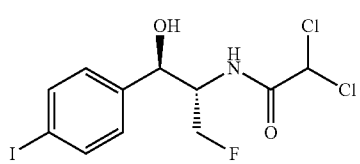 [SMILES: O=C(N[C@H](CF)[C@H](O)c1ccc(I)cc1)C(Cl)Cl]

To a solution of commercially available (1R,2S)-2-amino-3-fluoro-1-(4-iodophenyl)-1-ol (5.0 g, 20.0 mmol) in methanol (100 mL) is added triethylamine (9.56 mL, 67.8 mmol) and ethyldichloroacetate (6.22 mL, 50.8 mmol) and the mixture heated to reflux for 16 hours. After allowing to cool to room temperature, the solvent is removed under reduced pressure and the resultant oil purified by column chromatography eluting from neat heptanes to 80% ethylacetate/heptanes to give the title compound (5.94 g). m/z (Cl) M+H 405.

Step 2: Preparation of 2,2-Dichloro-N-((1R,2S)-3-fluoro-1-hydroxy-1-(4-(trimethylstannyl)phenyl)-propan-2-yl)acetamide

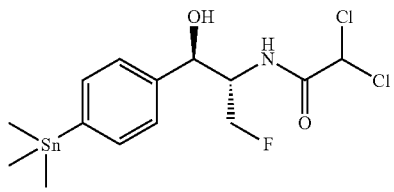 [SMILES: [CH3][Sn]([CH3])([CH3])[c]1ccc([C@@H](O)[C@@H](CF)NC(=O)C(Cl)Cl)cc1]

Hexamethylditin (196 mg, 0.59 mmol) is added to a degassed solution of the product of step 1—Example 4 (0.20 g, 1.00 mmol) and palladium tetrakistriphenylphosphine (30 mg, 0.025 mmol) in toluene (10 ml). The mixture is heated to reflux for 3 hours. The mixture is cooled and filtered through a plug of celite. The filtrates are partitioned between $CH_2Cl_2$ (10 mL) and water (10 mL). The organics were separated, dried over $MgSO_4$, filtered and evaporated to give a residue, which is purified using column chromatography eluting from neat heptanes to neat ethylacetate to give the title compound (37 mg): m/z (Cl) M+H 443.

Step 3: Preparation of 2,2-dichloro-N-((1R,2S)-1-(4-(6-(cyanomethyl)pyridin-3-yl)phenyl)-3-fluoro-1-hydroxypropan-2-yl)acetamide

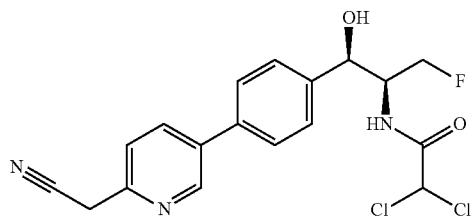 [SMILES: N#CCc1ccc(-c2ccc([C@@H](O)[C@@H](CF)NC(=O)C(Cl)Cl)cc2)cn1]

To a solution of commercially available 2-(5-bromopyridin-2-yl)acetonitrile (90 mg, 0.45 mmol) in degassed 1-methyl-2-pyrrolidone (4 mL) is added the product of step 2—Example 4 (200 mg, 0.45 mmol) and tris(2-furyl)phosphine (21 mg, 0.09 mmol). Trisdibenzylideneacetone dipalladium (41 mg, 0.045 mmol) is added and the reaction mixture heated to 80° C. for 4 hours. The mixture is diluted with ethyl acetate, washed with water (10 mL) then brine (10 mL), dried over $MgSO_4$, filtered, and the solvent removed under reduced pressure. The crude material is purified by column chromatography on silica gel eluting with a gradient of ethyl acetate/heptane to afford the title compound (65 mg): $^1$H NMR (400 MHz, $CDCl_3$) δ: 4.20-4.50 (m, 4H), 4.50-4.80 (m, 1H), 4.92 (t, J=3.4 Hz, 1H), 6.00 (d, J=4.0 Hz, 1H), 6.53 (s, 1H), 7.50 (m, 3H), 7.69 (d, J=8.2 Hz, 2H), 8.12 (dd, J=8.2 and 2.3 Hz, 1H), 8.62 (d, J=8.2, 1H), 8.86 (d, J=8.2 Hz, 1H). m/z (Cl) 397 [M+H].

Example 5

Preparation of: N-((1R,2S)-1-(4-(6-(2-amino-2-oxoethyl)pyridin-3-yl)phenyl)-3-fluoro-1-hydroxypropan-2-yl)-2,2-dichloroacetamide

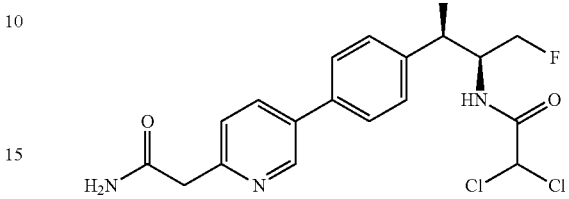

The product of step 3 of Example 4 (10 mg, 0.025 mmol) is stirred with concentrated sulfuric acid (0.5 mL) at room temperature for 30 minutes. The solution is basified with saturated aqueous sodium bicarbonate (5 mL) and extracted with 10% methanol in $CH_2Cl_2$ (10 mL). The organics are concentrated and the residue purified by chromatography on a reverse phase C-18 column eluting with a gradient of neat water with 0.1% trifluoroacetic acid to neat acetonitrile with 0.1% trifluoroacetic acid to give the title compound (2 mg): m/z (Cl) 415 [M+H].

Example 6

Preparation of 2,2-dichloro-N-((1R,2S)-3-fluoro-1-hydroxy-1-(4-(6-(2-(methylsulfonyl)ethyl)pyridin-3-yl)phenyl)propan-2-yl)acetamide

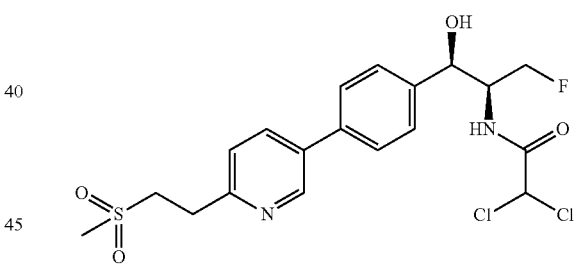

Step 1: Preparation of 2-(5-bromopyridin-2-yl)ethanol

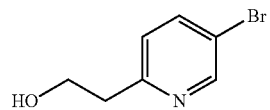

Commercially available 2-(5-bromopyridin-2-yl)acetic acid (1.00 g, 4.6 mmol) in tetrahydrofuran (10 mL) is cooled to 5° C. and treated dropwise over 10 minutes with borane-tetrahydrofuran complex (13.9 mL, 13.9 mmol). After stirring at room temperature for 4 hours, the reaction mixture is quenched with saturated aqueous potassium carbonate (20 mL), extracted with ethyl acetate (50 mL), dried over $MgSO_4$, filtered, the solvent removed under reduced pressure, and the crude material purified by column chromatography on silica gel eluting with a gradient of neat heptane to neat ethyl acetate to afford the title compound (1.09 g): m/z (Cl) 203 [M+H].

Step 2: Preparation of 5-bromo-2-(2-(methylsulfonyl)ethyl)pyridine

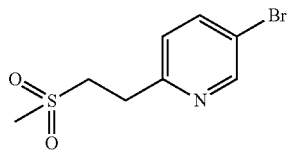

The product of Step 1 of Example 6 (940 mg, 4.65 mmol) in dimethylformamide (5 mL) at 5° C. is treated with triphenylphosphine (1710 mg, 6.5 mmol) and N-bromosuccinimide (1.24 g, 7.0 mmol) then stirred for 1 hour. Sodium methanesulfinate (980 mg, 9.3 mmol) and tetrabutylammonium iodide (175 mg, 0.45 mmol) are added and the mixture heated at 70° C. for 1 hour then cooled to room temperature, diluted with ethyl acetate (25 mL), washed with water (25 mL) and brine (25 mL), dried over MgSO$_4$, filtered, concentrated, and the crude material purified by column chromatography on silica gel eluting with a gradient of ethyl acetate/heptane to afford the title compound (570 mg): m/z (CI) 265 [M+H].

Step 3: Preparation of 2,2-dichloro-N-((1R,2S)-3-fluoro-1-hydroxy-1-(4-(6-(2-(methylsulfonyl)ethyl)pyridin-3-yl)phenyl)propan-2-yl)acetamide

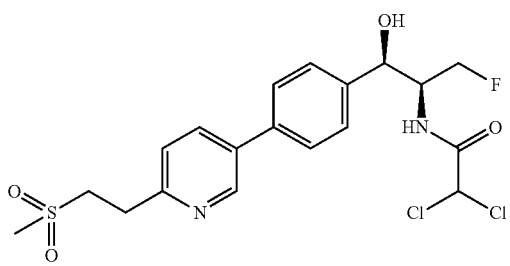 [SMILES: CS(=O)(=O)CCc1ccc(-c2ccc([C@@H](O)[C@@H](CF)NC(=O)C(Cl)Cl)cc2)cn1]

To a solution of 5-bromo-2-(2-(methylsulfonyl)ethyl)pyridine (119 mg, 0.45 mmol) in degassed N-Methyl-2-pyrrolidone (4 mL) is added to a mixture of the product of step 2—Example 4 (200 mg, 0.45 mmol) and tris(2-furyl)phosphine (21 mg, 0.09 mmol). Tris(dibenzylideneacetone) dipalladium (41 mg, 0.045 mmol) is added and the reaction mixture heated to 80° C. for 4 hours. After cooling to room temperature the mixture is diluted with ethyl acetate (20 mL), washed with water (20 mL) and brine (20 mL), dried over MgSO$_4$, filtered, concentrated, and the crude material purified by column chromatography on silica gel eluting with a gradient of ethyl acetate/heptane to afford the title compound (65 mg): $^1$H NMR (400 MHz, CDCl$_3$) δ: 3.03 (s, 3H), 3.24 (m, 2H), 3.58 (m, 2H), 4.10-4.50 (m, 2H), 4.50-4.80 (m, 1H), 4.92 (t, J=3.5 Hz, 1H), 5.99 (d, J=4.3 Hz, 1H), 6.53 (s, 1H), 7.48 (m, 3H), 7.68 (d, J=8.2, 1H), 8.02 (dd, J=8.2 and 2.3 Hz, 1H)8.62 (dd, J=8.8 Hz, 1H), 8.82 (d, J=1.8 Hz, 1H). m/z (CI) 464 [M+H].

Example 7

Preparation of 2,2-difluoro-N-((1R,2S)-3-fluoro-1-hydroxy-1-(4-(6-(methylsulfonylmethyl)pyridin-3-yl)phenyl)propan-2-yl)acetamide

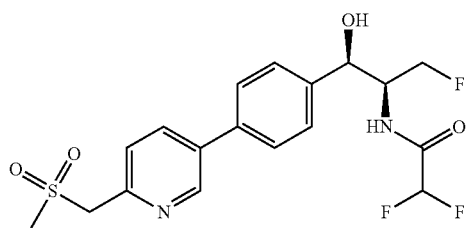 [SMILES: CS(=O)(=O)Cc1ccc(-c2ccc([C@@H](O)[C@@H](CF)NC(=O)C(F)F)cc2)cn1]

Step 1: Preparation of 5-bromo-2-(methylsulfonylmethyl)pyridine

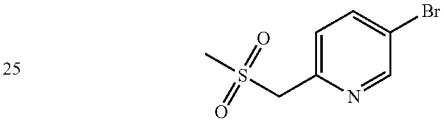

Commercially available (5-bromopyridin-2-yl)methanol (2000 mg, 10.6 mmol) in CH$_2$Cl$_2$ (20 mL) is treated with di-isopropylethylamine (2.8 mL, 16 mmol) and methane sulfonylchloride (1.0 mL, 12.8 mmol) stirred for 1 hour and the solvent removed under reduced pressure. The crude solid is dissolved in dimethylformamide (10 mL) and treated with sodium methanesulfinate (4.39 g, 42.5 mmol), 18-crown-6 (580 mg, 2.13 mmol) and the mixture stirred at room temperature for 16 hours. The reaction mixture is diluted with ethyl acetate (20 mL), washed with water (20 mL) and brine (20 mL), dried over MgSO$_4$, filtered, concentrated, and the crude material purified by column chromatography on silica gel eluting with a gradient of ethyl acetate/heptane to afford the title compound (2.12 g): m/z (CI) 251 [M+H].

Step 2: Preparation of 2,2-difluoro-N-((1R,2S)-3-fluoro-1-hydroxy-1-(4-(6-(methylsulfonylmethyl)pyridin-3-yl)phenyl)propan-2-yl)acetamide

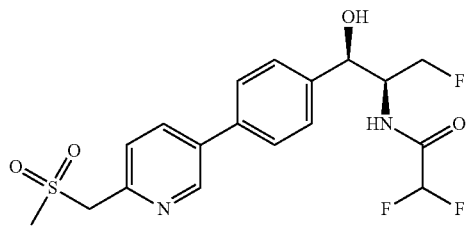 [SMILES: CS(=O)(=O)Cc1ccc(-c2ccc([C@@H](O)[C@@H](CF)NC(=O)C(F)F)cc2)cn1]

To a solution of 5-bromo-2-(methylsulfonylmethyl)pyridine (1500 mg, 3.65 mmol) in degassed N-Methyl-2-pyrrolidone (10 mL) is added 2,2-dichloro-N-((1R,2S)-3-fluoro-1-hydroxy-1-(4-(trimethylstannyl)phenyl)propan-2-yl)acetamide (1000 mg, 4.0 mmol) and tris(2-furyl)phosphine (173 mg, 0.73 mmol). Tris(dibenzylideneacetone) dipalladium (335 mg, 0.37 mmol) is added and the reaction mixture heated to 80° C. for 16 hours. The mixture is diluted with ethyl acetate, washed with water and brine, dried, filtered, concentrated, and the crude material purified by column chromatography on silica gel eluting with a gradient of ethyl acetate/heptane to afford the title compound (545 mg): $^1$H NMR (400 MHz, CDCl$_3$) δ: 3.05 (s, 3H), 4.20-4.50 (m, 2H), 4.50-4.80 (m, 3H including 2H singlet at 4.69), 4.90 (t, J=3.9 Hz, 1H), 5.91 (d, J=4.5 Hz, 1H), 6.21 (t, J=56 Hz,1H), 7.48 (d, J=8.2, 1H), 7.60 (d, J=8.2 Hz, 1H), 7.74 (d, J=8.2 Hz, 1H), 8.15 (dd, J=8.1 Hz and 2.3 Hz, 1H), 8.83 (d, J=8.6 Hz, 1H), 8.92 (d, J=1.8 Hz, 1H). m/z (CI) 417 [M+H].

Example 8

Preparation of 2,2-difluoro-N-((1R,2S)-3-fluoro-1-hydroxy-1-(4-(6-(3-hydroxyoxetan-3-yl)pyridin-3-yl)phenyl)propan-2-yl)acetamide

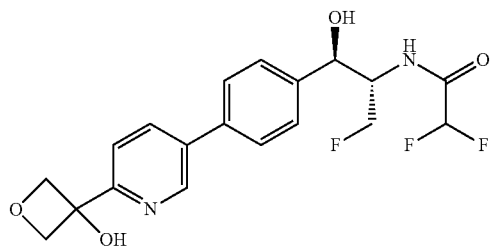 [SMILES: O=C(N[C@H](CF)[C@H](O)c1ccc(-c2ccc(C3(O)COC3)nc2)cc1)C(F)F]

Step 1: Preparation of 3-(5-Bromopyridin-2-yl)oxetan-3-ol

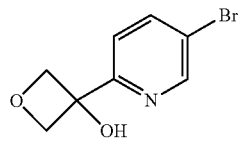 [SMILES: OC1(c2ccc(Br)cn2)COC1]

2,5-Dibromopyridine (10 g, 35.2 mmol) is dissolved in dry toluene (200 mL) under a nitrogen atmosphere and cooled to −78° C. n-Butyllithium (2.5M in hexanes, 2.5 mL, 38.7 mmol) is added at −78° C. over 20 minutes. The reaction mixture is stirred at −78° C. for 20 minutes. Oxetane-3-one (2.79 g, 38.7 mmol) in toluene (100 mL) is added then stirred at −78° C. for 30 minutes. Saturated aqueous ammonium chloride solution (50 mL) is added. The mixture extracted with ethyl acetate (2×200 mL), separated, washed with brine solution (50 mL) and the solvent evaporated under reduced pressure. The crude material is purified using flash chromatography (35% ethyl acetate in hexane) to give the title compound (4.2 g): $^1$H NMR (400 MHz, DMSO-d$_6$):δ 4.64 (2H, d), 4.87 (2H, d), 6.68 (1H, s), 7.55 (1H, d), 8.06 (1H, dd), 8.76 (1H, d).

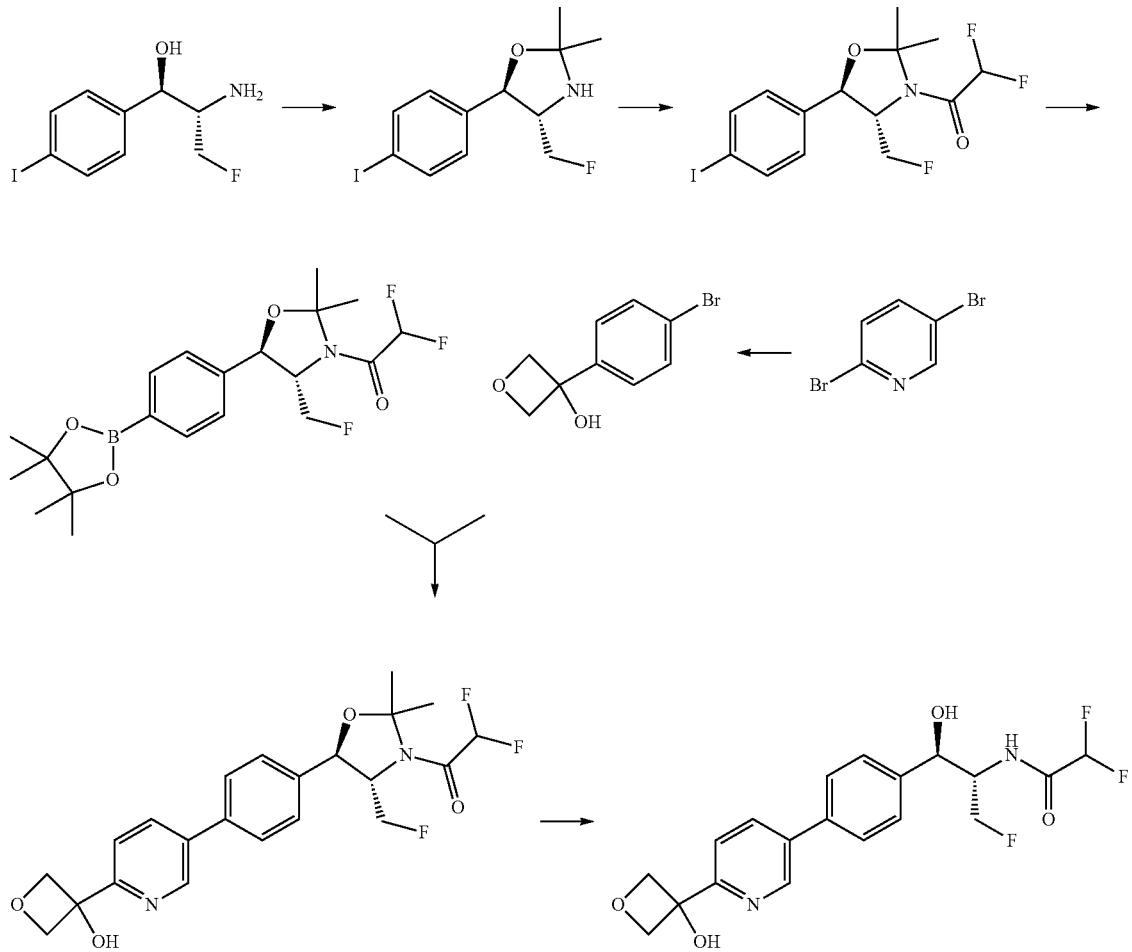

Step 2: Preparation of (4S,5R)-4-(fluoromethyl)-5-(4-iodophenyl)-2,2-dimethyloxazolidine

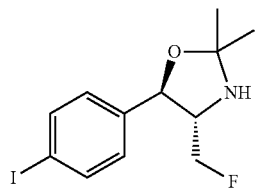 [SMILES: CC1(C)N[C@H](CF)[C@@H](c2ccc(I)cc2)O1]

Acetone (150 mL) is added to commercially available (1R,2S)-2-amino-3-fluoro-1-(4-iodophenyl)propan-1-ol (15.0 g, 50.8 mmol). After stirring overnight at room temperature the solvent is removed under reduced pressure to give the title compound (17.6 g): m/z (CI) M+H 335.

Step 3: Preparation of 2,2-difluoro-1-((4S,5R)-4-(fluoromethyl)-5-(4-iodophenyl)-2,2-dimethyloxazolidin-3-yl)ethanone

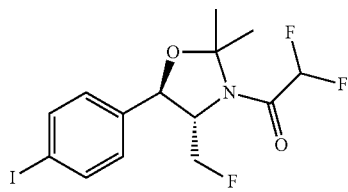 [SMILES: CC1(C)O[C@H](c2ccc(I)cc2)[C@@H](CF)N1C(=O)C(F)F]

To a stirring solution of the product of step 2—Example 8 (3.0 g, 8.9 mmol) in $CH_2Cl_2$ (50 mL) at 0° C. is added triethylamine (6.2 mL, 44.8 mmol) followed by dropwise addition of difluoroacetyl chloride (2.2 mL, 27.0 mmol). The reaction mixture is slowly allowed to warm to room temperature. After 1 hour the reaction mixture is diluted with water (75 mL) and extracted with $CH_2Cl_2$ (2×75 mL). The combined organic phase is dried over $MgSO_4$ and concentrated under vacuum. The crude material is chromatographed (80 g Redi-Sep column) eluting from 100% hexanes to 25:75 EtOAc:hexanes to afford the title compound (3.54 g): m/z (CI) M+H 413.0.

Step 4: Preparation of 2,2-difluoro-1-((4S,5R)-4-(fluoromethyl)-2,2-dimethyl-5-(4-(4,4,5,5-tetramethyl-1,3,2-dioxaborolan-2-yl)phenyl)oxazolidin-3-yl)ethanone

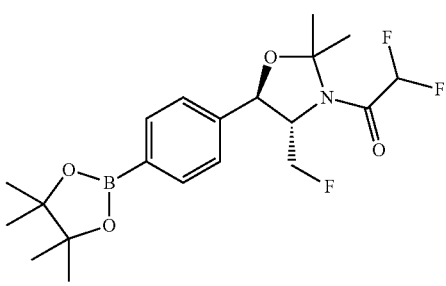 [SMILES: CC1(C)O[C@H](c2ccc(B3OC(C)(C)C(C)(C)O3)cc2)[C@@H](CF)N1C(=O)C(F)F]

To a solution of the product of step 3—Example 8 (3.5 g, 8.4 mmol) in dioxane (100 mL) is added bis(pinacolato)diboron (2.4 g, 9.3 mmol), potassium acetate (2.5 g, 25.4 mmol), and $Pd(PPh_3)_2Cl_2$ (300 mg, 0.4 mmol). The reaction is heated to 90° C. under nitrogen for 22 hours. Reaction mixture is cooled to room temperature and concentrated under vacuum to remove dioxane to a volume of ~50 mL. The residue was diluted with water (150 mL) and extracted with $CH_2Cl_2$ (2×125 mL). The combined organic phases are dried over $Na_2SO_4$ and concentrated under vacuum. The crude material is purified by chromatography (120 g Redi-Sep column) eluting from 100% hexanes to 25:75 EtOAc:hexanes to the title compound (2.06 g): m/z (CI) M+H 413.2.

Step 5: Preparation of 3-(5-{4-[(4S,5R)-3-(difluoroacetyl)-4-(fluoromethyl)-2,2-dimethyl-1,3-oxazolidin-5-yl]phenyl}pyridin-2-yl)oxetan-3-ol

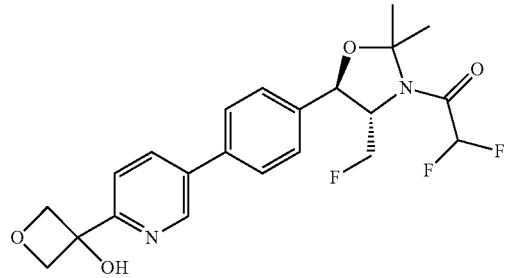 [SMILES: CC1(C)O[C@H](c2ccc(-c3ccc(C4(O)COC4)nc3)cc2)[C@@H](CF)N1C(=O)C(F)F]

A mixture of sodium carbonate (0.54 g, 5.08 mmol) dissolved in water (2.5 mL, 140 mmol) and 1,4-dioxane (6.10 mL, 78.2 mmol) is sonicated for 5 minutes then degassed with bubbling $N_2$ for 15 min. The product of step 1—Example 8 (0.300 g, 1.30 mmol) and step 4—Example 8 (0.647 g, 1.56 mmol) are added successively. After addition, [1,1'-bis(diphenylphosphino)ferrocene]dichloropalladium(II) (0.0668 g, 0.0913 mmol) is added and the reaction mixture heated at 60° C. for 2 hours before being cooled to room temperature and diluted with ethylacetate. The mixture is washed with water (20 mL), followed by brine (20 mL), dried over $MgSO_4$ and the solvent removed under reduced pressure. The crude material is purified by chromatography eluting neat heptanes to 70% ethylacetate in hexanes to give the title compound (410 mg): m/z (CI) M+H 437.

Step 6: Preparation of 2,2-Difluoro-N-((1R,2S)-3-fluoro-1-hydroxy-1-(4-(6-(3-hydroxyoxetan-3-yl)pyridin-3-yl)phenyl)propan-2-yl)acetamide

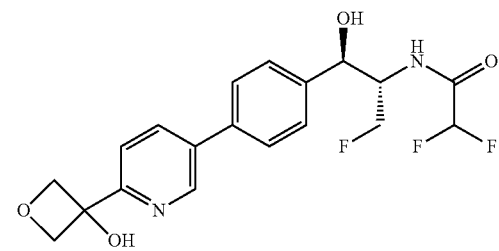 [SMILES: O=C(N[C@H](CF)[C@H](O)c1ccc(-c2ccc(C3(O)COC3)nc2)cc1)C(F)F]

Trifluoroacetic acid (0.3090 mL, 4.011 mmol) and a drop of water is added to a stirred solution of the product of step 5—Example 8 (116.7 mg, 0.2674 mmol) and methylene chloride (5.00 mL) at 0° C. and the reaction mixture is stirred at 0° C. for 10 minutes before being warmed to room temperature. After 2 hours, more trifluoroacetic acid (0.1030 mL, 1.337 mmol) is added and stirring continued for 4 hours. The reaction mixture is diluted with $CH_2Cl_2$ (10 mL), washed with saturated aqueous $NaHCO_3$ solution (10 mL), brine (10 mL), dried over magnesium sulfate and the solvent removed under reduced pressure to afford the title compound (70 mg): $^1H$ NMR (400 MHz, DMSO-$d_6$):δ 4.25-4.6 (2.5H, m), 4.65-4.75 (2.5H, m), 4.89 (1H, t), 4.95 (2H, d), 5.9 (1H, d), 6.2 (1H, t), 6.57 (1H, s), 7.47 (2H, d), 7.66 (1H, dd), 7.72 (2H, d), 8.11 (1H, dd), 8.81 (1H, d), 8.95 (1H, dd); m/z (CI) M+H 397.

Example 9

Preparation of N-((1R,2S)-1-(4-(6-(difluoro(methylsulfonyl)methyl)pyridin-3-yl)phenyl)-3-fluoro-1-hydroxypropan-2-yl)-2,2-difluoroacetamide

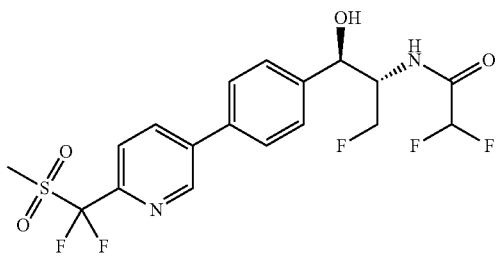 [SMILES: CS(=O)(=O)C(F)(F)c1ccc(-c2ccc([C@@H](O)[C@@H](CF)NC(=O)C(F)F)cc2)cn1]

Step 1: Preparation of 2,2-difluoro-1-((4S,5R)-4-(fluoromethyl)-2,2-dimethyl-5-(4-(6-(methylsulfonylmethyl)pyridin-3-yl)phenyl)oxazolidin-3-yl)ethanone

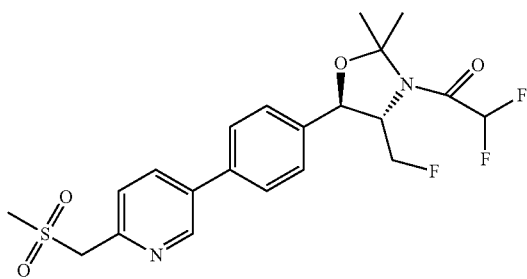 [SMILES: CC1(C)O[C@H](c2ccc(-c3ccc(CS(C)(=O)=O)nc3)cc2)[C@@H](CF)N1C(=O)C(F)F]

2,2-difluoro-1-((4S,5R)-4-(fluoromethyl)-2,2-dimethyl-5-(4-(4,4,5,5-tetramethyl-1,3,2-dioxaborolan-2-yl)phenyl)oxazolidin-3-yl)ethanone (100 mg, 0.24 mmol) in 1:1 toluene/isopropyl alcohol (4 mL) is treated with commercially available 5-bromo-2-(methylsulfonylmethyl)pyridine (60 mg, 0.24 mmol), sodium bicarbonate (1 mL of a 2M solution), and (1,1'-bis[diphenylphosphino]ferrocene)dichloropalladium (II) (10 mg, 0.012 mmol) then heated at 120° C. in a microwave for 30 minutes. The mixture is concentrated and purified by column chromatography on silica gel eluting with a gradient of ethyl acetate in heptane to give the title compound (135 mg). m/z (Cl) 457 [M+H].

Step 2: Preparation of 1-((4S,5R)-5-(4-(6-(difluoro(methylsulfonyl)methyl)pyridin-3-yl)phenyl)-4-(fluoromethyl)-2,2-dimethyloxazolidin-3-yl)-2,2-difluoroethanone

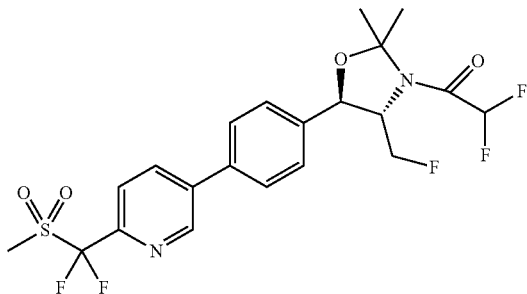 [SMILES: CC1(C)O[C@H](c2ccc(-c3ccc(C(F)(F)S(C)(=O)=O)nc3)cc2)[C@@H](CF)N1C(=O)C(F)F]

2,2-difluoro-1-((4S,5R)-4-(fluoromethyl)-2,2-dimethyl-5-(4-(6-(methylsulfonylmethyl)pyridin-3-yl)phenyl)oxazolidin-3-yl)ethanone (135 mg, 0.30 mmol) in tetrahydrofuran (6 mL) at −70° C. is treated with 1M potassium bis(trimethylsilyl)amide in tetrahydrofuran (0.89 mL, 0.89 mmol), stirred 40 minutes then added manganese bromide (128 mg, 0.59 mmol) and stirred an additional 30 minutes. N-fluorodibenzenesulfonamide (295 mg, 0.89 mmol) is added and the mixture allowed to warm to room temperature and stirred for 16 hours then diluted with ethyl acetate, washed with water and brine, dried, filtered, concentrated, and the crude material purified by column chromatography on silica gel eluting with a gradient of ethyl acetate/heptane to afford the title compound (34 mg): m/z (Cl) 493 [M+H].

Step 3: Preparation of N-((1R,2S)-1-(4-(6-(difluoro(methylsulfonyl)methyl)pyridin-3-yl)phenyl)-3-fluoro-1-hydroxypropan-2-yl)-2,2-difluoroacetamide

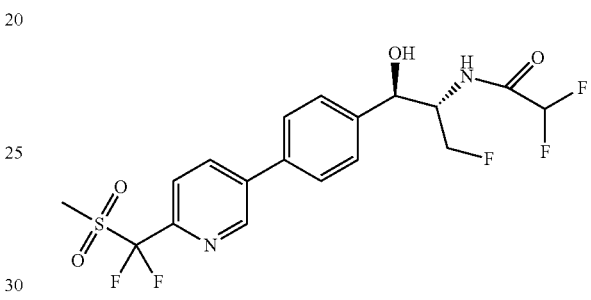

1-((4S,5R)-5-(4-(6-(difluoro(methylsulfonyl)methyl)pyridin-3-yl)phenyl)-4-(fluoromethyl)-2,2-dimethyloxazolidin-3-yl)-2,2-difluoroethanone (30 mg, 0.06 mmol) is suspended in 4N hydrochloric acid in dioxane, cooled to 5° C. then treated with 2 drops of water, stirred 30 minutes then purified by HPLC to give the title compound (13 mg). $^1$H NMR (400 MHz, DMSO-$d_6$) δ: 3.40 (s, 3H), 4.25-4.50 (m, 3H), 4.92 (m, 1H), 6.20 (t, J=56 Hz, 1H), 7.52 (d, J=8.2, 1H), 7.82 (d, J=8.2 Hz, 1H), 7.93 (d, J=8.2, 1H), 8.38 (dd, J=8.2 Hz and 2.1 Hz, 1H), 8.83 (d, J=8.6 Hz, 1H), 9.13 (d, J=1.8 Hz, 1H). m/z (Cl) 453 [M+H].

Example 10

2,2-dichloro-N-((1R,2S)-3-fluoro-1-hydroxy-1-(4-(3-(methylsulfonylmethyl)isoxazol-5-yl)phenyl)propan-2-yl)acetamide

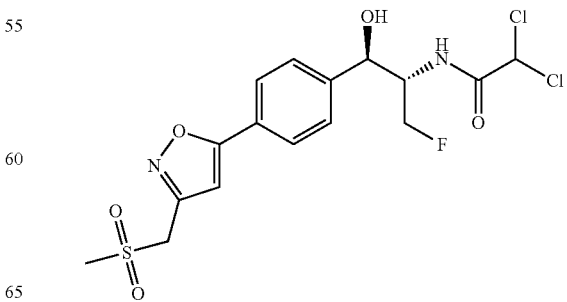

Step 1: Preparation of (4S,5R)-tert-butyl 4-(fluoromethyl)-2,2-dimethyl-5-(4-(3-((methylsulfonyloxy)methyl)isoxazol-5-yl)phenyl)oxazolidine-3-carboxylate

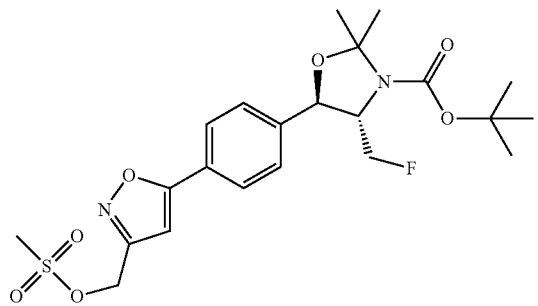 [SMILES: CC(C)(C)OC(=O)N1[C@H](CF)[C@@H](c2ccc(-c3cc(COS(C)(=O)=O)no3)cc2)OC1(C)C]

(4S,5R)-tert-butyl 4-(fluoromethyl)-5-(4-(3-(hydroxymethyl)isoxazol-5-yl)phenyl)-2,2-dimethyloxazolidine-3-carboxylate (see US2004/0082553, page 67 (page 68 of pdf version)) (1000 mg, 2.45 mmol) in CH$_2$Cl$_2$ (25 mL) at 5° C. is treated with pyridine (0.23 mL, 2.95 mmol) and methanesulfonylchloride (0.19 mL, 2.45 mmol) then stirred for 1 hour, washed with saturated aqueous sodium bicarbonate, concentrated and used as is (1130 mg). m/z (CI) 485 [M+H].

Step 2: Preparation of (4S,5R)-tert-butyl 4-(fluoromethyl)-2,2-dimethyl-5-(4-(3-(methylsulfonylmethyl)isoxazol-5-yl)phenyl)oxazolidine-3-carboxylate

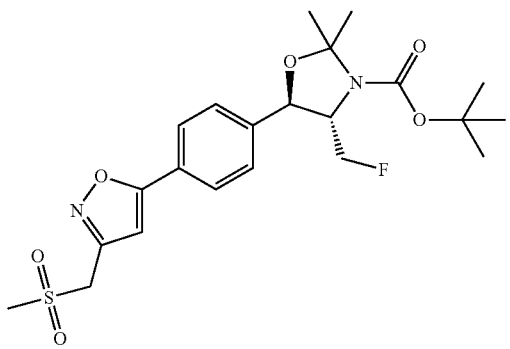 [SMILES: CC(C)(C)OC(=O)N1[C@H](CF)[C@@H](c2ccc(-c3cc(CS(C)(=O)=O)no3)cc2)OC1(C)C]

(4S,5R)-tert-butyl 4-(fluoromethyl)-2,2-dimethyl-5-(4-(3-((methylsulfonyloxy)methyl)isoxazol-5-yl)phenyl)oxazolidine-3-carboxylate (200 mg, 0.413 mmol), sodium methanesulfinate (100 mg, 0.83 mmol), and 18-crown-6 (23 mg, 0.08 mmol) in acetonitrile (8 mL) are stirred at room temperature for 16 hours then the mixture is concentrated and purified by column chromatography on silica gel eluting with a gradient of ethyl acetate/heptane to afford the title compound (150 mg). m/z (CI) 469 [M+H].

Step 3: Preparation of (1R,2S)-2-amino-3-fluoro-1-(4-(3-(methylsulfonylmethyl)isoxazol-5-yl)phenyl)propan-1-ol

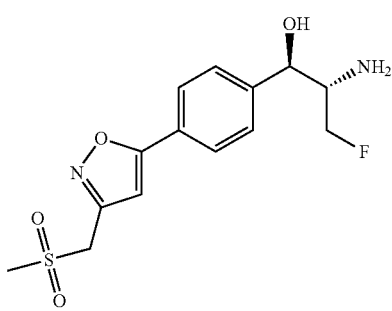 [SMILES: CS(=O)(=O)Cc1cc(-c2ccc([C@@H](O)[C@H](N)CF)cc2)on1]

The product of step 2—Example 10 (150 mg, 0.32 mmol) is added to 4N hydrochloric acid in dioxane at 5° C. then treated with 4 drops of water. The reaction mixture is stirred 30 minutes at room temperature. Acetonitrile (5 mL) is added, then the solvent removed under reduced pressure to give the title compound (150 mg). m/z (CI) 329 [M+H].

Step 4: Preparation of 2,2-dichloro-N-((1R,2S)-3-fluoro-1-hydroxy-1-(4-(3-(methylsulfonylmethyl)isoxazol-5-yl)phenyl)propan-2-yl)acetamide

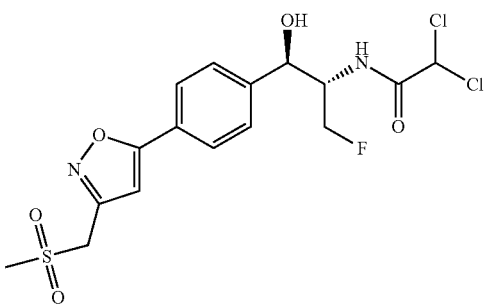 [SMILES: CS(=O)(=O)Cc1cc(-c2ccc([C@@H](O)[C@@H](CF)NC(=O)C(Cl)Cl)cc2)on1]

The product of step 3—Example 10 (75 mg, 0.21 mmol) in dimethylformamide (2 mL) at 5° C. is treated with diisopropylethylamine (0.055 mL, 0.31 mmol) and then dichloroacetylchloride (0.024 mL, 0.25 mmol) is added and the mixture stirred at room temperature for 1 hour. Water (10 mL) is added followed by ethyl acetate (10 mL) and the organics washed with brine (10 mL), dried over MgSO$_4$, filtered, concentrated and purified by HPLC to give the title compound (41 mg). $^1$H NMR (400 MHz, DMSO-d$_6$) δ: 3.10 (s, 3H), 4.20-4.50 (m, 1H), 4.55-4.80 (m, 3H including 2H singlet at 4.75), 4.94 (t, 1H), 6.07 (d, 1H), 6.49 (s, 1H), 7.07 (s, 1H), 7.52 (d, 2H), 7.85 (d, 2H), 8.60 (d, 1H. m/z (CI) 440 [M+H].

Example 11

Preparation of 2,2-difluoro-N-((1R,2S)-3-fluoro-1-hydroxy-1-(4-(3-(methylsulfonylmethyl)isoxazol-5-yl)phenyl)propan-2-yl)acetamide

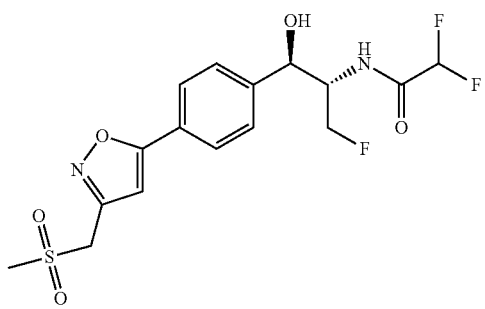 [SMILES: CS(=O)(=O)Cc1cc(-c2ccc([C@@H](O)[C@@H](CF)NC(=O)C(F)F)cc2)on1]

(1R,2S)-2-amino-3-fluoro-1-(4-(3-(methylsulfonylmethyl)isoxazol-5-yl)phenyl)propan-1-ol (75 mg, 0.21 mmol) in dimethylformamide (2 mL) at 5° C. is treated with diisopropylethylamine (0.055 mL, 0.62 mmol) and then difluoroacetylchloride (0.026 mL, 0.25 mmol) is added and the mixture stirred at room temperature for 1 hour. Water is added (10 mL) and extracted with ethyl acetate (10 mL) and the organics washed with brine (10 mL), dried over MgSO$_4$, filtered, concentrated and purified by reverse phase preparative HPLC to give the title compound (35 mg). ¹H NMR (400 MHz, DMSO-d₆) δ: 3.10 (s, 3H), 4.33 (m, 1H), 4.40-4.60 (m, 1H), 4.65-4.80 (m, 3H including 2H singlet at 4.75), 4.92 (bs, 1H), 6.17 (t, 1H), 7.08 (s, 1H), 7.51 (d, 2H), 7.86 (d, 2H), 8.80 (d, 1H); m/z (CI) 407 [M+H].

Example 12

Preparation of: N-((1R,2S)-1-(4-(3-(cyanomethyl)isoxazol-5-yl)phenyl)-3-fluoro-1-hydroxypropan-2-yl)-2,2-difluoroacetamide

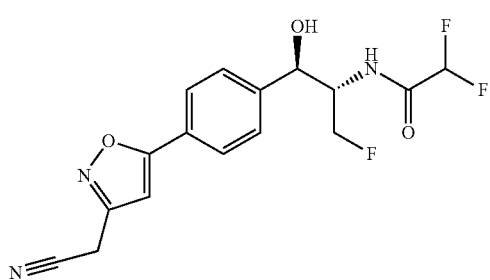 [SMILES: N#CCc1cc(-c2ccc([C@@H](O)[C@@H](CF)NC(=O)C(F)F)cc2)on1]

Step 1: Preparation of (4S,5R)-tert-butyl 5-(4-(3-(cyanomethyl)isoxazol-5-yl)phenyl)-4-(fluoromethyl)-2,2-dimethyloxazolidine-3-carboxylate

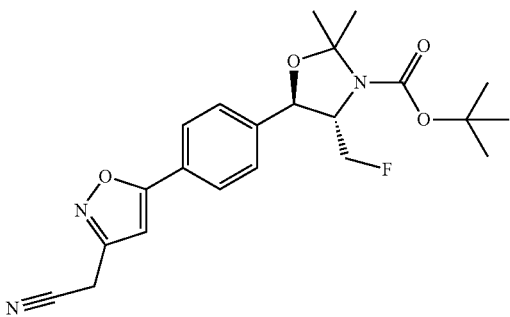 [SMILES: CC(C)(C)OC(=O)N1[C@H](CF)[C@@H](c2ccc(-c3cc(CC#N)no3)cc2)OC1(C)C]

The product of step 1 of Example 10 (200 mg, 0.41 mmol), potassium cyanide (111 mg, 1.65 mmol), and 18-crown-6 (23 mg, 0.08 mmol) in acetonitrile (8 mL) are stirred at room temperature for 16 hours then the mixture is concentrated and purified by column chromatography on silica gel eluting with a gradient of ethyl acetate/heptane to afford the title compound (95 mg). m/z (CI) 416 [M+H].

Step 2: Preparation of 2-(5-(4-((1R,2S)-2-amino-3-fluoro-1-hydroxypropyl)phenyl)isoxazol-3-yl)acetonitrile

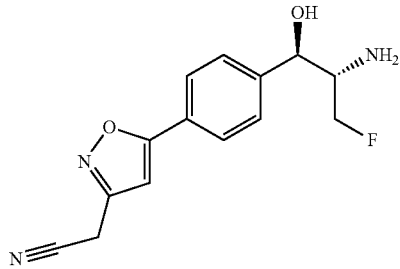 [SMILES: N#CCc1cc(-c2ccc([C@@H](O)[C@H](N)CF)cc2)on1]

The product of step 1 of Example 12 (50 mg, 0.12 mmol) in CH₂Cl₂ (2 mL) at 5° C. is treated with trifluoroacetic acid (0.5 mL), stirred 30 minutes at room temperature, diluted with toluene, and concentrated to give the title compound, which is carried on to the next step without purification m/z (CI) 276 [M+H].

Step 3: Preparation of N-((1R,2S)-1-(4-(3-(cyanomethyl)isoxazol-5-yl)phenyl)-3-fluoro-1-hydroxypropan-2-yl)-2,2-difluoroacetamide

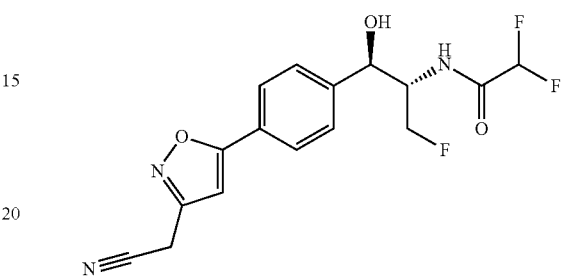

The product of Step 2—Example 12 in dimethylformamide (2 mL) at 5° C. is treated with diisopropylethylamine (0.062 mL, 0.36 mmol) and then difluoroacetylchloride (0.020 mL, 0.18 mmol) is added and the mixture stirred at room temperature for 1 hour. Water (10 mL) is added and extracted with ethyl acetate (10 mL) and the organics washed with brine(10 mL), dried, filtered, concentrated and purified by reverse phase preparative HPLC to give the title compound (35 mg). ¹H NMR (400 MHz, DMSO-d₆) δ: 3.30 (s, 3H), 4.20-4.50 (m, 4H including 2H singlet at 4.28), 4.50-4.75 (m, 1H), 4.92 (t, J=3.7 Hz, 1H), 5.98 (m, 1H), 6.17 (t, J=56 Hz, 1H), 7.08 (s, 1H), 7.51 (d, J=8.1, 2H), 7.86 (d, J=8.1 Hz, 2H.

HPLC conditions: Prep HPLC=Waters, Column=Luna C5 21×250 mm 5 um,

MP A=0.1% TFA in H2O MP B=ACN, Gradient 10% B to 100% in 19 min holding for 1 min,20 mL/min.

Example 13

Preparation of 2,2-difluoro-N-((1R,2S)-3-fluoro-1-(4-(6-((RS)-fluoro(methylsulfonyl)methyl)pyridin-3-yl)phenyl)-1-hydroxypropan-2-yl)acetamide

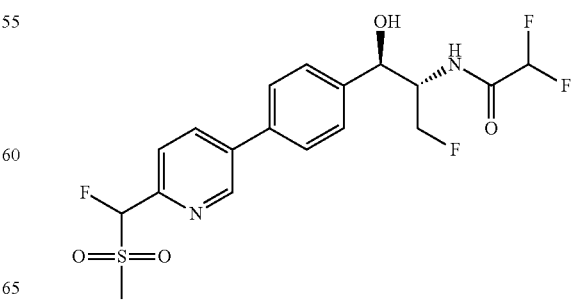

Step 1: Preparation of (±)-5-bromo-2-(fluoro(methylsulfonyl)methyl)pyridine

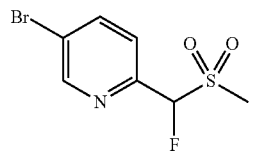

Lithium bis(trimethylsilyl)amide (0.45 mL, 1M in tetrahydrofuran, 0.45 mmol) is added to a solution of commercially available 5-bromo-2-(methylsulfonylmethyl)pyridine (102 mg, 0.408 mmol) in tetrahydrofuran (5 mL) at −78° C. After 45 minutes N-Fluorodibenzenesulfonamide (156 mg) in tetrahydrofuran (10 mL) is added to the reaction mixture at −78° C. over 5 minutes. After stirring for 20 minutes the reaction is quenched with water (10 mL) and ethyl acetate (10 mL). The reaction mixture is partitioned between saturated aqueous ammonium chloride solution (10 mL) and ethyl acetate (10 mL). The combined organic layers are washed with brine and concentrated to give the crude product, which is purified by flash column chromatography eluting from neat hexane to neat ethyl acetate to give the title compound (50 mg): m/z (Cl) 268 (M+H).

Step 2: Preparation of 2,2-difluoro-N-((1R,2S)-3-fluoro-1-hydroxy-1-(4-iodophenyl)propan-2-yl)acetamide

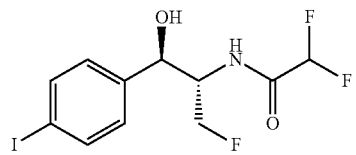 [SMILES: O=C(N[C@H](CF)[C@H](O)c1ccc(I)cc1)C(F)F]

Using the same procedure as Step 1 of Example 4 and reacting ethyldifluoroacetate with commercially available (1R,2S)-2-amino-3-fluoro-1-(4-iodophenyl)propan-1-ol the title compound is obtained (18.3 g): m/z 373 (M+H)⁺.

Step 3: Preparation of 2,2-difluoro-N-((1R,2S)-3-fluoro-1-hydroxy-1-(4-(trimethylstannyl)phenyl)propan-2-yl)acetamide

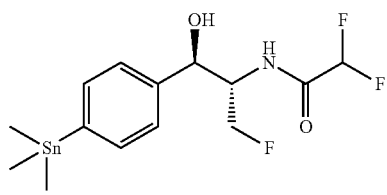 [SMILES: [CH3][Sn]([CH3])([CH3])[c]1ccc([C@@H](O)[C@@H](CF)NC(=O)C(F)F)cc1]

Using the same procedure as Step 2 of Example 4 but the product of Step 2—Example 13 the title compound is obtained (11.0 g): m/z 411.1.

Step 4: Preparation of 2,2-difluoro-N-((1R,2S)-3-fluoro-1-(4-(6-((RS)-fluoro(methylsulfonyl)methyl)pyridin-3-yl)phenyl)-1-hydroxypropan-2-yl)acetamide

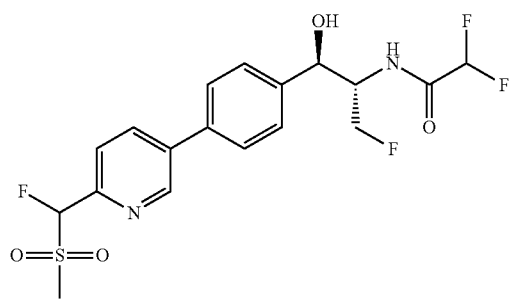 [SMILES: CS(=O)(=O)C(F)c1ccc(-c2ccc([C@@H](O)[C@@H](CF)NC(=O)C(F)F)cc2)cn1]

A mixture of the product of Step 1 of Example 13 (50 mg, 0.2 mmol), the product of Step 3 of Example 13 (76 mg, 0.2 mmol), and tris(2-furyl)phosphine (9 mg, 0.04 mmol) are dissolved in N-methyl-2-pyrrolidinone (1 mL) and de-oxygenated. Tris(dibenzylideneacetone) dipalladium (0) (18.5 mg, 0.02 mmol) is then added and the mixture is heated to 80° C. overnight. The mixture is purified by HPLC (Waters, Column=Princeton Ultima C18 30×150 mm 5 um, MP A=0.1% FA in H2O) then by SFC (TharMS100, Column=2-Ethyl Pyridine 30×250 mm 5 um, MP A=CO2) to give the title compound as a white solid (21 mg, 30%). ¹H-NMR (400 MHz, DMSO) δ:3.2 (s, 3H), 4.25-4.35 (m, 1.5H), 4.40-4.50 (m, 0.5H), 4.50-4.60 (m, 0.5H), 4.60-4.75 (m, 0.5H), 4.90 (s, 1H), 5.90-6.00 (m, 1H), 6.20 (t, 1H), 6.80 (d, 1H), 7.5 (d, 2H), 7.70 (d, 1H), 7.75 (d, 2H), 8.3 (d, 1H), 8.85 (d, 1H), 9.0 (s, 1H).

Example 14

Preparation of N-((1R,2S)-1-(4-(6-(2-amino-1,1-difluoro-2-oxoethyl)pyridin-3-yl)phenyl)-3-fluoro-1-hydroxypropan-2-yl)-2,2-difluoroacetamide

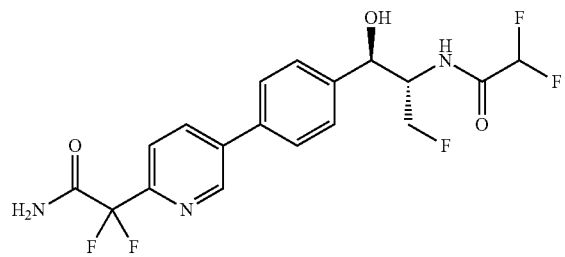 [SMILES: NC(=O)C(F)(F)c1ccc(-c2ccc([C@@H](O)[C@@H](CF)NC(=O)C(F)F)cc2)cn1]

Step 1: Preparation of 2-(5-bromopyridin-2-yl)-2,2-difluoroacetamide

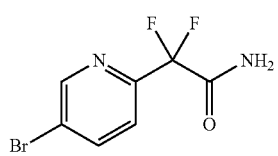 [SMILES: NC(=O)C(F)(F)c1ccc(Br)cn1]

tert-Butyl-2-(5-bromopyridin-2-yl)-2,2-difluoroacetate (300 mg, 0.974 mmol) is dissolved in 7M ammonia in methanol (5 mL) and the mixture is stirred at ambient temperature for 3 days. The mixture is evaporated to dryness to give the title (240 mg). $^1$H-NMR (400 MHz, DMSO-d$_6$) 7.70 (d, 1H), 8.05 (bs, 1H), 8.3 (d, 1H), 8.40 (bs, 1H), 8.85 (s, 1H). m/z (Cl) 251+253 (M+H).

Step 2: Preparation of N-((1R,2S)-1-(4-(6-(2-amino-1,1-difluoro-2-oxoethyl)pyridin-3-yl)phenyl)-3-fluoro-1-hydroxypropan-2-yl)-2,2-difluoroacetamide

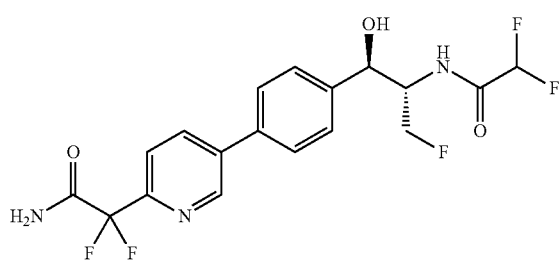

A mixture of the product of Step 1 of Example 14 (240 mg, 0.96 mmol), the product of Step 3 of Example 13 (392 mg, 0.96 mmol), and tris(2-furyl)phosphine(47 mg, 0.20 mmol) are dissolved in N-methyl-2-pyrrolidinone (1 mL) and degassed under nitrogen. Tris(dibenzylideneacetone) dipalladium (93.4 mg, 0.10 mmol) is then added and the mixture is heated to 80° C. for 16 hours. The mixture is poured into thyl acetate (15 mL) and water (10 mL) and the organic layer separated, filtered through silica and evaporated the crude product, which is purified by chromatography on a 40 g column (50-100% Ethyl acetate in heptane) to give the title compound (120 mg): $^1$H NMR (400 MHz, DMSO-d$_6$) δ:4.25-4.35 (m, 1.5H), 4.40-4.50 (m, 0.5H), 4.50-4.60 (m, 0.5H), 4.60-4.70 (m, 0.5H), 4.90 (t, 1H), 5.90 (d, 1H), 6.20 (t, 1H), 7.5 (d, 2H), 7.75 (d, 2H), 7.80 (d, 1H), 8.10 (bs, 1H), 8.30 (dd, 1H), 8.35 (bs, 1H), 8.85 (d, 1H), 9.0 (s, 1H).

Example 15

Preparation of N-((1R,2S)-1-(4-(6-(cyanomethyl)pyridin-3-yl)phenyl)-3-fluoro-1-hydroxypropan-2-yl)-2,2-difluoroacetamide

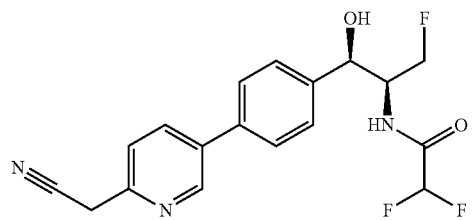 [SMILES: N#CCc1ccc(-c2ccc([C@@H](O)[C@@H](CF)NC(=O)C(F)F)cc2)cn1]

Step 1: Preparation of 2-(5-(4-((4S,5R)-3-(2,2-difluoroacetyl)-4-(fluoromethyl)-2,2-dimethyloxazolidin-5-yl)phenyl)pyridin-2-yl)acetonitrile

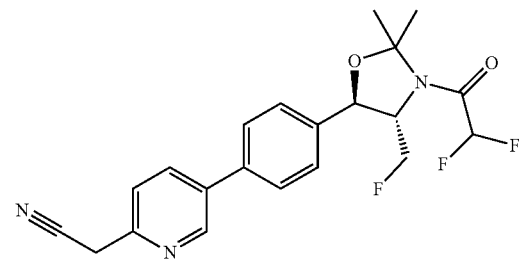 [SMILES: CC1(C)O[C@H](c2ccc(-c3ccc(CC#N)nc3)cc2)[C@@H](CF)N1C(=O)C(F)F]

Using the same procedure of Step 5 of Example 8 and making non-critical variations by reacting the product of step 4—Example 8 with commercially available 2-(5-bromopyridin-2-yl)acetonitrile the title compound is obtained (544 mg): m/z 403 (M+H)$^+$.

Step 2: Preparation of N-((1R,2S)-1-(4-(6-(cyanomethyl)pyridin-3-yl)phenyl)-3-fluoro-1-hydroxypropan-2-yl)-2,2-difluoroacetamide

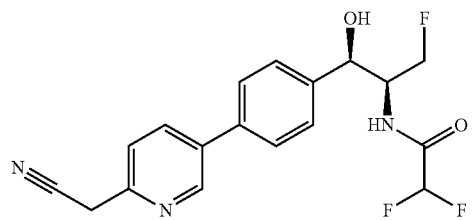 [SMILES: N#CCc1ccc(-c2ccc([C@@H](O)[C@@H](CF)NC(=O)C(F)F)cc2)cn1]

The product of Step 6 of Example 8 and the product of Step 1 of Example 15 are reacted using the same procedure as step 6—Example 8 and making non-critical variations the title compound is obtained (358 mg): $^1$H NMR (DMSO-d$_6$) 4.27 (2H, s), 4.47-4.32 (2H, m), 4.70-4.56 (1H, m), 4.91 (1H, s), 5.92 (1H, d), 6.23 (1H, t), 7.50 (3H, m), 7.74 (2H, d), 8.15 (1H, d), 8.84 (1H, d), 8.91 (1H, s); m/z 363.1 (M+H)$^+$.

Example 16

Preparation of 2,2-difluoro-N-((1R,2S)-3-fluoro-1-(4-(6-(((fluoromethyl)sulfonyl)methyl)pyridin-3-yl)phenyl)-1-hydroxypropan-2-yl)acetamide

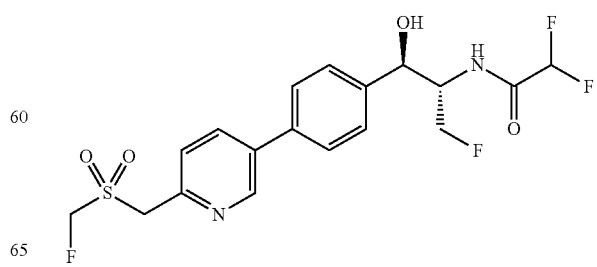

Step 1: Preparation of 5-bromo-2-(((fluoromethyl)sulfonyl)methyl)pyridine

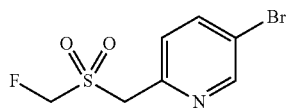 [SMILES: O=S(=O)(CF)Cc1ccc(Br)cn1]

Commercially available fluoromethanesulfonyl chloride (975 mg, 7.36 mmol) is added dropwise to a solution of sodium sulfite (1.85 g, 14.7 mmol) and sodium bicarbonate (1.24 g, 14.7 mmol) in water (2 mL). The reaction mixture is heated in a microwave reactor to 100° C. for 20 minutes. After cooling to room temperature commercially available 5-bromo-2-(chloromethyl)pyridine (894 mg, 3.68 mmol) in ethanol (2 mL) is added. The mixture is heated in a microwave reactor to 100° C. for 20 minutes. The reaction mixture is cooled to 0° C. and the solid filtered off and discarded. The filtrates are diluted with saturated sodium carbonate (10 mL), extracted with tertiarybutyl methyl ether (50 mL). The organic layer is separated, dried over sodium sulfate, filtered and the solvent removed under reduced pressure to give the title compound (150 mg): m/z 268.9 (M+H)$^+$.

Step 2: Preparation of 2,2-difluoro-1-((4S,5R)-4-(fluoromethyl)-5-(4-(6-(((fluoromethyl)sulfonyl)methyl)pyridin-3-yl)phenyl)-2,2-dimethyloxazolidin-3-yl)ethanone

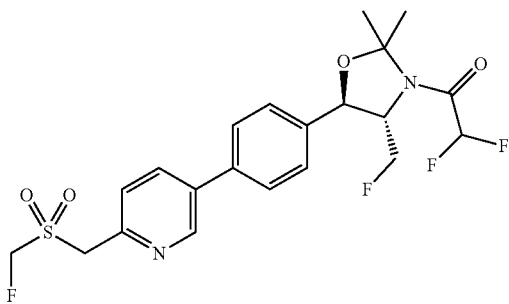 [SMILES: CC1(C)O[C@H](c2ccc(-c3ccc(CS(=O)(=O)CF)nc3)cc2)[C@@H](CF)N1C(=O)C(F)F]

Using the same procedure of step 5—Example 8 and making non-critical variations by reacting the product of step 4—Example 8 with the product of step 1—Example 16 the title compound is obtained (200 mg): m/z 474.1 (M+H)$^+$.

Step 3: Preparation of 2,2-difluoro-N-((1R,2S)-3-fluoro-1-(4-(6-(((fluoromethyl)sulfonyl)methyl)pyridin-3-yl)phenyl)-1-hydroxypropan-2-yl)acetamide

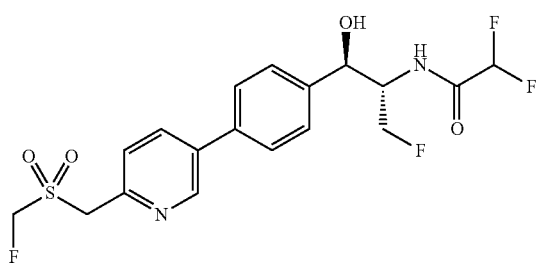 [SMILES: O=C(N[C@H](CF)[C@H](O)c1ccc(-c2ccc(CS(=O)(=O)CF)nc2)cc1)C(F)F]

Using the same procedure of step 6—Example 8, making non-critical variations and reacting the product of step 2—Example 16 the title compound is obtained (415 mg): m/z 434.1 (M+H)$^+$.

Example 17

Preparation of 2,2-dichloro-N-[(1S,2R)-1-(fluoromethyl)-2-{4-[6-(3-fluorooxetan-3-yl)pyridin-3-yl]phenyl}-2-hydroxyethyl]acetamide

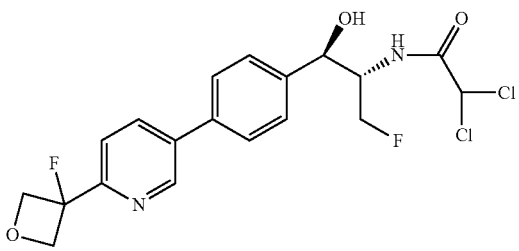 [SMILES: O=C(N[C@H](CF)[C@H](O)c1ccc(-c2ccc(C3(F)COC3)nc2)cc1)C(Cl)Cl]

Step 1: Preparation of 5-bromo-2-(3-fluorooxetan-3-yl)pyridine

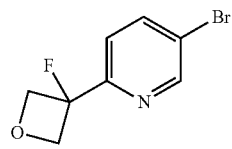 [SMILES: FC1(c2ccc(Br)cn2)COC1]

A solution of the product of Step 1, Example 8 (300.0 mg, 1.30 mmol) in methylene chloride (3.00 mL) is added to a mixture of triethylamine trishydrofluoride (0.531 mL, 3.26 mmol), triethylamine (0.273 mL, 1.96 mmol), and (Diethylamino)difluorosulfonium tetrafluoroborate (597 mg, 2.61 mmol) in methylene chloride (20.0 mL) at −78° C. The reaction mixture is slowly allowed to warm to 0° C. More (Diethylamino)difluorosulfonium tetrafluoroborate (100.0 mg, 0.437 mmol) is added and stirring continued at this temperature for 1 hour. The mixture is diluted with methylene chloride, washed with saturated sodium hydrogen carbonate solution, brine, dried over magnesium sulfate, and then concentrated. The residue is purified by chromatography on silica gel eluting with a gradient of 0-30% ethyl acetate to afford the title compound (200 mg): MS (ESI+) m/z 232.1/234.1 [M+H].

Step 2: Preparation of 5-{4-[(4S,5R)-3-(dichloroacetyl)-4-(fluoromethyl)-2,2-dimethyl-1,3-oxazolidin-5-yl]phenyl}-2-(3-fluorooxetan-3-yl)pyridine

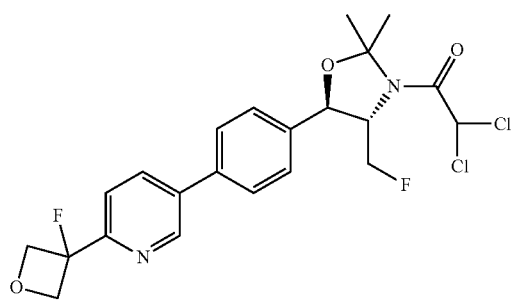 [SMILES: CC1(C)O[C@H](c2ccc(-c3ccc(C4(F)COC4)nc3)cc2)[C@@H](CF)N1C(=O)C(Cl)Cl]

To a degassed solution of the product of step 1, Example 17 (300.0 mg, 1.29 mmol), bis(pinacolato)diboron (354 mg, 1.39 mmol), and potassium acetate (342 mg, 3.48 mmol) in 1,4-dioxane (4.65 mL) is added [1,1'-Bis(diphenylphosphino)ferrocene]dichloropalladium(II) complex with dichloromethane (1:1) (81.2 mg, 0.099 mmol) and the reaction mixture is heated at 80-90° C. After 3 hours (4S,5R)-3-(dichloroacetyl)-4-(fluoromethyl)-5-(4-iodophenyl)-2,2-dimethyl-1,3-oxazolidine (see WO2013057619, 444 mg, 0.994 mmol) is added to the reaction mixture followed by a degassed solution of sodium carbonate (422 mg, 3.98 mmol) in water (2.5 mL). The reaction mixture is heated at 80-90° C. for 4 hours before being cooled to room temperature, diluted with ethyl acetate, and washed with water, then brine, dried, and concentrated. The residue is purified by chromatography on silica gel eluting with a gradient of 0-30% EtOAc in hexanes to afford the title compound (380 mg): MS (ESI+) m/z of 471.1/473.0 [M+H].

Step 3: Preparation of 2,2-dichloro-N-[(1S,2R)-1-(fluoromethyl)-2-{4-[6-(3-fluorooxetan-3-yl)pyridin-3-yl]phenyl}-2-hydroxyethyl]acetamide Trifluoroacetic acid (0.932 mL, 12.1 mmol) and a drop of water is added to a stirred solution of the product of step 2, Example 17 (380.0 mg, 0.806 mmol) in methylene chloride (5.0 mL) at 0° C. and the reaction mixture is stirred at this temperature for 10 minutes before being warmed to room temperature. After 4 hours, the solution is concentrated then diluted with methylene chloride at 0° C., quenched with saturated sodium hydrogen carbonate solution, and the aqueous layer extracted with methylene chloride. The combined organic layers were washed with brine, dried, and concentrated. The title compound is obtained (55.1 mg): $^1$H NMR (300 MHz, DMSO) δ 4.21-4.32 (m, 2.5 H), 4.42-4.47 (m, 0.5 H), 4.54-4.59 (m, 0.5 H), 4.70-4.75 (m, 0.5 H), 4.88-4.99 (m, 3H), 5.03-5.14 (m, 2H), 6.00 (d, 1H), 6.53 (s, 1H), 7.50 (d, 2H), 7.63 (d, 1H), 7.74 (d, 2H), 8.17-8.20 (dd, 1H), 8.62 (d, 1H), 8.99-9.03 (m, 1H). MS (ESI+) m/z 431.1, 433.0, and 435.0 [M+H].

Example 18

Preparation of N-((1R,2S)-1-(4-(6-(1,1-dioxidothietan-3-yl)pyridin-3-yl)phenyl)-3-fluoro-1-hydroxypropan-2-yl)-2,2-difluoroacetamide

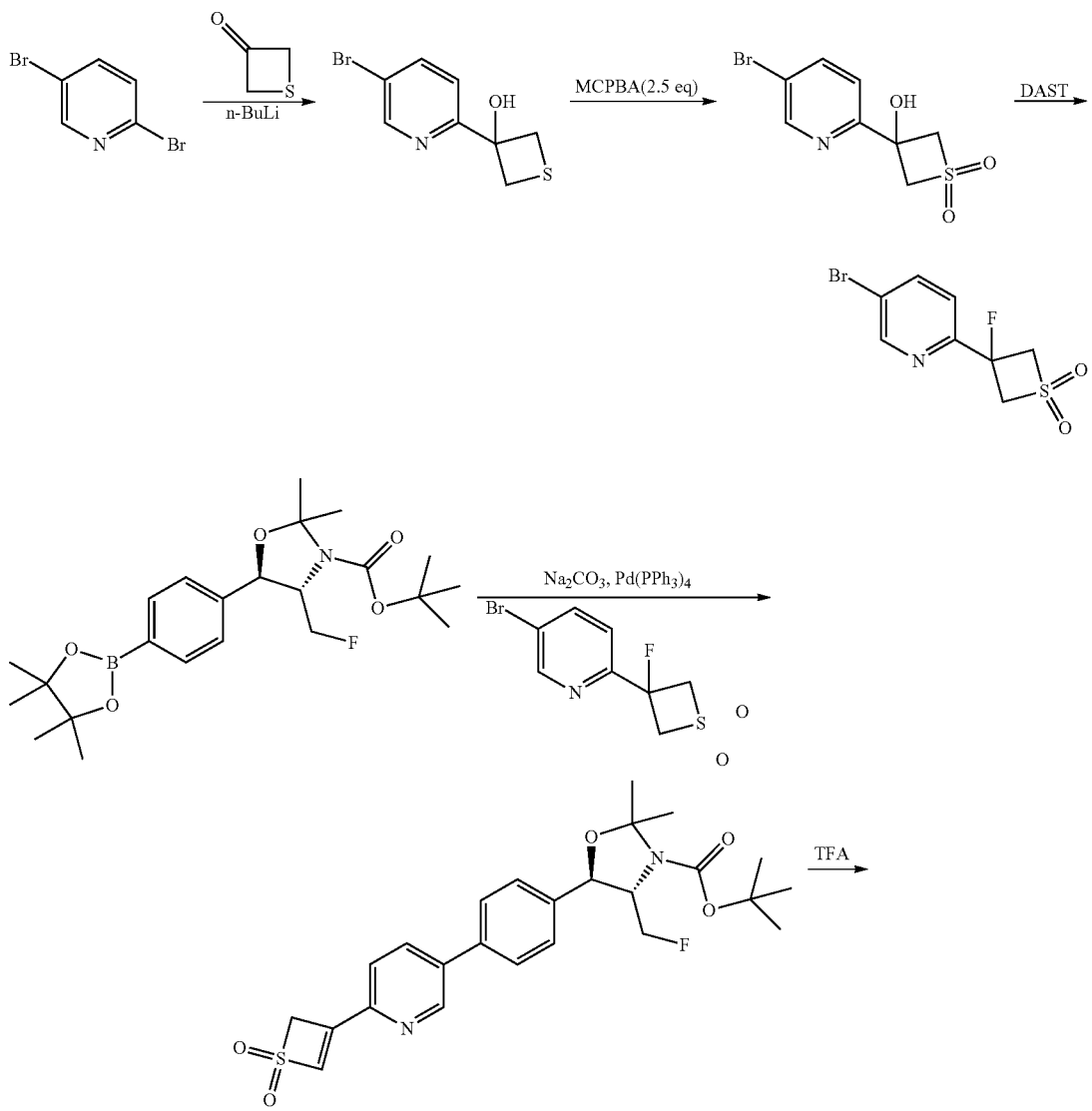

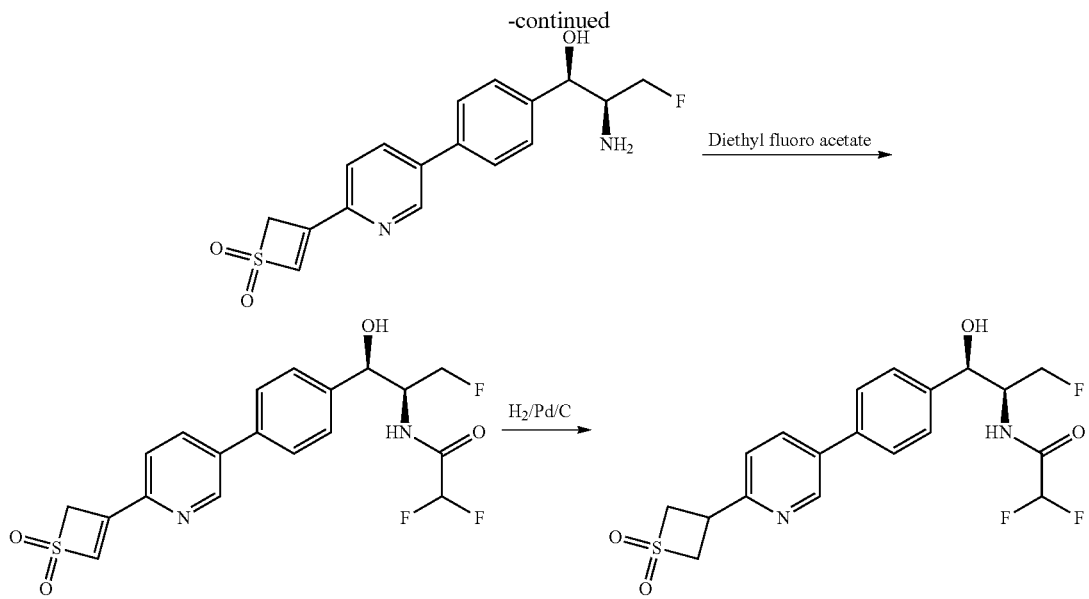

Step 1: Preparation 3-(5-bromopyridin-2-yl)thietan-3-ol

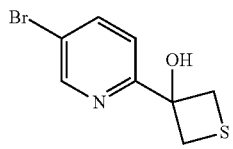

To a stirred solution of commercially available 2,5-Dibromo-pyridine (1 g, 4.219 mmol, 1 eq) in toluene (70 mL) is added 2.5 M solution of n-butyl lithium in hexane (2 mL, 5 mmol, 1.2 eq.) at −78° C. The reaction mixture is stirred for 0.5 hours at −78° C. and then is added pre-dissolved solution of commercially available thietan-3-one (0.408 g, 4.641 mmol, 1.1 eq) in toluene (5 mL). Reaction mixture is stirred at −78° C. for 2 hours, quenched with aqueous ammonium chloride solution (10 mL) and extracted with ethyl acetate (3×50 mL). Combined organic layer dried over sodium sulphate and concentrated in vacuo, the crude material is purified by column chromatography using (100-200 mesh silica). Desired compound is eluted with 12% ethyl acetate in hexane to afford title compound (0.51 g): $^1$H-NMR (400 MHz, DMSO) δ: 3.41 (d, 2H, J=9.8 Hz), 3.69 (d, 2H, J=9.92 Hz), 6.61 (s, 1H), 7.58 (d, 1H, J=8.48 Hz), 8.06-8.09 (dd, 1H, $J_1$=8.48 Hz, $J_2$=2.36 Hz), 8.72 (d, 1H, J=2.24 Hz). LC-MS (m/z): [M+H] 248.3.

Step 2: Preparation of 3-(5-bromopyridin-2-yl)-3-hydroxythietane1,1-dioxide

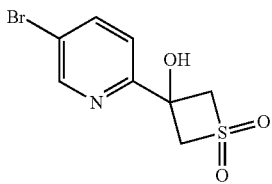 [SMILES: O=S1(=O)CC(O)(c2ccc(Br)cn2)C1]

To a solution of the product of Step 1, Example 18 (0.51 g, 2.073 mmol, 1 eq) in methylene chloride (10 mL) is added meta-chloroperoxybenzoic acid (0.895 g, 5.183 mmol, 2.5 eq.). The resulting reaction mixture is stirred at room temperature for 2 hours. The reaction mixture is quenched with water (15 mL) and extracted with methylene chloride (3×25 mL). Combined organic layer dried over sodium sulphate and concentrated in vacuo to afford title compound (0.5 g): $^1$H NMR (400 MHz, DMSO) δ: 4.24-4.28 (m, 2H), 4.72-4.75 (m, 2H), 7.1 (bs, 1H), 7.66 (d, 1H, J=8.44 Hz), 8.12-8.15 (dd, 1H, $J_1$=8.44 Hz, $J_2$=2.32 Hz), 8.77 (d, 1H, J=2.16 Hz). LC-MS (m/z): [M−H] 277.9

Step 3: Preparation of 3-(5-bromopyridin-2-yl)-3-fluorothietane 1,1-dioxide

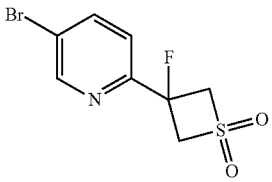

To a stirred solution of the product of step 2, Example 18 (0.3 g, 1.097 mmol, 1 eq) in methylene chloride (30 mL) is added diethylaminosulfur trifluoride (0.175 mL, 1.295 mmol, 1.1 eq) at −78° C. Resulting reaction mixture is stirred at −78° C. for 1 hour. The reaction mixture is quenched with aqueous bicarbonate solution (15 mL) and extracted with methylene chloride (3×20 mL). Combined organic layer dried over sodium sulphate and concentrated in vacuo. The crude compound is purified by column chromatography using (100-200 mesh silica). Desired compound is eluted in 10% ethyl acetate/hexane to afford title compound (0.15 g): $^1$H NMR (400 MHz, DMSO) δ: 4.77-4.86 (m, 2H), 4.94-5.05 (m, 2H), 7.62 (d, 1H, J=8.4 Hz), 8.21-8.24 (dd, 1H, $J_1$=8.44 Hz, $J_2$=2.12 Hz), 8.85 (s, 1H). LC-MS (m/z): [M+H] 281.9.

Step 4: Preparation of (4S,5R)-tert-butyl 5-(4-(6-(1,1-dioxido-2H-thiet-3-yl)pyridin-3-yl)phenyl)-4-(fluoromethyl)-2,2-dimethyloxazolidine-3-carboxylate

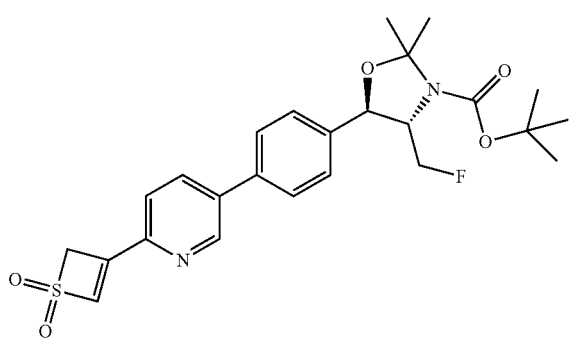 [SMILES: CC(C)(C)OC(=O)N1[C@H](CF)[C@@H](c2ccc(-c3ccc(C4=CS(=O)(=O)C4)nc3)cc2)OC1(C)C]

The solution of the product of step 3, Example 18 (0.15 g, 0.538 mmol, 1 eq), (4S,5R)-4-Fluoromethyl-2,2-dimethyl-5-[4-(4,4,5,5-tetramethyl-[1,3,2]dioxaborolan-2-yl)-phenyl]-oxazolidine-3-carboxylic acid tert-butyl ester (previously described in US2004082553, Example 20, intermediate 19, 0.234 g, 0.538 mmol, 1 eq) and sodium carbonate (0.171 g, 1.613 mmol, 3 eq) in mixture of Toluene/Ethanol/Water (1:1:0.5, 2.5 mL) is degassed with nitrogen for 30 minutes in sealed tube. To the resulting reaction mixture tetrakis(triphenylphosphine)palladium(0) (0.062 g, 0.054 mmol, 0.1 eq) is added. Resulting reaction mixture is heated at 80° C. for 6 hours. The reaction mixture is quenched with water (15 mL) and extracted with ethyl acetate (3×25 mL). Combined organic layer is dried over sodium sulphate and concentrated in vacuo. The crude compound is purified by column chromatography using (100-200 mesh silica). Desired compound is eluted with 30% ethyl acetate in hexane to afford title compound as yellow solid (0.16 g): $^1$H-NMR (400 MHz, DMSO) δ: 1.43 (bs, 9H), 1.51 (s, 3H), 1.64 (s, 3H), 3.85-3.90 (m, 1H), 4.47-4.59 (m, 1H), 4.75-4.84 (m, 1H), 5.05 (s, 2H), 5.15 (d, 1H, J=7.16 Hz), 7.62 (d, 2H, J=8.12 Hz), 7.76 (s, 1H), 7.87 (d, 2H, J=8.2 Hz), 7.93 (d, 1H, J=8.12 Hz), 8.31-8.34 (dd, 1H, $J_1$=8.24 Hz, $J_2$=2.16 Hz). 9.07 (d, 1H, J=1.88 Hz). LC-MS (m/z): [M+H] 489.1.

Step 5: Preparation of 3-(5-(4-((1R,2S)-2-amino-3-fluoro-1-hydroxypropyl)phenyl)pyridin-2-yl)-2H-thiete 1,1-dioxide

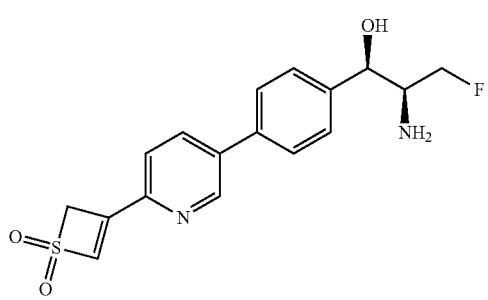 [SMILES: N[C@H](CF)[C@H](O)c1ccc(-c2ccc(C3=CS(=O)(=O)C3)nc2)cc1]

To a stirred solution of the product of step 4, Example 18 (0.15 g, 0.233 mmol, 1 eq) in methylene chloride (5 mL) is added trifluoroacetic acid (0.4 mL) at 0° C. Resulting reaction mixture is stirred at room temperature for 2 hours. The reaction mixture is concentrated in vacuo and stripped with methylene chloride (3×10 mL) to afford crude TFA salt of title compound (0.185 g), which is used as such in next step. LCMS (m/z): [M+H] 349.1.

Step 6: Preparation of N-((1R,2S)-1-(4-(6-(1,1-dioxido-2H-thiet-3-yl)pyridin-3-yl)phenyl)-3-fluoro-1-hydroxypropan-2-yl)-2,2-difluoroacetamide

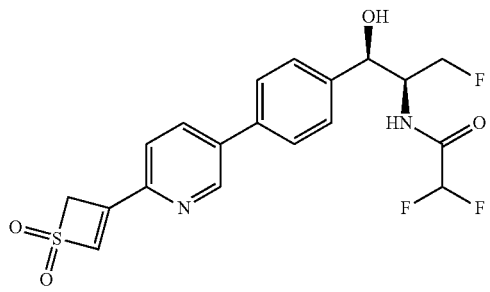 [SMILES: O=C(N[C@H](CF)[C@H](O)c1ccc(-c2ccc(C3=CS(=O)(=O)C3)nc2)cc1)C(F)F]

To a solution of the product of step 5, Example 18 (TFA salt, 0.185 g, 0.384 mmol, 1 eq) in methol (5 mL) is added triethylamine (0.135 mL, 0.96 mmol, 2.5 eq) followed by difluoro ethyl acetate (0.057 mL, 0.461 mmol, 1.2 eq) at 0° C. Resulting reaction mixture is stirred at room temperature for 16 hours. The reaction mixture is concentrated in vacuo. The crude compound is purified by column chromatography on silica gel (100-200 mesh). Desired compound is eluted in 30% ethyl acetate in hexane to afford title compound (0.053 g): $^1$H-NMR (400 MHz, DMSO) δ: 4.31-4.34 (m, 1.5H), 4.41-4.45 (m, 0.5H), 4.55-4.56 (m, 0.5H), 4.66-4.69 (m, 0.5H), 4.90 (bs, 1H), 5.05 (s, 2H), 5.96 (d, 1H, J=3.52 Hz), 6.07-6.33 (m, 1H), 7.5 (d, 2H, J=7.88 Hz), 7.75 (s, 1H), 7.82 (d, 2H, J=7.92 Hz), 7.91 (d, 1H, J=8.12 Hz), 8.32 (d, 1H, J=6.76 Hz), 8.86 (d, 1H, J=8.44 Hz), 9.07 (s, 1H). LCMS (m/z): [M−H] 425.2.

Step 7: Preparation of N-((1R,2S)-1-(4-(6-(1,1-dioxidothietan-3-yl)pyridin-3-yl)phenyl)-3-fluoro-1-hydroxypropan-2-yl)-2,2-difluoroacetamide To a stirred solution of the product of step 6, Example 18 (0.042 g, 0.099 mmol, 1 eq) in ethanol (10 mL) is added palladium on carbon (0.010 g, 10% w/w). Resulting reaction mixture is stirred at room temperature for 16 hours. After completion of the reaction, reaction mixture is filtered through celite bed and filtrate is concentrated in vacuo. The crude compound is purified by preparative TLC using 50% ethyl acetate in hexane to afford desired compound (0.010 g) which is washed with n-pentane (3×5 mL) and dried to afford title compound (0.006 g): $^1$H-NMR (400 MHz, DMSO) δ: 4.03-4.07 (m, 1H), 4.29-4.31 (m, 2H), 4.45-4.57 (m, 5H), 4.64-4.68 (m, 1H), 4.88-4.90 (m, 1H), 5.92 (d, 1H, J=4.16 Hz), 6.20 (t, 1H, J=53.72 Hz), 7.46 (d, 2H, J=8.28 Hz), 7.53 (d, 1H, J=8.08 Hz), 7.71 (d, 2H, J=8.4 Hz), 8.08-8.11 (dd, 1H, $J_1$=8.2 Hz, $J_2$=2.4 Hz), 8.86 (d, 1H, J=8.64 Hz). 8.93 (d, 1H, J=2.36 Hz). LCMS (m/z): [M+H] 428.9.

Example 19

Preparation of 2,2-dichloro-N-[(1S,2R)-1-(fluoromethyl)-2-{4-[6-(3-hydroxyoxetan-3-yl)pyridin-3-yl]phenyl}-2-hydroxyethyl]acetamide.

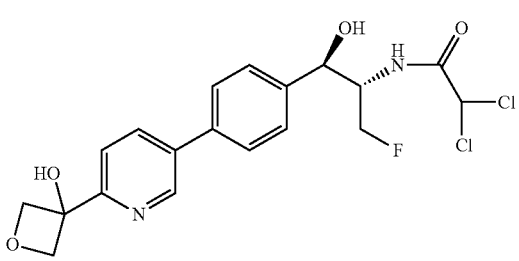

Step 1: Preparation of 3-(5-{4-[(4S,5R)-3-(dichloroacetyl)-4-(fluoromethyl)-2,2-dimethyl-1,3-oxazolidin-5-yl]phenyl}pyridin-2-yl)oxetan-3-ol

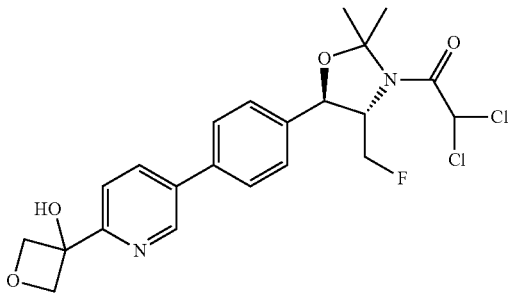 [SMILES: CC1(C)O[C@H](c2ccc(-c3ccc(C4(O)COC4)nc3)cc2)[C@@H](CF)N1C(=O)C(Cl)Cl]

Following the general procedure of step 2, Example 17 and making non-critical variations but using the product of step 1, Example 8 (370 mg, 1.61 mmol) the title compound is obtained (229 mg): MS (ESI+) m/z 469.1/471.1/473.1 [M+H].

Step 2: Preparation of 2,2-dichloro-N-[(1S,2R)-1-(fluoromethyl)-2-{4-[6-(3-fluorooxetan-3-yl)pyridin-3-yl]phenyl}-2-hydroxyethyl]acetamide Following the general procedure of step 3, Example 17 and making non-critical variations but using the product of step 1, Example 19 (217 mg, 0.462 mmol) the title compound is obtained (167 mg): $^1$H NMR (300 MHz, DMSO) δ 4.20-4.32 (m, 1.5 H), 4.42-4.47 (m, 0.5 H), 4.54-4.59 (m, 0.5 H), 4.70-4.75 (m, 0.5H), 4.88-4.99 (m, 3H), 5.03-5.14 (m, 2H), 6.00 (d, 1H), 6.53 (s, 1H), 7.50 (d, 2H), 7.63 (d, 1H), 7.74 (d, 2H), 8.17-8.20 (dd, 1H), 8.62 (d, 1H), 9.01-9.03 (m, 1H). MS (ESI+) m/z 469.1/471.1/473.1 [M+H].

Example 20

Preparation of 2,2-dichloro-N-[(1S,2R)-2-{4-[1-(cyanomethyl)-2-oxo-1,2-dihydropyridin-4-yl]phenyl}-1-(fluoromethyl)-2-hydroxyethyl]acetamide

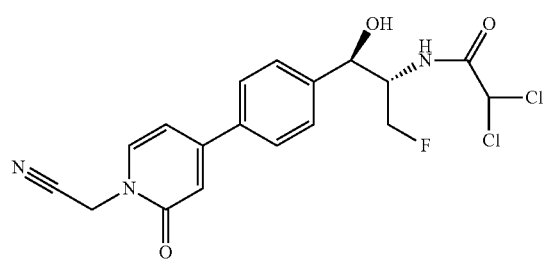 [SMILES: N#CCn1ccc(-c2ccc([C@@H](O)[C@@H](CF)NC(=O)C(Cl)Cl)cc2)cc1=O]

Step 1: Preparation of 4-{4-[(4S,5R)-3-(dichloroacetyl)-4-(fluoromethyl)-2,2-dimethyl-1,3-oxazolidin-5-yl]phenyl}pyridin-2(1H)-one

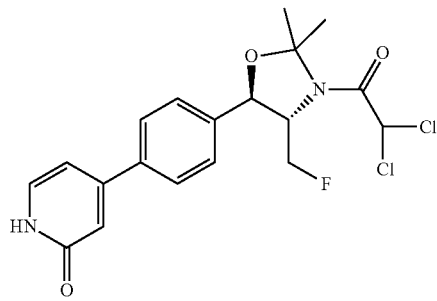 [SMILES: CC1(C)O[C@H](c2ccc(-c3cc[nH]c(=O)c3)cc2)[C@@H](CF)N1C(=O)C(Cl)Cl]

Following the general procedure of step 3, Example 4 and making non-critical variations but using 4-bromopyridin-2(1H)-one (135 mg) and the product of step 2, Example 4 (375 mg), the title compound is obtained (200 mg): MS (ESI+) m/z 413 [M+H].

Step 2: Preparation of 2,2-dichloro-N-{(1S,2R)-1-(fluoromethyl)-2-hydroxy-2-[4-(2-oxo-1,2-dihydropyridin-4-yl)phenyl]ethyl}acetamide

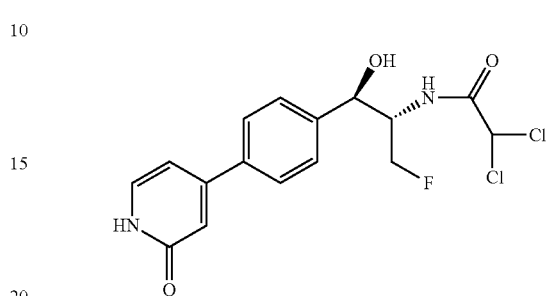

Following the general procedure of step 6, Example 8 and making non-critical variations but using the product of step 1, Example 20 (327 mg) and 25% 2,2,2-trifluoroethanol in methylene chloride (4×25 mL) in the extractive workup, the title compound is obtained (253 mg): MS (ESI+) m/z 373 [M+H].

Step 3: Preparation of 2,2-dichloro-N-[(1S,2R)-2-{4-[1-(cyanomethyl)-2-oxo-1,2-dihydropyridin-4-yl]phenyl}-1-(fluoromethyl)-2-hydroxyethyl]acetamide A microwave tube is charged with the product of step 2, Example 20 (185 mg, 0.496 mmol) in dimethylformamide (4.9 mL), cesium carbonate (194 mg, 0.595 mmol) and chloroacetonitrile (313.7 uL, 4.957 mmol) were added under nitrogen, and the tube is capped. The reaction mixture is heated at 65° C. for 2.5 hours using the microwave (max power—100 W). The mixture is diluted with water (20 mL), extracted with ethylacetate (2×20 mL), and the combined organic phase is washed with water (3×15 mL), brine (15 mL), dried over anhydrous magnesium sulfate, and concentrated under reduced pressure. Purification by silica gel chromatography (40 g, 50-90% ethyl acetate/hexanes) gave the title compound (120 mg): $^1$H NMR (300 MHz, DMSO) δ 4.25 (m, 1.5H), 4.44 (m, 0.5H), 4.53 (m, 0.5H), 4.72 (m, 0.5H), 4.91 (m, 1H), 5.02 (s, 2H), 6.01 (d, 1H), 6.51 (s, 1H), 6.72 (dd, 1H), 6.77 (m, 1H), 7.47 (d, 2H), 7.70 (d, 2H), 7.83 (d, 1H), 8.60 (bd, 1H). MS (ESI+) m/z 412 [M+H].

Example 21

Preparation of 2,2-dichloro-N-[(1S,2R)-2-{4-[6-(2-cyanoethyl)pyridin-3-yl]phenyl}-1-(fluoromethyl)-2-hydroxyethyl]acetamide

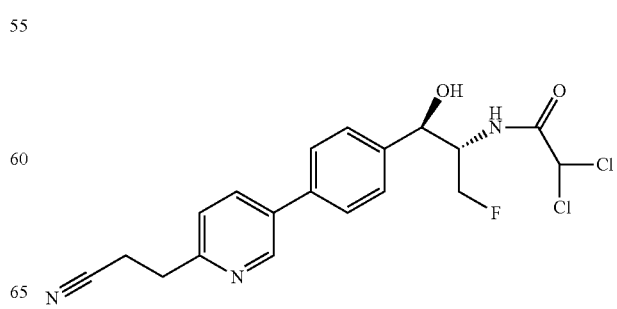

Step 1: Preparation of 3-[5-(4,4,5,5-tetramethyl-1,3,2-dioxaborolan-2-yl)pyridin-2-yl]propanenitrile

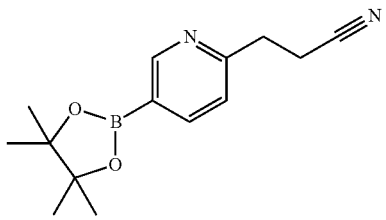 [SMILES: CC1(C)OB(c2ccc(CCC#N)nc2)OC1(C)C]

To a degassed solution of 3-(5-bromopyridin-2-yl)propanenitrile (579.0 mg, 2.74 mmol), bis(pinacolato)diboron (1.04 g, 4.11 mmol), and potassium acetate (979 mg, 9.97 mmol) in 1,4-dioxane (11.7 mL) is added commercially available [1,1'-Bis(diphenylphosphino)ferrocene]dichloropalladium(II) complex with dichloromethane (1:1) (204 mg, 0.249 mmol) and the reaction mixture heated at 80° C. for 4 hours. The reaction mixture is cooled to room temperature, diluted with ethyl acetate, and filtered through solka floc to remove the solids. The cake is washed with ethyl acetate and the combined filtrates were concentrated to yield the title compound that is used is the next step as is.

Step 2: Preparation of 2,2-dichloro-N-[(1S,2R)-2-{4-[6-(2-cyanoethyl)pyridin-3-yl]phenyl}-1-(fluoromethyl)-2-hydroxyethyl]acetamide

[1,1'-Bis(diphenylphosphino)ferrocene]dichloropalladium(II),complex with dichloromethane (1:1) (30.2 mg, 0.037 mmol) is added to a degassed mixture of the product of step 1, Example 21 along with 2,2-dichloro-N-[(1S,2R)-1-(fluoromethyl)-2-hydroxy-2-(4-iodophenyl)ethyl]acetamide (150 mg, 0.369 mmol), and cesium carbonate (482 mg, 1.48 mmol) in N,N-dimethylformamide (2.76 mL) at room temperature. The reaction mixture is heated at 60° C. for 4 hours. After cooling to room temperature the reaction mixture is concentrated under high vacuum, and the residue slurried in ethyl acetate. The slurry is filtered through solka floc washing the cake with ethyl acetate. The combined filtrates were concentrated and the brown residue purified by chromatography on silica gel eluting with a gradient of 50-80% ethyl acetate in hexanes to afford the title compound (72.5 mg): $^1$H NMR (300 MHz, DMSO-$d_6$) δ 2.92-2.97 (m, 2H), 3.08-3.13 (m, 2H), 4.23-4.28 (m, 1.5 H), 4.41-4.46 (m, 0.5H), 4.54-4.58 (m, 0.5H), 4.69-4.74 (m, 0.5H), 4.89-4.92 (m, 1H), 5.98 (d, 1H), 6.53 (s, 1H), 7.42-7.49 (m, 3H), 7.79 (d, 2H), 8.03-8.06 (dd, 1H), 8.62 (d, 1H), 8.83-8.84 (m, 1H). MS (ESI+) m/z of 410.0/412.0 [M+H].

Example 22

Preparation of 2,2-dichloro-N-[(1S,2R)-2-(4-{6-[cyano(fluoro)methyl]pyridin-3-yl}phenyl)-1-(fluoromethyl)-2-hydroxyethyl]acetamide

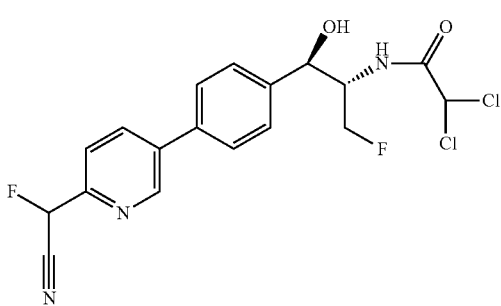 [SMILES: N#CC(F)c1ccc(-c2ccc([C@@H](O)[C@@H](CF)NC(=O)C(Cl)Cl)cc2)cn1]

Step 1: Preparation of 2-(5-bromopyridin-2-yl)-2-fluoroacetonitrile

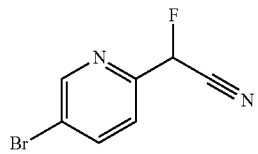 [SMILES: N#CC(F)c1ccc(Br)cn1]

Following the general procedure of step 2, Example 9 and making non-critical variations but using commercially available 2-(5-bromopyridin-2-yl)acetonitrile the title compound is obtained (253 mg): MS (ESI+) m/z 214.0 [M+H].

Step 2: Preparation of 2,2-dichloro-N-[(1S,2R)-2-(4-{6-[cyano(fluoro)methyl]pyridin-3-yl}phenyl)-1-(fluoromethyl)-2-hydroxyethyl]acetamide A stirred mixture of the product of step 1, Example 22 (127 mg, 0.591 mmol), bis(pinacolato)diboron (163 mg, 0.640 mmol), and potassium acetate (193 mg, 1.97 mmol) in dry dimethylformamide (4.9 mL) is sparged with nitrogen for 5 min before [1,1'-bis(diphenylphosphino)ferrocene]dichloropalladium(II), complex with dichloromethane (1:1) (40.2 mg, 0.0492 mmol) is added. The mixture is sparged with nitrogen for another 5 min, heated to 80° C. under nitrogen and maintained at this temperature. After 4.5 hours, the mixture is cooled to ambient temperature, solid 2,2-dichloro-N-[(1S,2R)-1-(fluoromethyl)-2-hydroxy-2-(4-iodophenyl)ethyl]acetamide (previously described in WO13057619 Preparation 1 page 16, 200 mg, 0.492 mmol) and cesium carbonate (0.562 g, 1.72 mmol) were added under a stream of nitrogen, and the mixture is sparged with nitrogen for 5 min and heated to 80° C. After 2 hours, the mixture is cooled to ambient temperature, diluted with water (25 mL), and extracted with ethylacetate (2×25 mL). The combined organic phase is washed with water (3×20 mL), brine (20 mL), dried over anhydrous magnesium sulfate, and concentrated under reduced pressure. Purification by silica gel chromatography (40 g, 25-45% ethyl acetate/hexanes) gave the title compound (77 mg): $^1$H NMR (300 MHz, DMSO-$d_6$) δ 4.28 (m, 1.5H), 4.45 (m, 0.5H), 4.58 (m, 0.5H), 4.72 (m, 0.5H), 4.93 (m, 1H), 6.02 (d, 1H), 6.53 (s, 1H), 6.93 (d, 1H), 7.51 (d, 2H), 7.77 (m, 3H), 8.28 (dd, 1H), 8.62 (bd, 1H), 9.04 (m, 1H). MS (ESI+) m/z 414 [M+H].

Example 23

Preparation of 2,2-dichloro-N-((1R,2S)-1-(4-(6-(1-cyanoethyl)pyridin-3-yl)phenyl)-3-fluoro-1-hydroxypropan-2-yl)acetamide

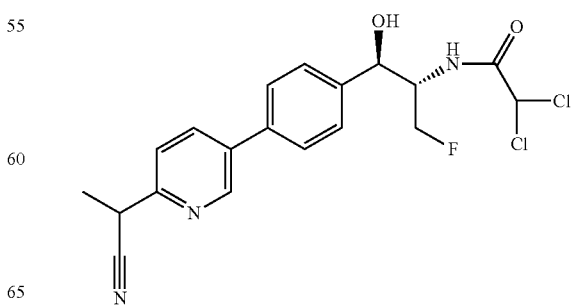

Step 1: Preparation of 2-(5-bromopyridin-2-yl)propanenitrile

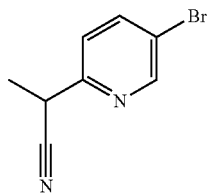

Sodium hydride (7 mg, 0.17 mmol) is added to 2-(5-bromopyridin-2-yl)acetonitrile (300 mg, 0.15 mmol) in THF at −5° C. After 30 minutes methyl iodide is added (56 μL, 1.5 mmol) and the mixture warmed to r.t. After stirring for 4 hours, the mixture is partitioned between brine and methylene chloride. The organics were separated, dried over magnesium sulfate and the solvent removed under reduced pressure. The crude material is purified by silica gel chromatography to give the title compound (128 mg): LCMS [M+H] 196.0.

Step 2: Preparation of 2,2-dichloro-N-[(1S,2R)-2-{4-[6-(1-cyanoethyl)pyridin-3-yl]phenyl}-1-(fluoromethyl)-2-hydroxyethyl]acetamide Following the general procedure of step 3, Example 4 and using the product of step 2, Example 4 and making non-critical variations but using the product of step 1, Example 23, the title compound is obtained (85 mg): $^1$H NMR (300 MHz, DMSO-$d_6$) δ 1.61 (d, 3H), 4.25 (m, 1.5H), 4.40-4.60 (m, 2H), 4.70 (m, 0.5H), 4.91 (m, 1H), 5.99 (d, 1H), 6.53 (s, 1H), 7.48 (d, 2H), 7.55 (d, 1H), 7.70 (d, 2H), 8.13 (dd, 1H), 8.62 (bd, 1H), 8.89 (m, 1H). MS (ESI+) m/z 410 [M+H].

Example 24

Preparation of 3-[5-(4-{(1R,2S)-2-[(difluoroacetyl)amino]-3-fluoro-1-hydroxypropyl}phenyl)pyridin-2-yl]oxetan-3-yl dihydrogen phosphate

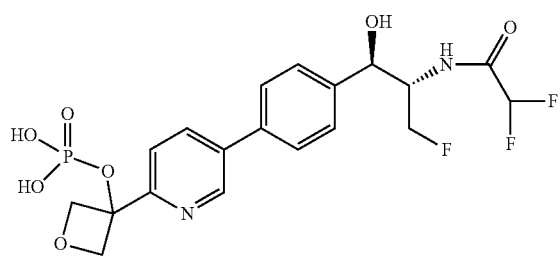 [SMILES: O=C(N[C@H](CF)[C@H](O)c1ccc(-c2ccc(C3(OP(=O)(O)O)COC3)nc2)cc1)C(F)F]

Step 1: Preparation of dibenzyl 3-(5-{4-[(4S,5R)-3-(difluoroacetyl)-4-(fluoromethyl)-2,2-dimethyl-1,3-oxazolidin-5-yl]phenyl}pyridin-2-yl)oxetan-3-yl phosphate

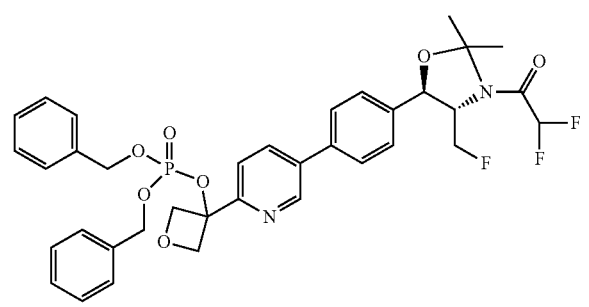 [SMILES: CC1(C)O[C@H](c2ccc(-c3ccc(C4(OP(=O)(OCc5ccccc5)OCc5ccccc5)COC4)nc3)cc2)[C@@H](CF)N1C(=O)C(F)F]

Sodium Hydride, 60% in mineral oil(156.4 mg, 3.91 mmol) is added to a stirred solution of the product of step 5, Example 8 (910.0 mg, 2.08 mmol) in tetrahydrofuran (23.3 mL) at 0° C. The yellow reaction mixture is stirred at this temperature for 1 h prior to the addition of solid tetrabenzyl pyrophosphate (1.23 g, 2.29 mmol) and stirring is continued for 1 hour. The mixture is quenched with saturate ammonium chloride solution and extracted with ethyl acetate. The combined organic layers were washed with brine, dried, and concentrated to a white slurry. The solid is slurried in ethylacetate and filtered to remove phosphate by-products. The filtrate is concentrated and purified by CombiFlash (12 g column) eluting with 0-100% ethyl acetate in hexanes to afford the title compound (120 mg): MS (ESI+) m/z 697.0 [M+H].

Step 2: Preparation of 3-[5-(4-{(1R,2S)-2-[(difluoroacetyl)amino]-3-fluoro-1-hydroxypropyl}phenyl)pyridin-2-yl]oxetan-3-yl dihydrogen phosphate 10% Palladium on carbon (45.1 mg, 0.042 mmol) is added to a degassed solution of the product of step 1, Example 24 (451.0 mg, 0.687 mmol) in ethanol (17.1 mL) and water (3.42 mL). After purging with nitrogen, 1 atm of hydrogen is bubbled through the reaction mixture for 5 min before being left under 1 atm of hydrogen. After 1 hour the reaction mixture is filtered through solka floc, and the cake washed with ethanol. The filtrate is concentrated and azeotroped with ethanol to afford a white foam. The crude intermediate is taken up in methylene chloride (4.51 mL) and cooled at 0° C. before trifluoroacetic acid (1.06 mL, 13.7 mmol) is added and the mixture warmed to room temperature. After 4 hours the mixture is concentrated and azeotroped with methylene chloride then purified by reverse phase CombiFlash (30 g column) eluting with 0-25% acetonitrile in water (with 0.1% trifluoroacetic acid) to afford the title compound (120 mg): $^1$H NMR (300 MHz, DMSO-$_6$) δ 4.27-4.52 (m, 2.5H), 4.66-4.69 (m, 0.5H), 4.87-4.90 (m, 1H), 4.97 (d, 2H), 5.08 (d, 2H), 6.20 (t, 1H), 7.48 (d, 2H), 7.69 (d, 1H), 7.75 (d, 2H), 8.14-8.17 (dd, 1H), 8.83 (d, 1H), 8.96-8.97 (m, 1H). MS (ESI+) m/z 477.1 [M+H].

Example 25

Preparation of (1R,2S)-2-[(difluoroacetyl)amino]-3-fluoro-1-{4-[6-(3-hydroxyoxetan-3-yl)pyridin-3-yl]phenyl}propyl dihydrogen phosphate

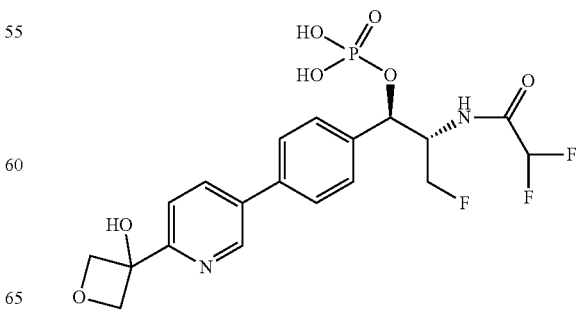

Step 1: Preparation of dibenzyl (1R,2S)-2-[(difluoroacetyl)amino]-3-fluoro-1-{4-[6-(3-hydroxyoxetan-3-yl)pyridin-3-yl]phenyl}propyl phosphate

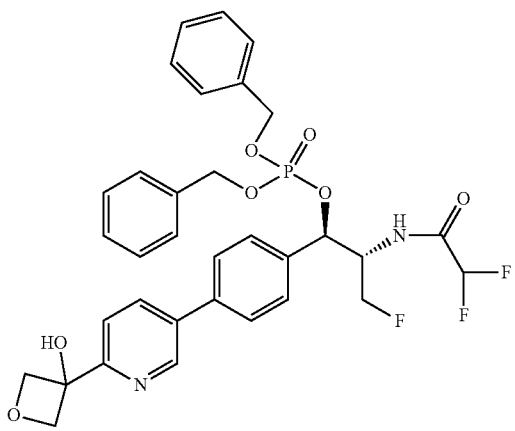 [SMILES: O=C(N[C@H](CF)[C@H](OP(=O)(OCc1ccccc1)OCc1ccccc1)c1ccc(-c2ccc(C3(O)COC3)nc2)cc1)C(F)F]

Trifluoroacetic acid (118 μL, 1.53 mmol) is added to a stirred solution of the product of step 6, Example 8 (303 mg, 0.764 mmol) and pyridine (124 μL, 1.53 mmol) in tetrahydrofuran (4.78 mL) at 0° C. and after 5 min of stirring bis(benzyloxy)(diisopropylamino)phosphine (0.499 mL, 1.34 mmol) is added dropwise before the reaction mixture is warmed to room temperature. After 7 hours the reaction mixture is cooled at 0° C. and 30% Hydrogen peroxide in water (137 μL, 1.34 mmol) is added dropwise. The mixture is warmed to rt and stirred for 30 min before being diluted with ethyl acetate and quenched with sat. sodium bisulfite solution. The layers were separated and the organic phase washed with brine, dried, and concentrated. The residue is purified by CombiFlash (2×, 12 g column) eluting with 0-100% ethyl acetate in hexanes to arrive at the title compound (310 mg): MS (ESI+) m/z 657.4 [M+H].

Step 2: Preparation of (1R,2S)-2-[(difluoroacetyl)amino]-3-fluoro-1-{4-[6-(3-hydroxyoxetan-3-yl)pyridin-3-yl]phenyl}propyl dihydrogen phosphate 5% Palladium on carbon (31.0 mg, 0.015 mmol) is added to a degassed solution of the product of step 1, Example 25 (310.0 mg, 0.472 mmol) in ethanol (11.7 mL) and water (2.35 mL) at room temperature. A balloon of hydrogen is bubbled through the reaction mixture for 5 min before the reaction mixture is set under 1 atm of hydrogen. After 1 h the reaction mixture is filtered through solka floc and washed with ethanol. The filtrate is concentrated and azeotroped with ethanol to afford a white solid. This is slurried in MTBE, heated, and filtered to give the title compound (185 mg): $^1$H NMR (300 MHz, DMSO-$d_6$) δ 4.31-4.37 (m, 0.5H), 4.47-4.61 (m, 2H), 4.64 (d, 2H), 4.67-4.75 (m, 0.5H), 4.96 (d, 2H), 5.44-5.48 (dd, 1H), 6.19 (t, 1H), 6.60 (br, s, 1H), 7.49 (d, 2H), 7.67 (d, 1H), 7.74 (d, 2H), 8.10-8.13 (dd, 1H), 8.95-8.96 (dd, 1H), 9.01 (d, 1H). MS (ESI+) m/z 477.0 [M+H].

Example 26

Preparation of 2,2-difluoro-N-{(1S,2R)-1-(fluoromethyl)-2-hydroxy-2-[4-(1-oxetan-3-yl-2-oxo-1,2-dihydropyridin-4-yl)phenyl]ethyl}acetamide

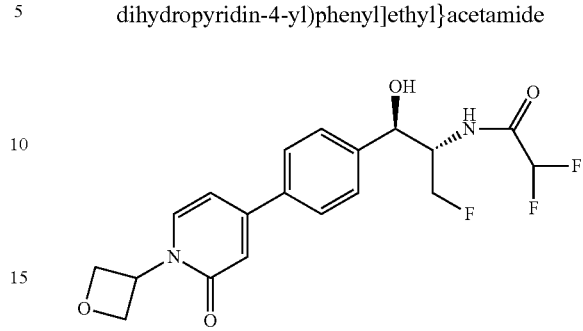

Following the general procedure of Step 2, Example 17 and making non-critical variations but using 4-bromo-1-oxetan-3-ylpyridin-2(1H)-one (0.150 g, 0.652 mmol, previously described in US2011/040443, Intermediate 22, p. 69) and the product of step 2, Example 13 (203 mg, 0.543 mmol) the title compound is obtained (66.0 mg): $^1$H NMR (300 MHz, DMSO-$d_6$) δ 4.28-4.45 (m, 1.5H), 4.42-4.54 (m, 1H), 4.66-4.69 (m, 0.5H), 4.76 (t, 2H), 4.86-4.91 (m, 1H), 4.90 (t, 2H), 5.47-5.54 (m, 1H), 5.94 (d, 1H), 6.19 (t, 1H), 6.66-6.73 (m, 2H), 7.46 (d, 2H), 7.72 (d, 2H), 7.85-7.85 (dd, 1H), 8.84 (d, 1H). MS (ESI+) m/z 397.0 [M+H].

Example 27

Preparation of N-[(1S,2R)-2-[4-(1-azetidin-3-yl-2-oxo-1,2-dihydropyridin-4-yl)phenyl]-1-(fluoromethyl)-2-hydroxyethyl]-2,2-difluoroacetamide

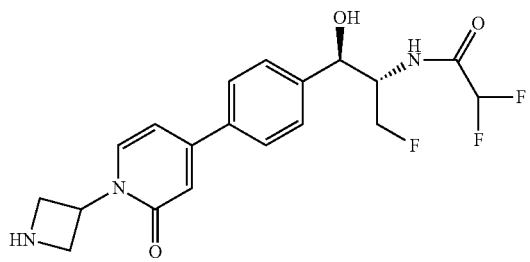 [SMILES: O=C(N[C@H](CF)[C@H](O)c1ccc(-c2ccn(C3CNC3)c(=O)c2)cc1)C(F)F]

Step 1: Preparation of tert-butyl 3-[4-{4-[(4S,5R)-3-(difluoroacetyl)-4-(fluoromethyl)-2,2-dimethyl-1,3-oxazolidin-5-yl]phenyl}-2-oxopyridin-1(2H)-yl]azetidine-1-carboxylate

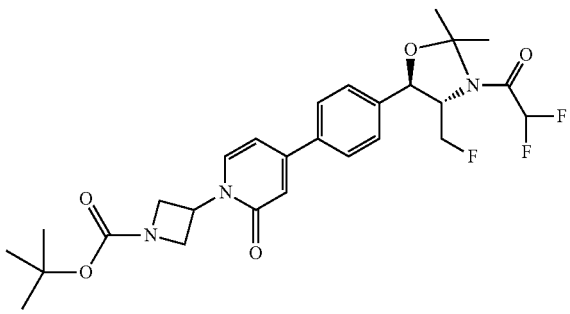 [SMILES: CC(C)(C)OC(=O)N1CC(n2ccc(-c3ccc([C@H]4OC(C)(C)N(C(=O)C(F)F)[C@@H]4CF)cc3)cc2=O)C1]

Following the general procedure of Step 2, Example 17 and making non-critical variations but using tert-butyl 3-(4-bromo-2-oxopyridin-1(2H)-yl)azetidine-1-carboxylate (333 mg, 1.01 mmol, previously described in US2011/040443, Intermediate 23, p. 70) and the product of step 4, Example 8 (380 mg, 0.920 mmol) the title compound is obtained (425 mg): MS (ESI+) m/z 535.7 [M+H].

Step 2: Preparation of N-[(1S,2R)-2-[4-(1-azetidin-3-yl-2-oxo-1,2-dihydropyridin-4-yl)phenyl]-1-(fluoromethyl)-2-hydroxyethyl]-2,2-difluoroacetamide Following the general procedure of Step 2, Example 17 and making non-critical variations but using the product of step 1, Example 27 (425 mg, 0.793 mmol) and lyophilizing the final compound from water the title compound is obtained (129 mg): $^1$H NMR (300 MHz, DMSO-d$_6$) δ 3.60 (t, 2H), 3.80 (t, 2H), 4.27-4.33 (m, 1.5H), 4.42-4.54 (m, 1H), 4.66-4.71 (m, 0.5H), 4.87 (d, 1H), 5.25-5.29 (m, 1H), 6.20 (t, 1H), 6.62-6.72 (m, 2H), 7.44 (d, 2H), 7.69 (d, 2H), 7.94 (d, 1H). MS (ESI+) m/z 396.1, 394.1 [M+H].

Example 28

Preparation of N-((1R,2S)-1-(4-(6-(3-Aminopropanoyl)pyridin-3-yl)phenyl)-3-fluoro-1-hydroxypropan-2-yl)-2,2-difluoroacetamide

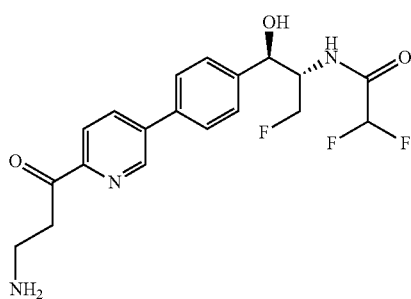 [SMILES: NCCC(=O)c1ccc(-c2ccc([C@@H](O)[C@@H](CF)NC(=O)C(F)F)cc2)cn1]

Step 1: Preparation of tert-butyl (3-(5-bromopyridin-2-yl)-3-hydroxypropyl)carbamate

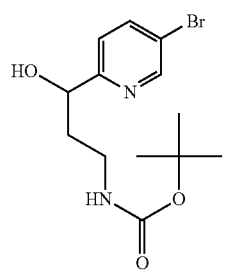 [SMILES: CC(C)(C)OC(=O)NCCC(O)c1ccc(Br)cn1]

A solution of 2,5-dibromopyridine (5 g, 21 mmol), in dry toluene (200 mL, 0.1 M) is cooled to −75° C. under a blanket of nitrogen. 2.5 M n-BuLi in hexanes (16 mL, 25 mmol, 1.2 eq) is added drop-wise maintaining a temp less than −73° C. and the reaction mixture is stirred at −73° C. to −78° C. for 2 hours. The mixture is then added to a solution of tert-butyl (3-oxopropyl)carbamate (3.66 g, 21 mmol) in toluene (50 mL) at −78° C. The reaction mixture is stirred at −78° C. for 1 hour, before being allowed to warm slowly to room temperature and stirred overnight. The reaction mixture is quenched with saturated ammonium chloride solution (100 ml) and the toluene phase is separated and concentrated. The crude material is purified by chromatography (0-45% ethyl acetate in heptane) to give the title compound (3.1 g). MS (ESI+) m/z 331.0 [M+H].

Step 2: Preparation of tert-butyl (3-(5-bromopyridin-2-yl)-3-oxopropyl)carbamate

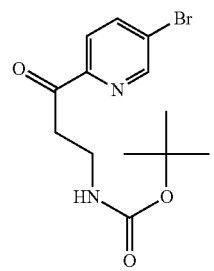 [SMILES: CC(C)(C)OC(=O)NCCC(=O)c1ccc(Br)cn1]

tert-Butyl (3-(5-bromopyridin-2-yl)-3-hydroxypropyl)carbamate(224 mg, 0.68 mmol) in ethylacetate (4.5 mL, 0.15 M) had 1.2 equivalents of Dess-Martin periodinane (344 mg, 0.81 mmol) added to it and stirred for 1 hour. The reaction mixture is then filtered and washed with sodium hydrogen carbonate and evaporated to give the title compound (220 mg): MS (ESI+) m/z 273.0 [M−Bu$^t$+H].

Step 3: Preparation of tert-butyl (3-(5-(4-((4S,5R)-3-(2,2-difluoroacetyl)-4-(fluoromethyl)-2,2-dimethyloxazolidin-5-yl)phenyl)pyridin-2-yl)-3-oxopropyl)carbamate

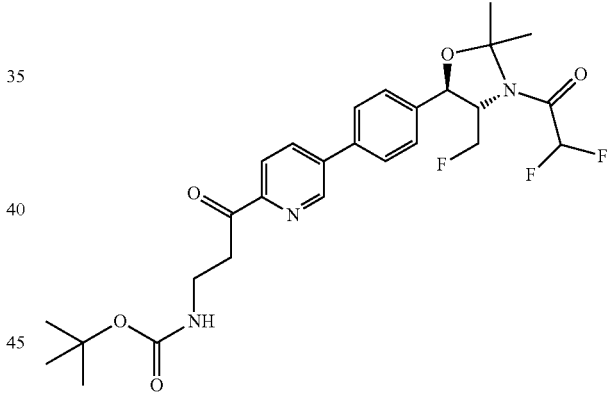

A solution of the product of step 2, Example 28 (1 g, 3 mmol) and the product of step 4, Example 8 (1.26 g, 3 mmol) in toluene 20 ml and isopropyl alcohol (20 mL) is treated with sodium hydrogen carbonate saturate solution (10 ml). The mixture is deoxygenated and PdCl$_2$(dppf) (111 mg, 0.15 mmol) is added and the reaction mixture deoxygenated again. The mixture is heated at 75° C. overnight. The reaction mixture is partitioned between ethyl acetate (100 ml) and water (50 ml). The phases were separated, the aqueous extracted with ethylacetate and the combined organic layers evaporated. Column chromatography (0-50% ethyl acetate in heptane) gave the title compound (554 mg). MS (ESI+) m/z 536.0 [M+H].

Step 4: Preparation of N-((1R,2S)-1-(4-(6-(3-Aminopropanoyl)pyridin-3-yl)phenyl)-3-fluoro-1-hydroxypropan-2-yl)-2,2-difluoroacetamide A solution of the product of step 3, Example 28 (554 mg, 1 mmol) in methylene chloride (20 ml) at 0° C. is treated with trifluoroacetic acid (10 ml) and allowed to warm to room temperature. After 30 minutes, water (3 drops) is added. The reaction mixture is stirred at room temperature for 3 hours. The reaction mixture is then diluted with toluene and evaporated. The material is purified by HPLC (Gemini NX C18 MP A=0.1% trifluoroacetic acid in water MP B=0.1% trifluoroacetic acod in acetonitrile, Gradient 10% B to 50% in 10 min) to give title compound (248 mg): MS (ESI+) m/z 396.0 [M+H].

$^1$H NMR (400 MHz, d6-DMSO) δ 3.1-3.3 (m, 2H), 3.6 (t, 2H), 4.25-4.4 (m, 1.5H), 4.45 (t, 0.5H), 4.55-4.6 (m, 0.5H), 4.65-4.75 (m, 0.5H), 4.9 (d, 1H), 6.2 (t, 1H), 7.5 (d, 2H), 7.8 (bs, 3H), 7.85 (d, 2H), 8.1 (d, 1H), 8.3 (dd, 1H), 8.85 (d, 1H), 9.15 (d, 1H).

Examples 29-103

These additional compounds of the present invention are prepared by procedures known in the art:

| Example | Structure | Name | LCMS |
| --- | --- | --- | --- |
| 29 | 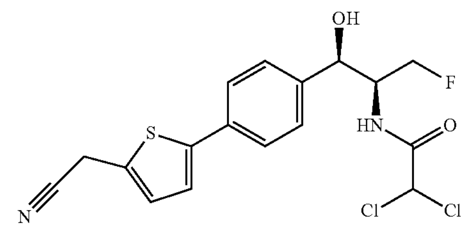 [SMILES: N#CCc1ccc(-c2ccc([C@@H](O)[C@@H](CF)NC(=O)C(Cl)Cl)cc2)s1] | 2,2-dichloro-N-((1R,2S)-1-(4-(5-(cyanomethyl)thiophen-2-yl)phenyl)-3-fluoro-1-hydroxypropan-2-yl)acetamide | 401.1 |
| 30 | 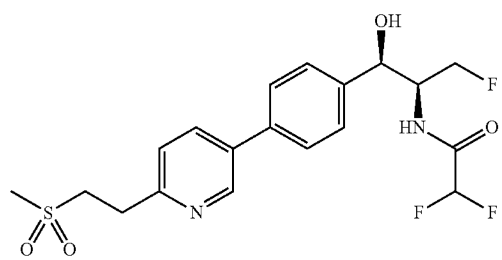 [SMILES: CS(=O)(=O)CCc1ccc(-c2ccc([C@@H](O)[C@@H](CF)NC(=O)C(F)F)cc2)cn1] | 2,2-difluoro-N-((1R,2S)-3-fluoro-1-hydroxy-1-(4-(6-(2-(methylsulfonyl)ethyl)pyridin-3-yl)phenyl)propan-2-yl)acetamide | 431.1 |
| 31 | 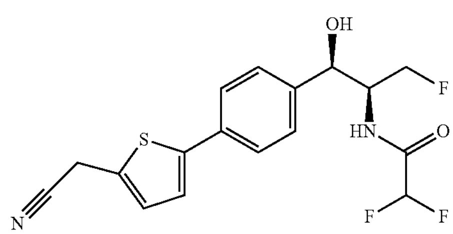 [SMILES: N#CCc1ccc(-c2ccc([C@@H](O)[C@@H](CF)NC(=O)C(F)F)cc2)s1] | N-((1R,2S)-1-(4-(5-(cyanomethyl)thiophen-2-yl)phenyl)-3-fluoro-1-hydroxypropan-2-yl)-2,2-difluoroacetamide | 369.1 |
| 32 | 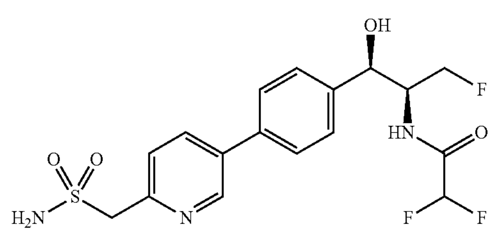 [SMILES: NS(=O)(=O)Cc1ccc(-c2ccc([C@@H](O)[C@@H](CF)NC(=O)C(F)F)cc2)cn1] | 2,2-difluoro-N-((1R,2S)-3-fluoro-1-hydroxy-1-(4-(6-(sulfamoylmethyl)pyridin-3-yl)phenyl)propan-2-yl)acetamide | 418.1 |
| 33 | 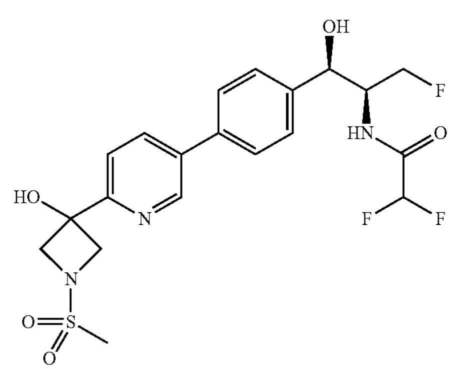 [SMILES: CS(=O)(=O)N1CC(O)(c2ccc(-c3ccc([C@@H](O)[C@@H](CF)NC(=O)C(F)F)cc3)cn2)C1] | 2,2-difluoro-N-((1R,2S)-3-fluoro-1-hydroxy-1-(4-(6-(3-hydroxy-1-(methylsulfonyl)azetidin-3-yl)pyridin-3-yl)phenyl)propan-2-yl)acetamide | 474.1 |

-continued

| Example | Structure | Name | LCMS |
|---|---|---|---|
| 34 | 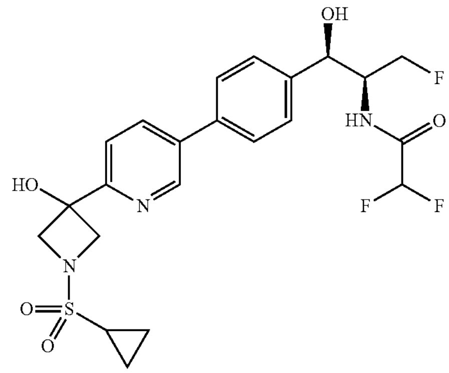 [SMILES: O=C(N[C@H](CF)[C@H](O)c1ccc(-c2ccc(C3(O)CN(S(=O)(=O)C4CC4)C3)nc2)cc1)C(F)F] | N-((1R,2S)-1-(4-(6-(1-(cyclopropylsulfonyl)-3-hydroxyazetidin-3-yl)pyridin-3-yl)phenyl)-3-fluoro-1-hydroxypropan-2-yl)-2,2-difluoroacetamide | 500.1 |
| 35 | 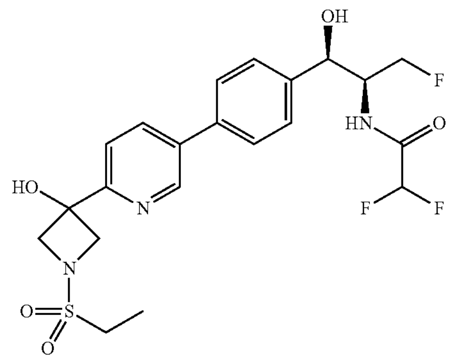 [SMILES: CCS(=O)(=O)N1CC(O)(c2ccc(-c3ccc([C@@H](O)[C@@H](CF)NC(=O)C(F)F)cc3)cn2)C1] | N-((1R,2S)-1-(4-(6-(1-(ethylsulfonyl)-3-hydroxyazetidin-3-yl)pyridin-3-yl)phenyl)-3-fluoro-1-hydroxypropan-2-yl)-2,2-difluoroacetamide | 488.1 |
| 36 | 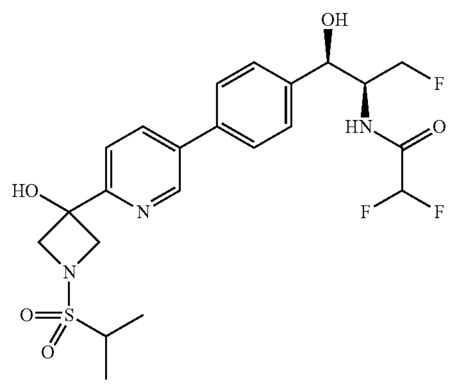 [SMILES: CC(C)S(=O)(=O)N1CC(O)(c2ccc(-c3ccc([C@@H](O)[C@@H](CF)NC(=O)C(F)F)cc3)cn2)C1] | 2,2-difluoro-N-((1R,2S)-3-fluoro-1-hydroxy-1-(4-(6-(3-hydroxy-1-(isopropylsulfonyl)azetidin-3-yl)pyridin-3-yl)phenyl)propan-2-yl)acetamide | 502.2 |
| 37 | 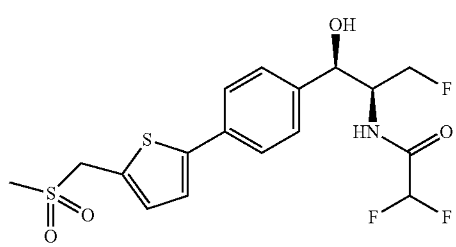 [SMILES: CS(=O)(=O)Cc1ccc(-c2ccc([C@@H](O)[C@@H](CF)NC(=O)C(F)F)cc2)s1] | 2,2-difluoro-N-((1R,2S)-3-fluoro-1-hydroxy-1-(4-(5-((methylsulfonyl)methyl)thiophen-2-yl)phenyl)propan-2-yl)acetamide | 422.1 |
| 38 | 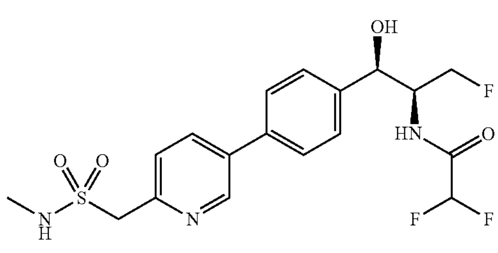 [SMILES: CNS(=O)(=O)Cc1ccc(-c2ccc([C@@H](O)[C@@H](CF)NC(=O)C(F)F)cc2)cn1] | 2,2-difluoro-N-((1R,2S)-3-fluoro-1-hydroxy-1-(4-(6-((N-methylsulfamoyl)methyl)pyridin-3-yl)phenyl)propan-2-yl)acetamide | 432.1 |

-continued

| Example | Structure | Name | LCMS |
|---|---|---|---|
| 39 | 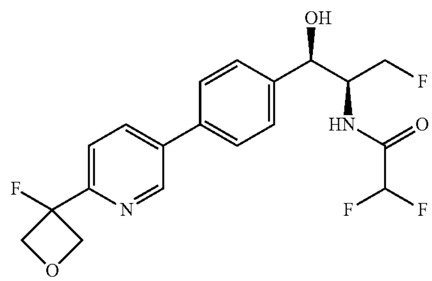 [SMILES: O=C(N[C@H](CF)[C@H](O)c1ccc(-c2ccc(C3(F)COC3)nc2)cc1)C(F)F] | 2,2-difluoro-N-((1R,2S)-3-fluoro-1-(4-(6-(3-fluorooxetan-3-yl)pyridin-3-yl)phenyl)-1-hydroxypropan-2-yl)acetamide | 399.1 |
| 40 | 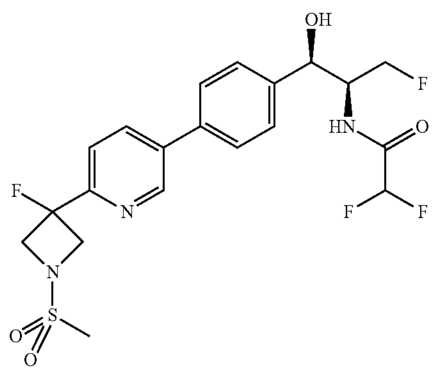 [SMILES: CS(=O)(=O)N1CC(F)(c2ccc(-c3ccc([C@@H](O)[C@@H](CF)NC(=O)C(F)F)cc3)cn2)C1] | 2,2-difluoro-N-((1R,2S)-3-fluoro-1-(4-(6-(3-fluoro-1-(methylsulfonyl)azetidin-3-yl)pyridin-3-yl)phenyl)-1-hydroxypropan-2-yl)acetamide | 476.1 |
| 41 | 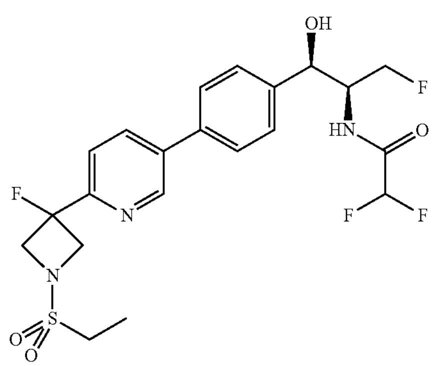 [SMILES: CCS(=O)(=O)N1CC(F)(c2ccc(-c3ccc([C@@H](O)[C@@H](CF)NC(=O)C(F)F)cc3)cn2)C1] | N-((1R,2S)-1-(4-(6-(1-(ethylsulfonyl)-3-fluoroazetidin-3-yl)pyridin-3-yl)phenyl)-3-fluoro-1-hydroxypropan-2-yl)-2,2-difluoroacetamide | 490.1 |
| 42 | 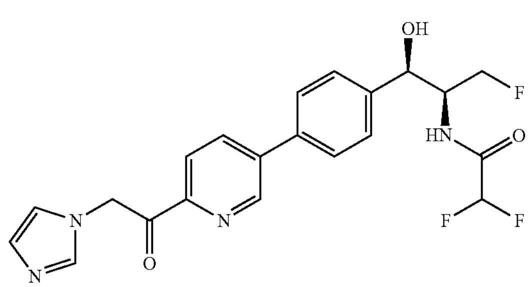 [SMILES: O=C(Cn1ccnc1)c1ccc(-c2ccc([C@@H](O)[C@@H](CF)NC(=O)C(F)F)cc2)cn1] | N-((1R,2S)-1-(4-(6-(2-(1H-imidazol-1-yl)acetyl)pyridin-3-yl)phenyl)-3-fluoro-1-hydroxypropan-2-yl)-2,2-difluoroacetamide | 433.4 |

-continued

| Example | Structure | Name | LCMS |
|---|---|---|---|
| 43 | 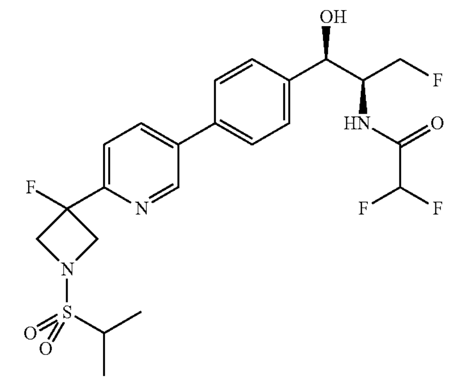 [SMILES: CC(C)S(=O)(=O)N1CC(F)(c2ccc(-c3ccc([C@@H](O)[C@@H](CF)NC(=O)C(F)F)cc3)cn2)C1] | 2,2-difluoro-N-((1R,2S)-3-fluoro-1-(4-(6-(3-fluoro-1-(isopropylsulfonyl)azetidin-3-yl)pyridin-3-yl)phenyl)-1-hydroxypropan-2-yl)acetamide | 504.2 |
| 44 | 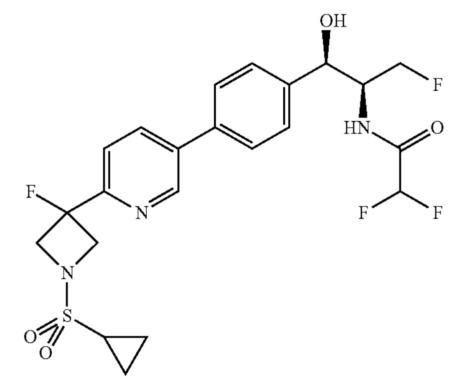 [SMILES: O=C(N[C@H](CF)[C@H](O)c1ccc(-c2ccc(C3(F)CN(S(=O)(=O)C4CC4)C3)nc2)cc1)C(F)F] | N-((1R,2S)-1-(4-(6-(1-(cyclopropylsulfonyl)-3-fluoroazetidin-3-yl)pyridin-3-yl)phenyl)-3-fluoro-1-hydroxypropan-2-yl)-2,2-difluoroacetamide | 502.2 |
| 45 | 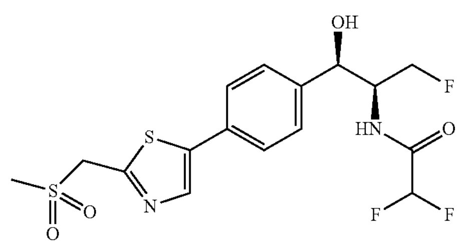 | 2,2-difluoro-N-((1R,2S)-3-fluoro-1-hydroxy-1-(4-(2-((methylsulfonyl)methyl)thiazol-5-yl)phenyl)propan-2-yl)acetamide | 423.1 |
| 46 | 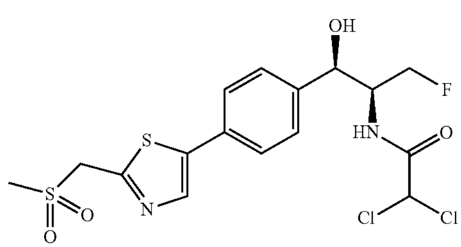 [SMILES: CS(=O)(=O)Cc1ncc(-c2ccc([C@@H](O)[C@@H](CF)NC(=O)C(Cl)Cl)cc2)s1] | 2,2-dichloro-N-((1R,2S)-3-fluoro-1-hydroxy-1-(4-(2-((methylsulfonyl)methyl)thiazol-5-yl)phenyl)propan-2-yl)acetamide | 455.0 |
| 47 | 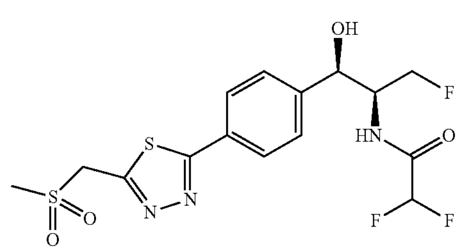 [SMILES: CS(=O)(=O)Cc1nnc(-c2ccc([C@@H](O)[C@@H](CF)NC(=O)C(F)F)cc2)s1] | 2,2-difluoro-N-((1R,2S)-3-fluoro-1-hydroxy-1-(4-(5-((methylsulfonyl)methyl)-1,3,4-thiadiazol-2-yl)phenyl)propan-2-yl)acetamide | 424.1 |

| Example | Structure | Name | LCMS |
|---|---|---|---|
| 48 | 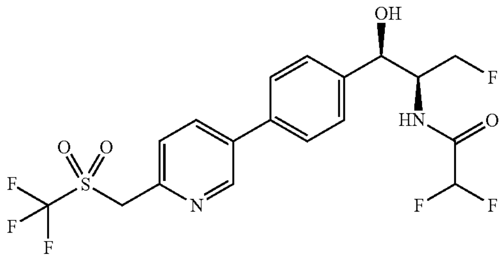 [SMILES: O=C(N[C@H](CF)[C@H](O)c1ccc(-c2ccc(CS(=O)(=O)C(F)(F)F)nc2)cc1)C(F)F] | 2,2-difluoro-N-((1R,2S)-3-fluoro-1-hydroxy-1-(4-(6-(((trifluoromethyl)sulfonyl)methyl)pyridin-3-yl)phenyl)propan-2-yl)acetamide | 471.1 |
| 49 | 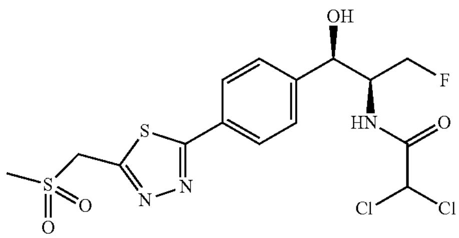 [SMILES: CS(=O)(=O)Cc1nnc(-c2ccc([C@@H](O)[C@@H](CF)NC(=O)C(Cl)Cl)cc2)s1] | 2,2-dichloro-N-((1R,2S)-3-fluoro-1-hydroxy-1-(4-(5-((methylsulfonyl)methyl)-1,3,4-thiadiazol-2-yl)phenyl)propan-2-yl)acetamide | 456.0 |
| 50 | 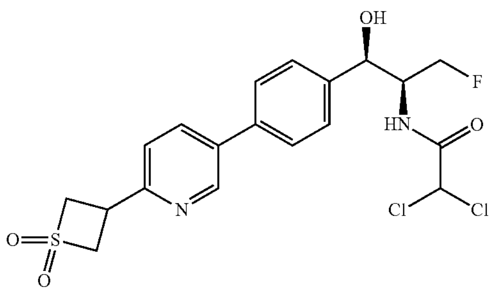 [SMILES: O=C(N[C@H](CF)[C@H](O)c1ccc(-c2ccc(C3CS(=O)(=O)C3)nc2)cc1)C(Cl)Cl] | 2,2-dichloro-N-((1R,2S)-1-(4-(6-(1,1-dioxidothietan-3-yl)pyridin-3-yl)phenyl)-3-fluoro-1-hydroxypropan-2-yl)acetamide | 429.1 |
| 51 | 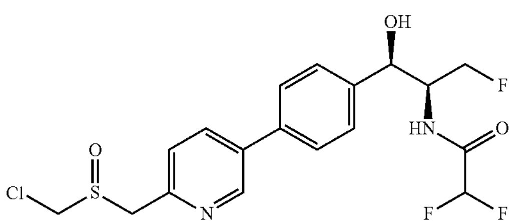 [SMILES: O=C(N[C@H](CF)[C@H](O)c1ccc(-c2ccc(CS(=O)CCl)nc2)cc1)C(F)F] | N-((1R,2S)-1-(4-(6-(((chloromethyl)sulfinyl)methyl)pyridin-3-yl)phenyl)-3-fluoro-1-hydroxypropan-2-yl)-2,2-difluoroacetamide | 435.1 |
| 52 | 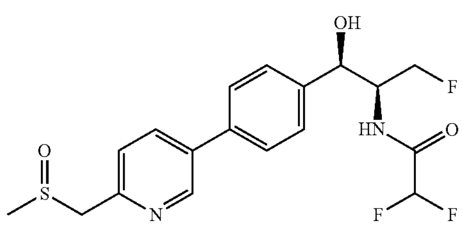 [SMILES: CS(=O)Cc1ccc(-c2ccc([C@@H](O)[C@@H](CF)NC(=O)C(F)F)cc2)cn1] | 2,2-difluoro-N-((1R,2S)-3-fluoro-1-hydroxy-1-(4-(6-((methylsulfinyl)methyl)pyridin-3-yl)phenyl)propan-2-yl)acetamide | 401.1 |
| 53 | 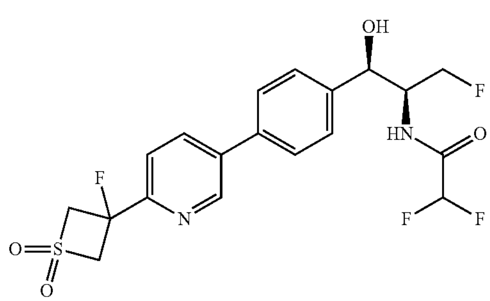 [SMILES: O=C(N[C@H](CF)[C@H](O)c1ccc(-c2ccc(C3(F)CS(=O)(=O)C3)nc2)cc1)C(F)F] | 2,2-difluoro-N-((1R,2S)-3-fluoro-1-(4-(6-(3-fluoro-1,1-dioxidothietan-3-yl)pyridin-3-yl)phenyl)-1-hydroxypropan-2-yl)acetamide | 447.1 |

-continued

| Example | Structure | Name | LCMS |
|---|---|---|---|
| 54 | 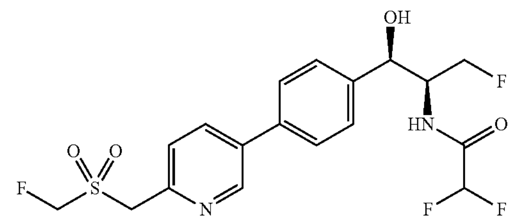 [SMILES: O=C(N[C@H](CF)[C@H](O)c1ccc(-c2ccc(CS(=O)(=O)CF)nc2)cc1)C(F)F] | 2,2-difluoro-N-((1R,2S)-3-fluoro-1-(4-(6-(((fluoromethyl)sulfonyl)methyl)pyridin-3-yl)phenyl)-1-hydroxypropan-2-yl)acetamide | 435.1 |
| 55 | 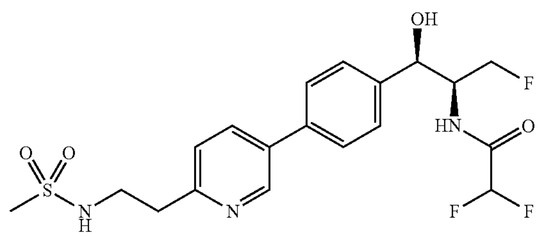 [SMILES: CS(=O)(=O)NCCc1ccc(-c2ccc([C@@H](O)[C@@H](CF)NC(=O)C(F)F)cc2)cn1] | 2,2-difluoro-N-((1R,2S)-3-fluoro-1-hydroxy-1-(4-(6-(2-(methylsulfonamido)ethyl)pyridin-3-yl)phenyl)propan-2-yl)acetamide | 446.1 |
| 56 | 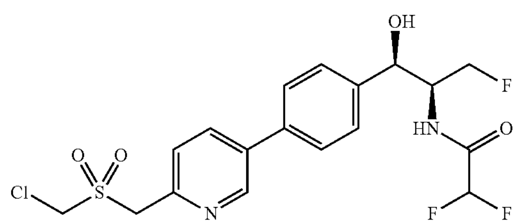 [SMILES: O=C(N[C@H](CF)[C@H](O)c1ccc(-c2ccc(CS(=O)(=O)CCl)nc2)cc1)C(F)F] | N-((1R,2S)-1-(4-(6-(((chloromethyl)sulfonyl)methyl)pyridin-3-yl)phenyl)-3-fluoro-1-hydroxypropan-2-yl)-2,2-difluoroacetamide | 451.1 |
| 57 | 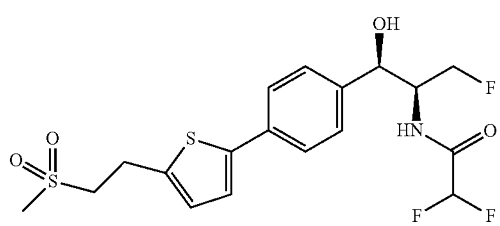 [SMILES: CS(=O)(=O)CCc1ccc(-c2ccc([C@@H](O)[C@@H](CF)NC(=O)C(F)F)cc2)s1] | 2,2-difluoro-N-((1R,2S)-3-fluoro-1-hydroxy-1-(4-(5-(2-(methylsulfonyl)ethyl)thiophen-2-yl)phenyl)propan-2-yl)acetamide | 436.1 |
| 58 | 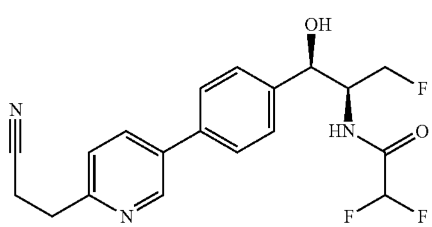 [SMILES: N#CCCc1ccc(-c2ccc([C@@H](O)[C@@H](CF)NC(=O)C(F)F)cc2)cn1] | N-((1R,2S)-1-(4-(6-(2-cyanoethyl)pyridin-3-yl)phenyl)-3-fluoro-1-hydroxypropan-2-yl)-2,2-difluoroacetamide | 378.1 |
| 59 | 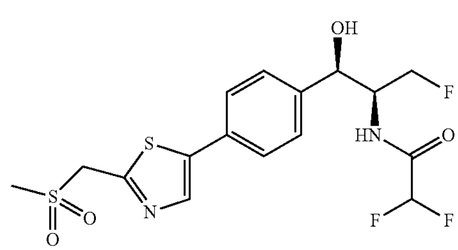 | 2,2-difluoro-N-((1R,2S)-3-fluoro-1-hydroxy-1-(4-(2-((methylsulfonyl)methyl)thiazol-5-yl)phenyl)propan-2-yl)acetamide | 423.1 |

-continued

| Example | Structure | Name | LCMS |
|---|---|---|---|
| 60 | 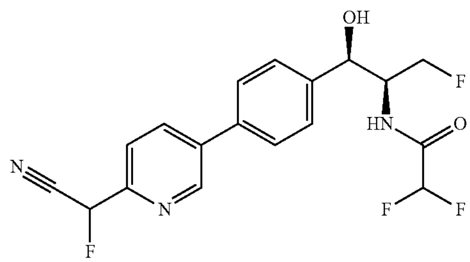 [SMILES: N#CC(F)c1ccc(-c2ccc([C@@H](O)[C@@H](CF)NC(=O)C(F)F)cc2)cn1] | N-((1R,2S)-1-(4-(6-(cyanofluoromethyl)pyridin-3-yl)phenyl)-3-fluoro-1-hydroxypropan-2-yl)-2,2-difluoroacetamide | 382.1 |
| 61 | 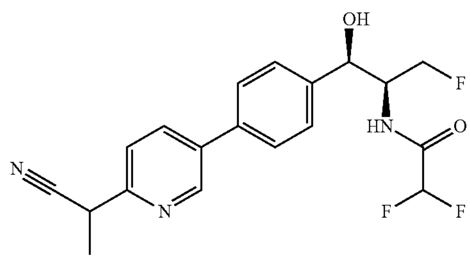 [SMILES: CC(C#N)c1ccc(-c2ccc([C@@H](O)[C@@H](CF)NC(=O)C(F)F)cc2)cn1] | N-((1R,2S)-1-(4-(6-(1-cyanoethyl)pyridin-3-yl)phenyl)-3-fluoro-1-hydroxypropan-2-yl)-2,2-difluoroacetamide | 378.1 |
| 62 | 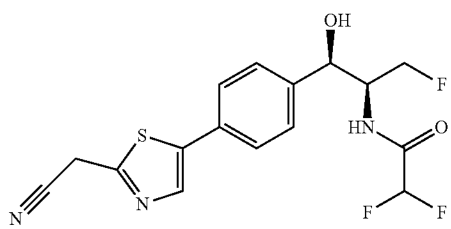 | N-((1R,2S)-1-(4-(2-(cyanomethyl)thiazol-5-yl)phenyl)-3-fluoro-1-hydroxypropan-2-yl)-2,2-difluoroacetamide | 370.1 |
| 63 | 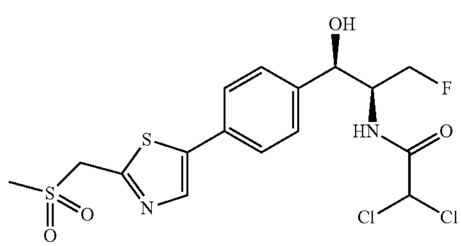 [SMILES: CS(=O)(=O)Cc1ncc(-c2ccc([C@@H](O)[C@@H](CF)NC(=O)C(Cl)Cl)cc2)s1] | 2,2-dichloro-N-((1R,2S)-3-fluoro-1-hydroxy-1-(4-(2-((methylsulfonyl)methyl)thiazol-5-yl)phenyl)propan-2-yl)acetamide | 455.0 |
| 64 | 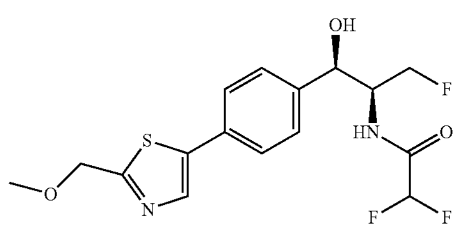 [SMILES: COCc1ncc(-c2ccc([C@@H](O)[C@@H](CF)NC(=O)C(F)F)cc2)s1] | 2,2-difluoro-N-((1R,2S)-3-fluoro-1-hydroxy-1-(4-(2-(methoxymethyl)thiazol-5-yl)phenyl)propan-2-yl)acetamide | 375.1 |
| 65 | 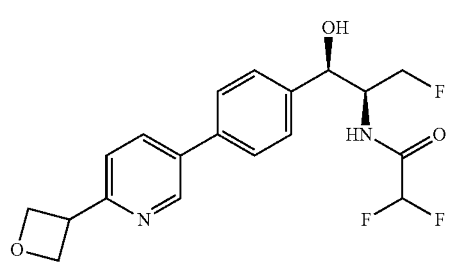 [SMILES: O=C(N[C@H](CF)[C@H](O)c1ccc(-c2ccc(C3COC3)nc2)cc1)C(F)F] | 2,2-difluoro-N-((1R,2S)-3-fluoro-1-hydroxy-1-(4-(6-(oxetan-3-yl)pyridin-3-yl)phenyl)propan-2-yl)acetamide | 381.1 |

-continued

| Example | Structure | Name | LCMS |
|---|---|---|---|
| 66 | 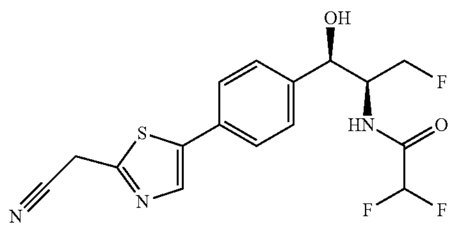 [SMILES: N#CCc1ncc(-c2ccc([C@@H](O)[C@@H](CF)NC(=O)C(F)F)cc2)s1] | N-((1R,2S)-1-(4-(2-(cyanomethyl)thiazol-5-yl)phenyl)-3-fluoro-1-hydroxypropan-2-yl)-2,2-difluoroacetamide | 370.1 |
| 67 | 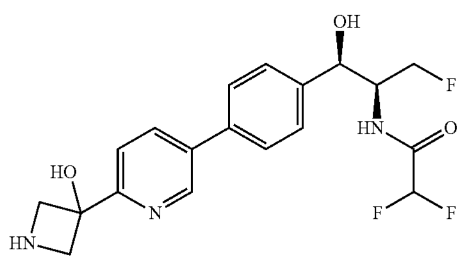 [SMILES: O=C(N[C@H](CF)[C@H](O)c1ccc(-c2ccc(C3(O)CNC3)nc2)cc1)C(F)F] | 2,2-difluoro-N-((1R,2S)-3-fluoro-1-hydroxy-1-(4-(6-(3-hydroxyazetidin-3-yl)pyridin-3-yl)phenyl)propan-2-yl)acetamide | 396.2 |
| 68 | 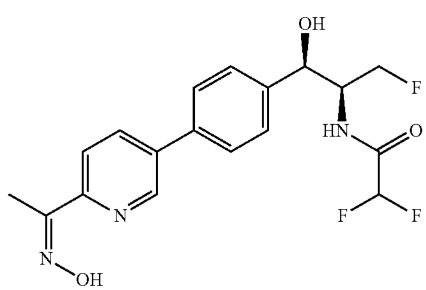 [SMILES: C/C(=N/O)c1ccc(-c2ccc([C@@H](O)[C@@H](CF)NC(=O)C(F)F)cc2)cn1] | 2,2-difluoro-N-((1R,2S)-3-fluoro-1-hydroxy-1-(4-(6-((Z)-1-(hydroxyimino)ethyl)pyridin-3-yl)phenyl)propan-2-yl)acetamide | 382.4 |
| 69 | 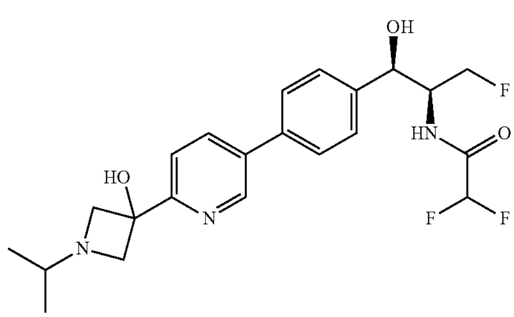 [SMILES: CC(C)N1CC(O)(c2ccc(-c3ccc([C@@H](O)[C@@H](CF)NC(=O)C(F)F)cc3)cn2)C1] | 2,2-difluoro-N-((1R,2S)-3-fluoro-1-hydroxy-1-(4-(6-(3-hydroxy-1-isopropylazetidin-3-yl)pyridin-3-yl)phenyl)propan-2-yl)acetamide | 438.2 |
| 70 | 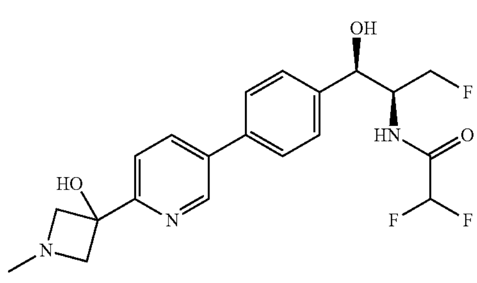 [SMILES: CN1CC(O)(c2ccc(-c3ccc([C@@H](O)[C@@H](CF)NC(=O)C(F)F)cc3)cn2)C1] | 2,2-difluoro-N-((1R,2S)-3-fluoro-1-hydroxy-1-(4-(6-(3-hydroxy-1-methylazetidin-3-yl)pyridin-3-yl)phenyl)propan-2-yl)acetamide | 410.2 |

| Example | Structure | Name | LCMS |
|---|---|---|---|
| 71 | 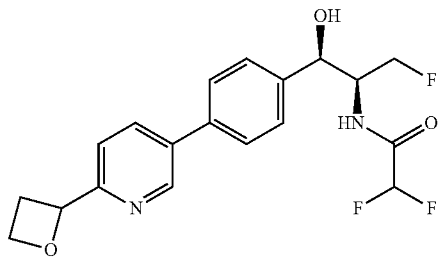 [SMILES: O=C(N[C@H](CF)[C@H](O)c1ccc(-c2ccc(C3CCO3)nc2)cc1)C(F)F] | 2,2-difluoro-N-((1R,2S)-3-fluoro-1-hydroxy-1-(4-(6-(oxetan-2-yl)pyridin-3-yl)phenyl)propan-2-yl)acetamide | 381.1 |
| 72 | 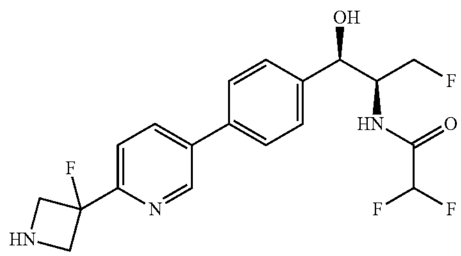 [SMILES: O=C(N[C@H](CF)[C@H](O)c1ccc(-c2ccc(C3(F)CNC3)nc2)cc1)C(F)F] | 2,2-difluoro-N-((1R,2S)-3-fluoro-1-(4-(6-(3-fluoroazetidin-3-yl)pyridin-3-yl)phenyl)-1-hydroxypropan-2-yl)acetamide | 398.1 |
| 73 | 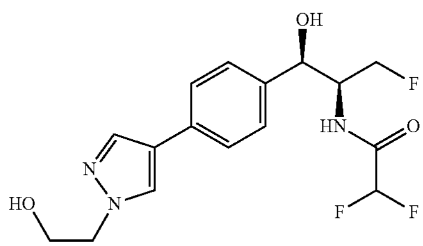 [SMILES: O=C(N[C@H](CF)[C@H](O)c1ccc(-c2cnn(CCO)c2)cc1)C(F)F] | 2,2-difluoro-N-((1R,2S)-3-fluoro-1-hydroxy-1-(4-(1-(2-hydroxyethyl)-1H-pyrazol-4-yl)phenyl)propan-2-yl)acetamide | 358.1 |
| 74 | 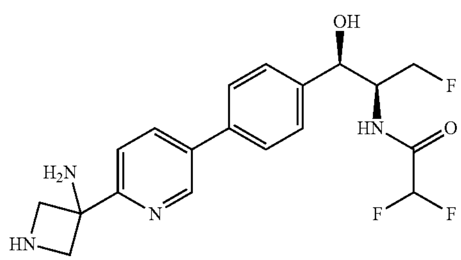 [SMILES: NC1(c2ccc(-c3ccc([C@@H](O)[C@@H](CF)NC(=O)C(F)F)cc3)cn2)CNC1] | N-((1R,2S)-1-(4-(6-(3-aminoazetidin-3-yl)pyridin-3-yl)phenyl)-3-fluoro-1-hydroxypropan-2-yl)-2,2-difluoroacetamide | 395.2 |
| 75 | 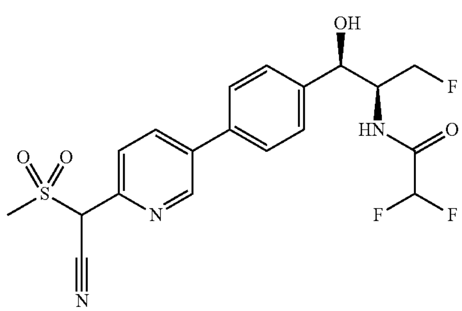 [SMILES: CS(=O)(=O)C(C#N)c1ccc(-c2ccc([C@@H](O)[C@@H](CF)NC(=O)C(F)F)cc2)cn1] | N-((1R,2S)-1-(4-(6-(cyano(methylsulfonyl)methyl)pyridin-3-yl)phenyl)-3-fluoro-1-hydroxypropan-2-yl)-2,2-difluoroacetamide | 442.1 |
| 76 | 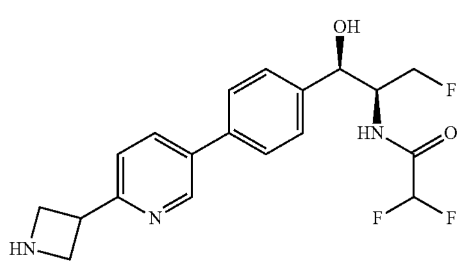 [SMILES: O=C(N[C@H](CF)[C@H](O)c1ccc(-c2ccc(C3CNC3)nc2)cc1)C(F)F] | N-((1R,2S)-1-(4-(6-(azetidin-3-yl)pyridin-3-yl)phenyl)-3-fluoro-1-hydroxypropan-2-yl)-2,2-difluoroacetamide | 380.2 |

-continued

| Example | Structure | Name | LCMS |
|---|---|---|---|
| 77 | 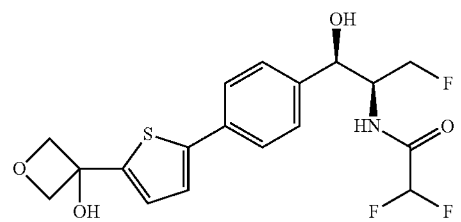 [SMILES: O=C(N[C@H](CF)[C@H](O)c1ccc(-c2ccc(C3(O)COC3)s2)cc1)C(F)F] | 2,2-difluoro-N-((1R,2S)-3-fluoro-1-hydroxy-1-(4-(2-(3-hydroxyoxetan-3-yl)thiazol-5-yl)phenyl)propan-2-yl)acetamide | 403.1 |
| 78 | 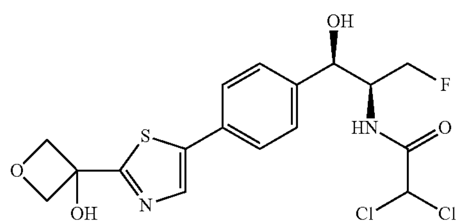 [SMILES: O=C(N[C@H](CF)[C@H](O)c1ccc(-c2cnc(C3(O)COC3)s2)cc1)C(Cl)Cl] | 2,2-dichloro-N-((1R,2S)-3-fluoro-1-hydroxy-1-(4-(2-(3-hydroxyoxetan-3-yl)thiazol-5-yl)phenyl)propan-2-yl)acetamide | 435.0 |
| 79 | 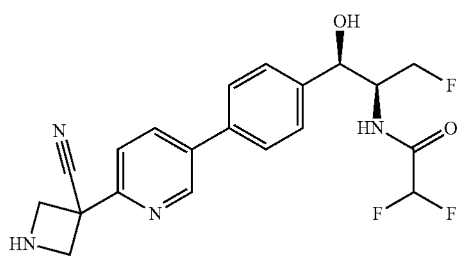 [SMILES: N#CC1(c2ccc(-c3ccc([C@@H](O)[C@@H](CF)NC(=O)C(F)F)cc3)cn2)CNC1] | N-((1R,2S)-1-(4-(6-(3-cyanoazetidin-3-yl)pyridin-3-yl)phenyl)-3-fluoro-1-hydroxypropan-2-yl)-2,2-difluoroacetamide | 405.2 |
| 80 | 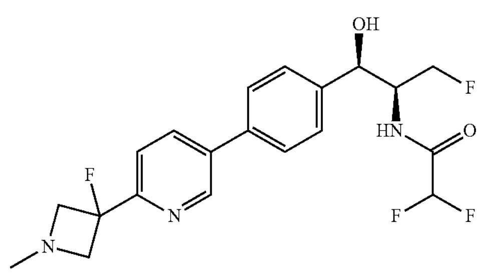 [SMILES: CN1CC(F)(c2ccc(-c3ccc([C@@H](O)[C@@H](CF)NC(=O)C(F)F)cc3)cn2)C1] | 2,2-difluoro-N-((1R,2S)-3-fluoro-1-(4-(6-(3-fluoro-1-methylazetidin-3-yl)pyridin-3-yl)phenyl)-1-hydroxypropan-2-yl)acetamide | 412.2 |
| 81 | 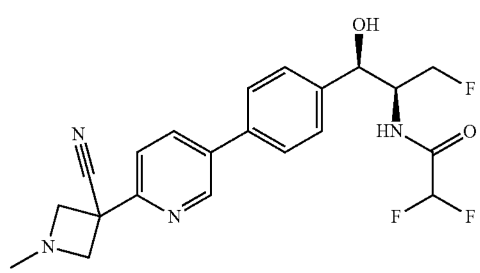 [SMILES: CN1CC(C#N)(c2ccc(-c3ccc([C@@H](O)[C@@H](CF)NC(=O)C(F)F)cc3)cn2)C1] | N-((1R,2S)-1-(4-(6-(3-cyano-1-methylazetidin-3-yl)pyridin-3-yl)phenyl)-3-fluoro-1-hydroxypropan-2-yl)-2,2-difluoroacetamide | 419.2 |
| 82 | 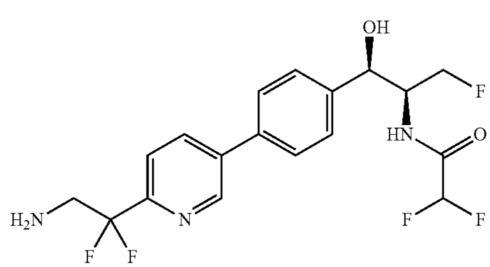 [SMILES: NCC(F)(F)c1ccc(-c2ccc([C@@H](O)[C@@H](CF)NC(=O)C(F)F)cc2)cn1] | N-((1R,2S)-1-(4-(6-(2-amino-1,1-difluoroethyl)pyridin-3-yl)phenyl)-3-fluoro-1-hydroxypropan-2-yl)-2,2-difluoroacetamide | 404.1 |

| Example | Structure | Name | LCMS |
|---|---|---|---|
| 83 | 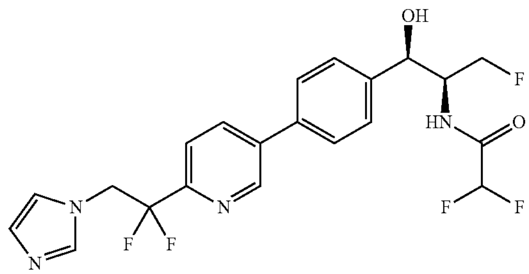 [SMILES: O=C(N[C@H](CF)[C@H](O)c1ccc(-c2ccc(C(F)(F)Cn3ccnc3)nc2)cc1)C(F)F] | N-((1R,2S)-1-(4-(6-(1,1-difluoro-2-(1H-imidazol-1-yl)ethyl)pyridin-3-yl)phenyl)-3-fluoro-1-hydroxypropan-2-yl)-2,2-difluoroacetamide | 455.1 |
| 84 | 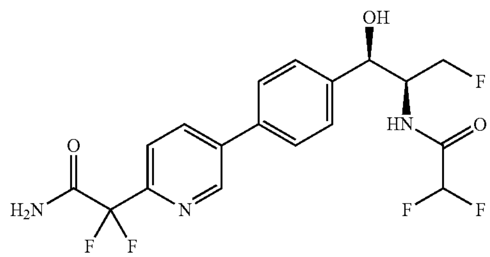 [SMILES: NC(=O)C(F)(F)c1ccc(-c2ccc([C@@H](O)[C@@H](CF)NC(=O)C(F)F)cc2)cn1] | N-((1R,2S)-1-(4-(6-(2-amino-1,1-difluoro-2-oxoethyl)pyridin-3-yl)phenyl)-3-fluoro-1-hydroxypropan-2-yl)-2,2-difluoroacetamide | 418.1 |
| 85 | 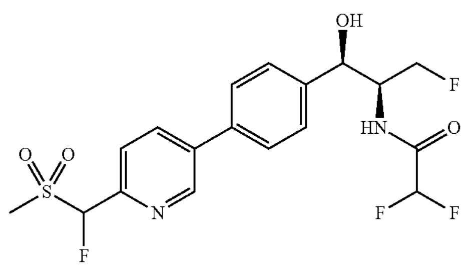 [SMILES: CS(=O)(=O)C(F)c1ccc(-c2ccc([C@@H](O)[C@@H](CF)NC(=O)C(F)F)cc2)cn1] | 2,2-difluoro-N-((1R,2S)-3-fluoro-1-(4-(6-(fluoro(methylsulfonyl)methyl)pyridin-3-yl)phenyl)-1-hydroxypropan-2-yl)acetamide | 435.1 |
| 86 | 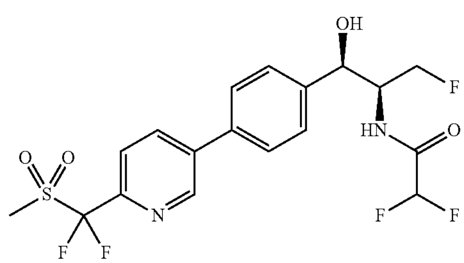 [SMILES: CS(=O)(=O)C(F)(F)c1ccc(-c2ccc([C@@H](O)[C@@H](CF)NC(=O)C(F)F)cc2)cn1] | N-((1R,2S)-1-(4-(6-(difluoro(methylsulfonyl)methyl)pyridin-3-yl)phenyl)-3-fluoro-1-hydroxypropan-2-yl)-2,2-difluoroacetamide | 453.1 |
| 87 | 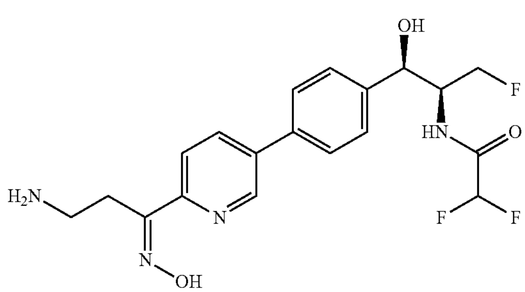 [SMILES: NCC/C(=N/O)c1ccc(-c2ccc([C@@H](O)[C@@H](CF)NC(=O)C(F)F)cc2)cn1] | N-((1R,2S)-1-(4-(6-((Z)-3-amino-1-(hydroxyimino)propyl)pyridin-3-yl)phenyl)-3-fluoro-1-hydroxypropan-2-yl)-2,2-difluoroacetamide | 411.2 |
| 88 | 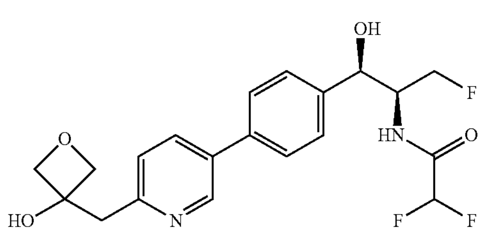 [SMILES: O=C(N[C@H](CF)[C@H](O)c1ccc(-c2ccc(CC3(O)COC3)nc2)cc1)C(F)F] | 2,2-difluoro-N-((1R,2S)-3-fluoro-1-hydroxy-1-(4-(6-((3-hydroxyoxetan-3-yl)methyl)pyridin-3-yl)phenyl)propan-2-yl)acetamide | 411.2 |

-continued

| Example | Structure | Name | LCMS |
|---|---|---|---|
| 89 | 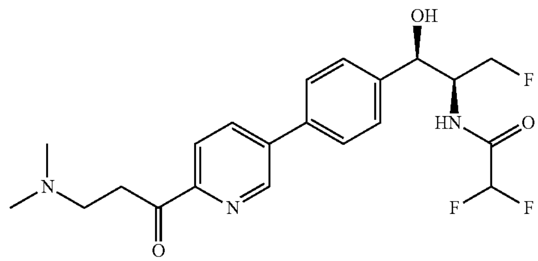 [SMILES: CN(C)CCC(=O)c1ccc(-c2ccc([C@@H](O)[C@@H](CF)NC(=O)C(F)F)cc2)cn1] | N-((1R,2S)-1-(4-(6-(3-(dimethylamino)propanoyl)pyridin-3-yl)phenyl)-3-fluoro-1-hydroxypropan-2-yl)-2,2-difluoroacetamide | |
| 90 | 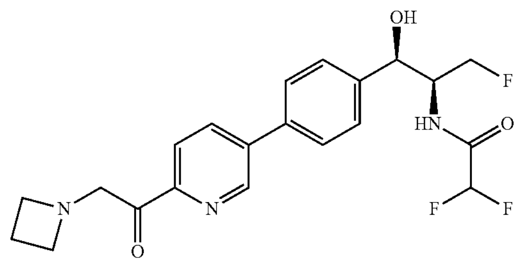 [SMILES: O=C(CN1CCC1)c1ccc(-c2ccc([C@@H](O)[C@@H](CF)NC(=O)C(F)F)cc2)cn1] | N-((1R,2S)-1-(4-(6-(2-(azetidin-1-yl)acetyl)pyridin-3-yl)phenyl)-3-fluoro-1-hydroxypropan-2-yl)-2,2-difluoroacetamide | |
| 91 | 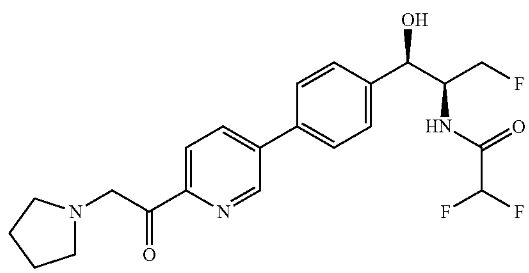 [SMILES: O=C(CN1CCCC1)c1ccc(-c2ccc([C@@H](O)[C@@H](CF)NC(=O)C(F)F)cc2)cn1] | 2,2-difluoro-N-((1R,2S)-3-fluoro-1-hydroxy-1-(4-(6-(2-(pyrrolidin-1-yl)acetyl)pyridin-3-yl)phenyl)propan-2-yl)acetamide | |
| 92 | 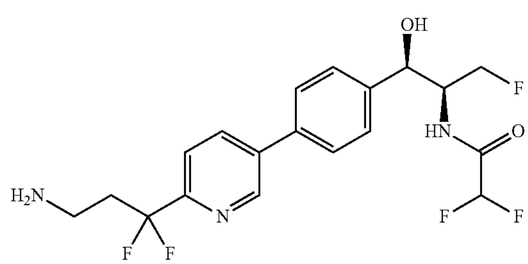 [SMILES: NCCC(F)(F)c1ccc(-c2ccc([C@@H](O)[C@@H](CF)NC(=O)C(F)F)cc2)cn1] | 2,2-difluoro-N-((1R,2S)-3-fluoro-1-hydroxy-1-(4-(6-(2-(pyrrolidin-1-yl)acetyl)pyridin-3-yl)phenyl)propan-2-yl)acetamide | |
| 93 | 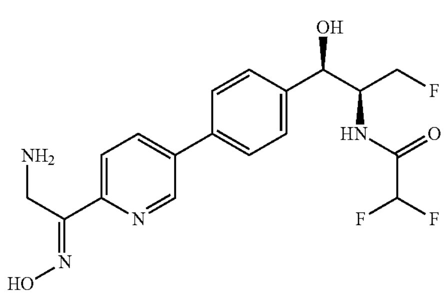 [SMILES: NC/C(=N\O)c1ccc(-c2ccc([C@@H](O)[C@@H](CF)NC(=O)C(F)F)cc2)cn1] | N-((1R,2S)-1-(4-(6-((E)-2-amino-1-(hydroxyimino)ethyl)pyridin-3-yl)phenyl)-3-fluoro-1-hydroxypropan-2-yl)-2,2-difluoroacetamide | |
| 94 | 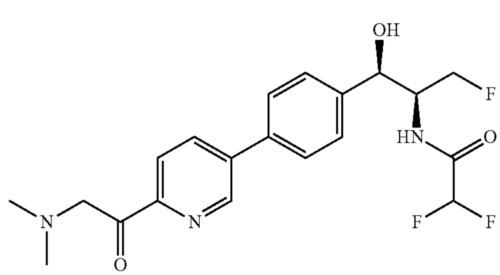 [SMILES: CN(C)CC(=O)c1ccc(-c2ccc([C@@H](O)[C@@H](CF)NC(=O)C(F)F)cc2)cn1] | N-((1R,2S)-1-(4-(6-(2-(dimethylamino)acetyl)pyridin-3-yl)phenyl)-3-fluoro-1-hydroxypropan-2-yl)-2,2-difluoroacetamide | |

-continued

| Example | Structure | Name | LCMS |
|---|---|---|---|
| 95 | 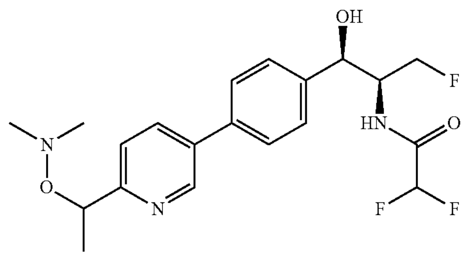 [SMILES: CC(ON(C)C)c1ccc(-c2ccc([C@@H](O)[C@@H](CF)NC(=O)C(F)F)cc2)cn1] | N-((1R,2S)-1-(4-(6-(1-((dimethylamino)oxy)ethyl)pyridin-3-yl)phenyl)-3-fluoro-1-hydroxypropan-2-yl)-2,2-difluoroacetamide | 412.4 |
| 96 | 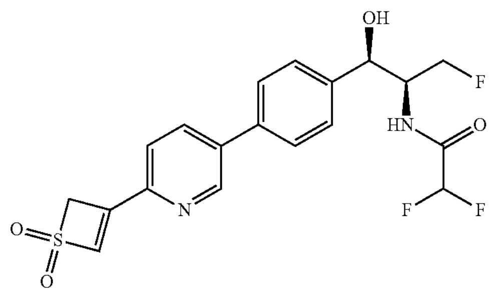 [SMILES: O=C(N[C@H](CF)[C@H](O)c1ccc(-c2ccc(C3=CS(=O)(=O)C3)nc2)cc1)C(F)F] | N-((1R,2S)-1-(4-(6-(1,1-dioxido-2H-thiet-3-yl)pyridin-3-yl)phenyl)-3-fluoro-1-hydroxypropan-2-yl)-2,2-difluoroacetamide | 426.4 |
| 97 | 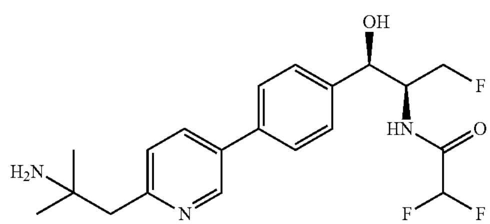 [SMILES: CC(C)(N)Cc1ccc(-c2ccc([C@@H](O)[C@@H](CF)NC(=O)C(F)F)cc2)cn1] | N-((1R,2S)-1-(4-(6-(2-amino-2-methylpropyl)pyridin-3-yl)phenyl)-3-fluoro-1-hydroxypropan-2-yl)-2,2-difluoroacetamide | 396.4 |
| 98 | 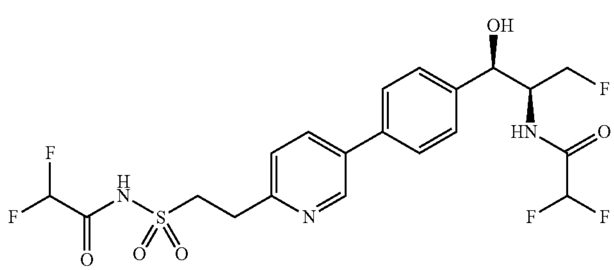 [SMILES: O=C(N[C@H](CF)[C@H](O)c1ccc(-c2ccc(CCS(=O)(=O)NC(=O)C(F)F)nc2)cc1)C(F)F] | N-((2-(5-(4-((1R,2S)-2-(2,2-difluoroacetamido)-3-fluoro-1-hydroxypropyl)phenyl)pyridin-2-yl)ethyl)sulfonyl)-2,2-difluoroacetamide | 510.5 |
| 99 | 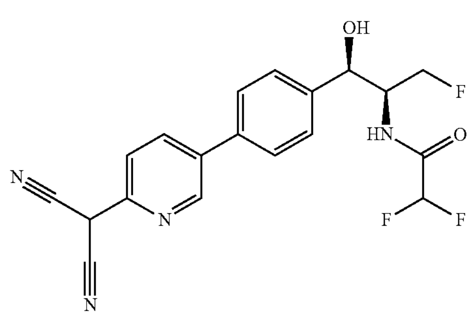 [SMILES: N#CC(C#N)c1ccc(-c2ccc([C@@H](O)[C@@H](CF)NC(=O)C(F)F)cc2)cn1] | N-((1R,2S)-1-(4-(6-(dicyanomethyl)pyridin-3-yl)phenyl)-3-fluoro-1-hydroxypropan-2-yl)-2,2-difluoroacetamide | 389.3 |

| Example | Structure | Name | LCMS |
|---|---|---|---|
| 100 | 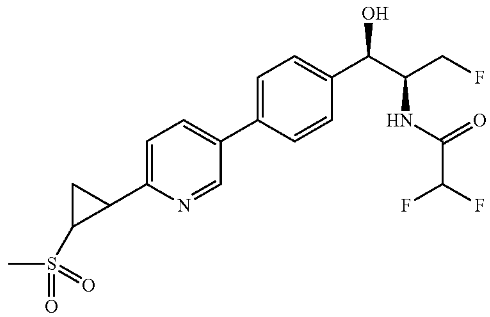 [SMILES: CS(=O)(=O)C1CC1c1ccc(-c2ccc([C@@H](O)[C@@H](CF)NC(=O)C(F)F)cc2)cn1] | 2,2-difluoro-N-((1R,2S)-3-fluoro-1-hydroxy-1-(4-(6-(2-(methylsulfonyl)cyclopropyl)pyridin-3-yl)phenyl)propan-2-yl)acetamide | 443.5 |
| 101 | 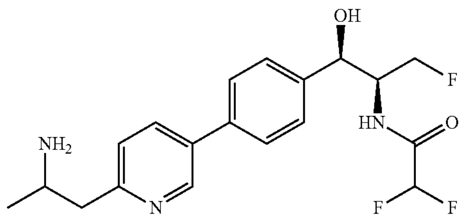 [SMILES: CC(N)Cc1ccc(-c2ccc([C@@H](O)[C@@H](CF)NC(=O)C(F)F)cc2)cn1] | N-((1R,2S)-1-(4-(6-(2-aminopropyl)pyridin-3-yl)phenyl)-3-fluoro-1-hydroxypropan-2-yl)-2,2-difluoroacetamide | |
| 102 | 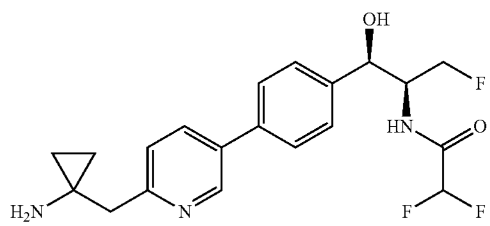 [SMILES: NC1(Cc2ccc(-c3ccc([C@@H](O)[C@@H](CF)NC(=O)C(F)F)cc3)cn2)CC1] | N-((1R,2S)-1-(4-(6-((1-aminocyclopropyl)methyl)pyridin-3-yl)phenyl)-3-fluoro-1-hydroxypropan-2-yl)-2,2-difluoroacetamide | |
| 103 | 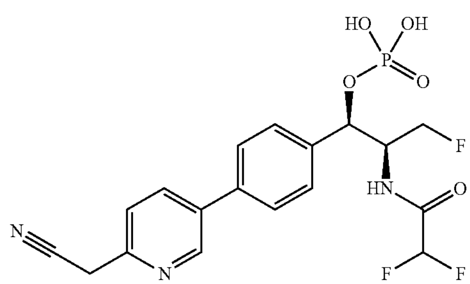 [SMILES: N#CCc1ccc(-c2ccc([C@@H](OP(=O)(O)O)[C@@H](CF)NC(=O)C(F)F)cc2)cn1] | (1R,2S)-1-(4-(6-(cyanomethyl)pyridin-3-yl)phenyl)-2-(2,2-difluoroacetamido)-3-fluoropropyl dihydrogen phosphate | 444.3 |

We claim:

1. A compound of formula

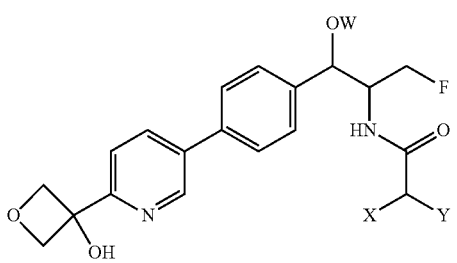

its enantiomers, diastereomers, or pharmaceutical acceptable salts thereof wherein:

W is —H or —PO(OH)$_2$; and

X and Y are each independently halo.

2. A pharmaceutical composition comprising a compound of claim 1, or a pharmaceutically acceptable salt thereof and a pharmaceutically acceptable carrier.

3. A compound selected from the group consisting of:
2,2-difluoro-N-((1R,2S)-3-fluoro-1-hydroxy-1-(4-(6-(3-hydroxyoxetan-3-yl)pyridin-3-yl)phenyl)propan-2-yl) acetamide;
3-[5-(4-{(1R,2S)-2-[(difluoroacetyl)amino]-3-fluoro-1-hydroxypropyl}phenyl)pyridin-2-yl]oxetan-3-yl dihydrogen phosphate;
(1R,2S)-2-[(difluoroacetyl)amino]-3-fluoro-1-{4-[6-(3-hydroxyoxetan-3-yl)pyridin-3-yl]phenyl}propyl dihydrogen phosphate; and
2,2-dichloro-N-[(1S,2R)-1-(fluoromethyl)-2-{4-[6-(3-hydroxyoxetan-3-yl)pyridin-3-yl]phenyl}-2-hydroxyethyl]acetamide.

4. A compound which is 2,2-difluoro-N-((1R,2S)-3-fluoro-1-hydroxy-1-(4-(6-(3-hydroxyoxetan-3-yl)pyridin-3-yl)phenyl)propan-2-yl)acetamide.

* * * * *